United States Patent
Wu et al.

(10) Patent No.: US 8,815,888 B2
(45) Date of Patent: *Aug. 26, 2014

(54) FORMS OF RIFAXIMIN AND USES THEREOF

(71) Applicants: Yiduo Wu, New Brunswick, NJ (US); Stephan D. Parent, West Lafayette, IN (US); Nathan Carl Schultheiss, Lafayette, IN (US); Melanie Janelle Bevill, West Lafayette, IN (US); Petinka Vlahova, West Lafayette, IN (US); Travis L. Houston, Lafayette, IN (US)

(72) Inventors: Yiduo Wu, New Brunswick, NJ (US); Stephan D. Parent, West Lafayette, IN (US); Nathan Carl Schultheiss, Lafayette, IN (US); Melanie Janelle Bevill, West Lafayette, IN (US); Petinka Vlahova, West Lafayette, IN (US); Travis L. Houston, Lafayette, IN (US)

(73) Assignee: Salix Pharmaceuticals, Ltd., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/955,660

(22) Filed: Jul. 31, 2013

(65) Prior Publication Data

US 2013/0317225 A1    Nov. 28, 2013

Related U.S. Application Data

(63) Continuation of application No. 13/152,804, filed on Jun. 3, 2011, now Pat. No. 8,513,275.

(60) Provisional application No. 61/351,281, filed on Jun. 3, 2010, provisional application No. 61/357,505, filed on Jun. 22, 2010, provisional application No. 61/363,241, filed on Jul. 10, 2010, provisional application No. 61/363,511, filed on Jul. 12, 2010, provisional application No. 61/367,185, filed on Jul. 23, 2010, provisional application No. 61/416,593, filed on Nov. 23, 2010.

(51) Int. Cl.
*C07D 498/22*    (2006.01)
*A61K 31/04*    (2006.01)

(52) U.S. Cl.
USPC ............................ 514/279; 540/456

(58) Field of Classification Search
USPC ............................ 514/279; 540/456
See application file for complete search history.

*Primary Examiner* — Bruck Kifle
(74) *Attorney, Agent, or Firm* — McCarter & English, LLP; Jonathan M. Sparks

(57) ABSTRACT

The present invention relates to new rifaximin forms kappa, theta, rifaximin:piperazine cocrystal 1 and rifaximin:piperazine cocrystal 2, methods of making same and to their use in medicinal preparations and therapeutic methods.

20 Claims, 62 Drawing Sheets

| | |
|---|---|
| File Name | 405790.Fsh |
| Experiment | Temp-RH |
| Operator | DSO |
| Experiment ID | 405790 |
| Sample Name | rifaximin |
| Sample Lot # | 3973-44-03, LIMS #229836 |
| Notes | Range 5% to 95% |
| | 25°C at 10 % increments |
| Drying | OFF |
| Max Equil Time | 180 min |
| Equil Crit | 0.0100 wt % in 5.00min |
| T-RH Steps | 25, 5; 25, 15; 25, 25; 25, 35; 25, 45; 25, 55; 25, 65; 25, 75; 25, 85; 25, 95; 25, 85; 25, 75; 25, 65; 25, 55; 25, 45; 25, 35; 25, 25; 25, 15; 25, 5 |
| Data Logging Interval | 2.00 min or 0.0100 wt % |
| Expt Started | 6/26/2010 |
| Run Started | 6:21:03 |

| Step Time min | Elap Time min | Weight mg | Weight % chg | Samp Temp deg C | Samp RH % |
|---|---|---|---|---|---|
| n/a | 0.1 | 10.063 | 0.000 | 24.82 | 3.40 |
| 175.8 | 175.9 | 9.311 | -7.479 | 24.85 | 4.83 |
| 15.6 | 191.4 | 9.357 | -7.017 | 24.85 | 15.11 |
| 16.7 | 208.1 | 9.410 | -6.492 | 24.85 | 24.91 |
| 15.6 | 223.7 | 9.465 | -5.947 | 24.84 | 34.86 |
| 16.1 | 239.8 | 9.518 | -5.420 | 24.85 | 44.84 |
| 14.3 | 254.1 | 9.568 | -4.919 | 24.85 | 54.94 |
| 14.8 | 268.9 | 9.620 | -4.407 | 24.85 | 64.82 |
| 14.5 | 283.4 | 9.670 | -3.905 | 24.86 | 74.51 |
| 14.6 | 298.0 | 9.720 | -3.409 | 24.85 | 84.49 |
| 15.1 | 313.0 | 9.771 | -2.903 | 24.85 | 94.81 |
| 183.7 | 496.8 | 9.498 | -5.620 | 24.84 | 84.60 |
| 183.5 | 680.3 | 9.346 | -7.134 | 24.85 | 75.45 |
| 149.9 | 830.1 | 9.218 | -8.402 | 24.86 | 65.05 |
| 81.0 | 911.1 | 9.109 | -9.486 | 24.86 | 55.15 |
| 121.4 | 1032.5 | 8.972 | -10.848 | 24.86 | 45.15 |
| 75.7 | 1108.2 | 8.862 | -11.939 | 24.86 | 35.04 |
| 68.4 | 1176.6 | 8.757 | -12.987 | 24.86 | 25.02 |
| 52.7 | 1229.2 | 8.661 | -13.932 | 24.85 | 15.12 |
| 46.8 | 1276.1 | 8.561 | -14.934 | 24.85 | 5.05 |

Fig. 9
CONTINUED

| | | | | | |
|---|---|---|---|---|---|
| File Name | | 405792.Fsh | | | |
| Experiment | | Temp-RH | | | |
| Operator | | DSO | | | |
| Experiment ID | | 405792 | | | |
| Sample Name | | rifaximin | | | |
| Sample Lot # | | 3973-62-01, LIMS #231571 | | | |
| Notes | | Range 5% to 95% | | | |
| | | 25°C at 10 % increments | | | |
| Drying | | OFF | | | |
| Max Equil Time | | 180 min | | | |
| Equil Crit | | 0.0100 wt % in | 5.00min | | |
| T-RH Steps | | 25, 5; 25, 15; 25, 25; 25, 35; 25, 45; 25, 55; 25, 65; 25, 75; 25, 85; 25, 95; 25, 85; 25, 75; 25, 65; 25, 55; 25, 45; 25, 35; 25, 25; 25, 15; 25, 5 | | | |
| Data Logging Interval | | 2.00 min or | 0.0100 wt % | | |
| Expt Started | | 6/27/2010 | | | |
| Run Started | | 8:28:38 | | | |

| Step Time min | Elap Time min | Weight mg | Weight % chg | Samp Temp deg C | Samp RH % |
|---|---|---|---|---|---|
| n/a | 0.1 | 11.041 | 0.000 | 24.86 | 3.08 |
| 15.2 | 15.3 | 11.033 | -0.073 | 24.87 | 5.25 |
| 20.0 | 35.2 | 11.084 | 0.391 | 24.87 | 14.83 |
| 22.1 | 57.3 | 11.146 | 0.951 | 24.86 | 24.86 |
| 30.1 | 87.3 | 11.215 | 1.575 | 24.84 | 34.84 |
| 39.3 | 126.6 | 11.292 | 2.276 | 24.84 | 44.82 |
| 39.3 | 165.9 | 11.374 | 3.015 | 24.85 | 54.82 |
| 48.8 | 214.6 | 11.469 | 3.875 | 24.85 | 64.84 |
| 63.2 | 277.8 | 11.578 | 4.864 | 24.86 | 74.91 |
| 74.1 | 351.8 | 11.704 | 6.006 | 24.85 | 84.77 |
| 107.8 | 459.6 | 11.886 | 7.656 | 24.86 | 94.96 |
| 157.6 | 617.2 | 11.745 | 6.379 | 24.86 | 85.01 |
| 92.7 | 709.9 | 11.630 | 5.334 | 24.85 | 75.17 |
| 117.9 | 827.8 | 11.486 | 4.035 | 24.86 | 65.05 |
| 113.1 | 940.9 | 11.338 | 2.693 | 24.86 | 55.08 |
| 103.8 | 1044.7 | 11.189 | 1.342 | 24.85 | 45.00 |
| 97.5 | 1142.2 | 11.046 | 0.045 | 24.85 | 34.97 |
| 70.3 | 1212.4 | 10.922 | -1.078 | 24.86 | 25.05 |
| 51.6 | 1264.1 | 10.801 | -2.174 | 24.86 | 15.17 |
| 45.6 | 1309.6 | 10.675 | -3.318 | 24.86 | 5.13 |

Fig. 15
CONTINUED

| °2θ | d space (Å) | Intensity (%) |
|---|---|---|
| 5.74 ± 0.10 | 15.410 ± 0.273 | 38 |
| 6.58 ± 0.10 | 13.435 ± 0.207 | 83 |
| 7.49 ± 0.10 | 11.804 ± 0.160 | 100 |
| 8.21 ± 0.10 | 10.772 ± 0.133 | 66 |
| 9.22 ± 0.10 | 9.593 ± 0.105 | 8 |
| 9.83 ± 0.10 | 8.999 ± 0.092 | 25 |
| 10.32 ± 0.10 | 8.570 ± 0.084 | 6 |
| 10.73 ± 0.10 | 8.244 ± 0.077 | 6 |
| 10.93 ± 0.10 | 8.093 ± 0.074 | 11 |
| 11.67 ± 0.10 | 7.585 ± 0.065 | 4 |
| 12.09 ± 0.10 | 7.323 ± 0.061 | 5 |
| 12.41 ± 0.10 | 7.132 ± 0.058 | 17 |
| 12.60 ± 0.10 | 7.024 ± 0.056 | 18 |
| 12.70 ± 0.10 | 6.968 ± 0.055 | 19 |
| 13.24 ± 0.10 | 6.688 ± 0.051 | 12 |
| 13.52 ± 0.10 | 6.548 ± 0.049 | 10 |
| 13.88 ± 0.10 | 6.380 ± 0.046 | 14 |
| 15.00 ± 0.10 | 5.906 ± 0.039 | 17 |
| 15.47 ± 0.10 | 5.728 ± 0.037 | 9 |
| 15.97 ± 0.10 | 5.549 ± 0.035 | 11 |
| 16.25 ± 0.10 | 5.456 ± 0.034 | 10 |
| 16.56 ± 0.10 | 5.355 ± 0.032 | 12 |
| 17.42 ± 0.10 | 5.090 ± 0.029 | 6 |
| 17.60 ± 0.10 | 5.039 ± 0.029 | 9 |
| 18.15 ± 0.10 | 4.887 ± 0.027 | 22 |
| 18.49 ± 0.10 | 4.800 ± 0.026 | 7 |
| 19.19 ± 0.10 | 4.626 ± 0.024 | 17 |
| 19.74 ± 0.10 | 4.498 ± 0.023 | 15 |
| 20.21 ± 0.10 | 4.395 ± 0.022 | 25 |
| 20.59 ± 0.10 | 4.313 ± 0.021 | 11 |
| 20.83 ± 0.10 | 4.264 ± 0.020 | 9 |
| 21.41 ± 0.10 | 4.150 ± 0.019 | 7 |
| 22.13 ± 0.10 | 4.017 ± 0.018 | 7 |
| 22.66 ± 0.10 | 3.925 ± 0.017 | 5 |
| 23.13 ± 0.10 | 3.845 ± 0.016 | 8 |
| 23.97 ± 0.10 | 3.713 ± 0.015 | 15 |
| 24.99 ± 0.10 | 3.564 ± 0.014 | 10 |
| 25.76 ± 0.10 | 3.458 ± 0.013 | 9 |
| 26.85 ± 0.10 | 3.321 ± 0.012 | 5 |
| 27.20 ± 0.10 | 3.279 ± 0.012 | 9 |
| 27.94 ± 0.10 | 3.193 ± 0.011 | 4 |
| 28.68 ± 0.10 | 3.113 ± 0.011 | 5 |

Fig. 26

| °2θ | d space (Å) | Intensity (%) |
|---|---|---|
| 5.74 ± 0.10 | 15.410 ± 0.273 | 38 |
| 6.58 ± 0.10 | 13.435 ± 0.207 | 83 |
| 7.49 ± 0.10 | 11.804 ± 0.160 | 100 |
| 8.21 ± 0.10 | 10.772 ± 0.133 | 66 |
| 9.83 ± 0.10 | 8.999 ± 0.092 | 25 |

Observed IR peaks for Rifaximin:piperazine cocrystal 1
Region      4000.0   400.0
Absolute threshold: 0.0251
Sensitivity: 90
Observed Peak list (+/-2 cm$^{-1}$):
701.5
726.2
766.0
792.5
803.5
819.7
881.3
906.6
925.2
947.7
971.9
1021.8
1047.4
1061.3
1094.2
1119.9
1158.2
1223.2
1237.3
1319.7
1338.3
1372.3
1461.3
1502.7
1571.5
1589.3
1646.6
1721.4
2882.4
2935.2
2969.1
3424.3
3737.9

Fig. 34

Observed Raman peaks for Rifaximin:piperazine cocrystal 1
Spectrum:         rifaximin
Region:           3600.4    98.3
Absolute threshold: 0.165
Sensitivity:      80
Peak list (+/-2 cm$^{-1}$):
 156.5
 254.4
 323.8
 353.7
 390.6
 439.8
 467.4
 489.2
 546.8
 628.7
 648.0
 667.9
 725.9
 767.4
 797.9
 824.0
 891.9
 923.1
 950.3
 1054.7
 1133.3
 1158.8
 1207.4
 1273.7
 1298.3
 1348.6
 1379.5
 1420.5
 1532.3
 1587.5
 1650.2
 2724.8
 2935.2
 2988.8

Fig. 36

| °2θ | d space (Å) | Intensity (%) | °2θ | d space (Å) | Intensity (%) |
|---|---|---|---|---|---|
| 3.64 ± 0.10 | 24.288 ± 0.686 | 19 | 17.76 ± 0.10 | 4.995 ± 0.028 | 5 |
| 5.58 ± 0.10 | 15.825 ± 0.288 | 44 | 17.94 ± 0.10 | 4.944 ± 0.027 | 8 |
| 6.45 ± 0.10 | 13.696 ± 0.215 | 100 | 18.36 ± 0.10 | 4.832 ± 0.026 | 6 |
| 7.19 ± 0.10 | 12.297 ± 0.173 | 28 | 18.61 ± 0.10 | 4.768 ± 0.026 | 4 |
| 7.29 ± 0.10 | 12.128 ± 0.168 | 54 | 18.74 ± 0.10 | 4.734 ± 0.025 | 6 |
| 7.60 ± 0.10 | 11.635 ± 0.155 | 23 | 19.14 ± 0.10 | 4.638 ± 0.024 | 7 |
| 8.27 ± 0.10 | 10.696 ± 0.131 | 29 | 19.35 ± 0.10 | 4.586 ± 0.024 | 20 |
| 9.01 ± 0.10 | 9.815 ± 0.110 | 26 | 19.76 ± 0.10 | 4.492 ± 0.023 | 15 |
| 9.82 ± 0.10 | 9.006 ± 0.092 | 2 | 19.96 ± 0.10 | 4.449 ± 0.022 | 7 |
| 10.54 ± 0.10 | 8.394 ± 0.080 | 9 | 20.33 ± 0.10 | 4.368 ± 0.021 | 27 |
| 10.73 ± 0.10 | 8.244 ± 0.077 | 3 | 20.64 ± 0.10 | 4.303 ± 0.021 | 5 |
| 10.95 ± 0.10 | 8.081 ± 0.074 | 4 | 20.83 ± 0.10 | 4.264 ± 0.020 | 11 |
| 11.19 ± 0.10 | 7.906 ± 0.071 | 2 | 21.18 ± 0.10 | 4.194 ± 0.020 | 5 |
| 11.93 ± 0.10 | 7.421 ± 0.063 | 2 | 21.39 ± 0.10 | 4.155 ± 0.019 | 5 |
| 12.26 ± 0.10 | 7.219 ± 0.059 | 6 | 21.53 ± 0.10 | 4.128 ± 0.019 | 10 |
| 12.41 ± 0.10 | 7.132 ± 0.058 | 8 | 21.71 ± 0.10 | 4.093 ± 0.019 | 7 |
| 12.55 ± 0.10 | 7.052 ± 0.056 | 15 | 22.00 ± 0.10 | 4.040 ± 0.018 | 3 |
| 12.80 ± 0.10 | 6.914 ± 0.054 | 11 | 22.24 ± 0.10 | 3.998 ± 0.018 | 8 |
| 13.45 ± 0.10 | 6.585 ± 0.049 | 7 | 22.56 ± 0.10 | 3.941 ± 0.017 | 6 |
| 13.66 ± 0.10 | 6.484 ± 0.048 | 13 | 22.85 ± 0.10 | 3.892 ± 0.017 | 6 |
| 13.84 ± 0.10 | 6.399 ± 0.046 | 13 | 23.18 ± 0.10 | 3.837 ± 0.016 | 5 |
| 14.30 ± 0.10 | 6.194 ± 0.043 | 5 | 23.36 ± 0.10 | 3.809 ± 0.016 | 7 |
| 14.42 ± 0.10 | 6.141 ± 0.043 | 6 | 23.99 ± 0.10 | 3.709 ± 0.015 | 10 |
| 14.60 ± 0.10 | 6.067 ± 0.042 | 12 | 24.35 ± 0.10 | 3.655 ± 0.015 | 6 |
| 15.32 ± 0.10 | 5.784 ± 0.038 | 5 | 24.69 ± 0.10 | 3.605 ± 0.014 | 6 |
| 15.56 ± 0.10 | 5.695 ± 0.037 | 4 | 24.89 ± 0.10 | 3.578 ± 0.014 | 9 |
| 16.00 ± 0.10 | 5.538 ± 0.035 | 9 | 25.35 ± 0.10 | 3.514 ± 0.014 | 5 |
| 16.32 ± 0.10 | 5.431 ± 0.033 | 14 | 25.70 ± 0.10 | 3.467 ± 0.013 | 11 |
| 16.62 ± 0.10 | 5.333 ± 0.032 | 9 | 26.66 ± 0.10 | 3.344 ± 0.012 | 13 |
| 16.81 ± 0.10 | 5.273 ± 0.031 | 6 | 27.00 ± 0.10 | 3.302 ± 0.012 | 6 |
| 17.18 ± 0.10 | 5.161 ± 0.030 | 4 | 27.18 ± 0.10 | 3.280 ± 0.012 | 5 |
| 17.51 ± 0.10 | 5.065 ± 0.029 | 22 | | | |

Fig. 40

| °2θ | d space (Å) | Intensity (%) |
|---|---|---|
| 3.64 ± 0.10 | 24.288 ± 0.686 | 19 |
| 5.58 ± 0.10 | 15.825 ± 0.288 | 44 |
| 6.45 ± 0.10 | 13.696 ± 0.215 | 100 |
| 7.29 ± 0.10 | 12.128 ± 0.168 | 54 |
| 7.60 ± 0.10 | 11.635 ± 0.155 | 23 |
| 8.27 ± 0.10 | 10.696 ± 0.131 | 29 |
| 9.01 ± 0.10 | 9.815 ± 0.110 | 26 |

Observed and Characteristic IR peaks for Rifaximin: piperazine cocrystal 2
Spectrum: rifaximin
Region     4000.0   400.0
Absolute threshold: 0.0040
Sensitivity: 90

| Observed Peak list (+/-2 cm$^{-1}$): | Characteristic Peaks (+/- 2 cm$^{-1}$): |
|---|---|
| 704.0 | 1452.9 |
| 725.7 | 2251.1 |
| 735.9 | |
| 760.1 | |
| 803.6 | |
| 820.9 | |
| 836.8 | |
| 850.6 | |
| 880.6 | |
| 906.5 | |
| 923.7 | |
| 946.4 | |
| 974.1 | |
| 1020.8 | |
| 1046.2 | |
| 1062.2 | |
| 1091.7 | |
| 1122.6 | |
| 1159.2 | |
| 1221.4 | |
| 1237.3 | |
| 1319.3 | |
| 1337.7 | |
| 1370.9 | |
| 1452.9 | |
| 1504.8 | |
| 1568.4 | |
| 1590.1 | |
| 1647.8 | |
| 1726.4 | |
| 2251.1 | |
| 2883.7 | |
| 2934.9 | |
| 2970.5 | |
| 3249.2 | |
| 3419.5 | |

Fig. 45

Observed and Characteristic Raman peaks for Rifaximin:piperazine cocrystal 2
Spectrum: rifaximin
Region: 3600.4  98.3
Absolute threshold: 0.209
Sensitivity: 80
Peak lists (+/-2 cm$^{-1}$):

| Observed Peaks: | Characteristic Peaks: |
|---|---|
| 156.5 | 920.6 |
| 252.6 | 1219.2 |
| 317.5 | 1320.7 |
| 382.3 | 1577.8 |
| 409.9 | 1607.4 |
| 443.9 | 2251.4 |
| 468.9 | |
| 491.3 | |
| 547.5 | |
| 631.1 | |
| 659.6 | |
| 669.9 | |
| 726.3 | |
| 768.8 | |
| 809.1 | |
| 821.4 | |
| 891.8 | |
| 920.6 | |
| 946.2 | |
| 976.8 | |
| 1056.0 | |
| 1106.1 | |
| 1136.1 | |
| 1155.7 | |
| 1219.2 | |
| 1271.7 | |
| 1301.2 | |
| 1320.7 | |
| 1353.6 | |
| 1379.9 | |
| 1418.1 | |
| 1446.3 | |
| 1512.8 | |
| 1532.3 | |
| 1577.8 | |
| 1607.4 | |
| 1647.7 | |
| 2251.4 | |
| 2732.9 | |
| 2939.0 | |
| 2968.1 | |
| 2987.7 | |
| 3057.9 | |

Fig. 47

| ζ | | η | |
|---|---|---|---|
| 1.94% water | ~12 moles of EtOH | 1% water | 0.3 moles of EtOH |
| 0.54% water | ~6 moles of EtOH | 2% water | 0.3 moles of EtOH |
| 11.25% water | ~1 mole of EtOH | 3% water | 0.6 mole of EtOH |

Fig. 51

ζ → Dry

| Condition | Time | Result |
|---|---|---|
| Nitrogen | ~ 25 min | æ |
|  | > 25 min | æ + è |
|  | >> 25 min | è |
| 40 °C | ~ 2 hrs | æ + è |
|  | ~ 6 hrs | Pattern A |
| vacuum, ambient | ~ 2 hrs | è |
|  | ~ 6 hrs | è dry |
| vacuum, ambient | ~ 2 hrs | ç like |
|  | 14 days | ç |
| vacuum, ambient | ~ 3.5 hrs | ç like |
| vacuum, 60 °C | ~ 2 hrs | è dry |
|  | ~ 6 hrs | è dry |

Fig. 52

| Condition | Time | Results | Wt change |
|---|---|---|---|
| 22% RH, ambient | ~2 hrs | ς shifted | 1% |
|  | ~6 hrs | ς shifted | 2% |
| 75% RH, ambient | ~2 hrs | ς shifted | 4% |
|  | ~6 hrs | ς shifted | 7% |
| 40 °C | ~2 hrs | ς | 1% |
|  | ~6 hrs | ς | 1% |
| 75% RH, 40 °C | ~2 hrs | ς shifted | 7% |
|  | ~6 hrs | ς shifted | 7% |
| vacuum, ambient | ~2 hrs | ς | -1% |
|  | ~6 hrs | ς | -1% |
|  | 1 week | ς | 0% |
| vacuum, 60 °C | ~2 hrs | ς | -1% |
|  | ~6 hrs | ς | -1% |
|  | 2 days | ς | -3% |
| grinding |  |  |  |
| compression | ~24 hrs |  |  |

ς 2% water content 0.3 moles of EtOH ⇧

⇧ 1% water content 0.3 moles of EtOH

Fig. 53

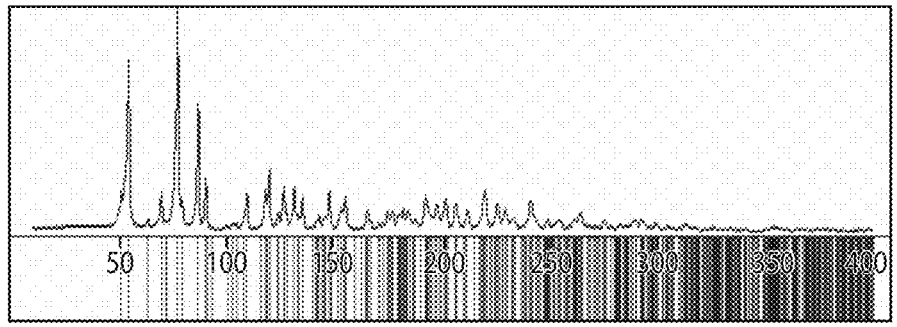

Indexing solution and derived quantities

| Form / Pattern | Rifaximin Form θ |
|---|---|
| Family and Space Group | Orthorhombic $P2_12_12_1$ (#19) |
| Z' / Z | 2 / 8 |
| a (Å) | 15.274 |
| b (Å) | 20.277 |
| c (Å) | 32.231 |
| α (deg) | 90 |
| β (deg) | 90 |
| γ (deg) | 90 |
| Volume (Å$^3$/cell) | 9982.3 |
| V/Z (Å$^3$/asym. unit) | 1247.8 |
| Assumed Composition[a] | $C_{43}H_{51}N_3O_{11}$, $xC_2H_6O$ $0 \leq x \leq 4$ |
| Density (g/cm$^3$)[a] | $1.05 \leq y \leq 1.29$ |
| Weight Fraction Solvent (%)[a] | $0 \leq z \leq 19.0$ |

[a]Density and weight fraction solvent are based on the assumed composition

Fig. 61

FORMS OF RIFAXIMIN AND USES THEREOF

RELATED APPLICATION

This application is a continuation of U.S. Ser. No. 13/152,804, filed Jun. 3, 2013, Allowed, which claims the benefit of U.S. Ser. No. 61/416,593, filed 23 Nov. 2010; U.S. Ser. No. 61/351,281, filed Jun. 3, 2010; U.S. Ser. No. 61/357,505, filed Jun. 22, 2010; U.S. Ser. No. 61/363,241, filed Jul. 10, 2010; U.S. Ser. No. 61/363,511; filed Jul. 12, 2010; and U.S. Ser. No. 61/367,185, filed Jul. 23, 2010, the entire contents of each of which are hereby incorporated by reference in their entirety.

BACKGROUND

Rifaximin (INN; see The Merck Index, XIII Ed., 8304) is an antibiotic belonging to the rifamycin class of antibiotics, e.g., a pyrido-imidazo rifamycin. Rifaximin exerts its broad antibacterial activity, for example, in the gastrointestinal tract against localized gastrointestinal bacteria that cause infectious diarrhea, irritable bowel syndrome, small intestinal bacterial overgrowth, Crohn's disease, and/or pancreatic insufficiency. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res,* 14 (2), 51-56, (1994)).

Rifaximin is described in Italian Patent IT 1154655 and EP 0161534, both of which are incorporated herein by reference in their entirety for all purposes. EP 0161534 discloses a process for rifaximin production using rifamycin O as the starting material (The Merck Index, XIII Ed., 8301). U.S. Pat. No. 7,045,620 B1 and PCT Publication WO 2006/094662 A1 disclose polymorphic forms of rifaximin.

SUMMARY

Described herein are polymorphic forms kappa (κ), theta (θ) and rifaximin:piperazine cocrystals (cocrystal 1 and cocrystal 2) of rifaximin that have not been previously described.

According to one aspect, the polymorphs and cocrystals described herein exhibit an X-ray powder diffraction pattern having characteristic peaks expressed in degrees 2θ (+/−0.20 degree θ or +/−0.1 degree θ, if so described) as described herein in the Figures and Tables. These polymorphs and cocrystals can also be characterized by unit cell volume as described herein. One of skill in the art would be able to determine major peaks and uniquely identifying peaks of the Rifaximin:piperazine cocrystals and of the polymorphs of rifaximin using the information set forth herein as well as the peak lists and XPRD patterns and data.

In one aspect, provided herein are Form kappa of rifaximin, Form theta of rifaximin, rifaximin:piperazine cocrystal 1 or rifaximin:piperazine cocrystal 2.

In one embodiment, the form of rifaximin kappa is characterized by an XRPD substantially similar to FIGS. 1, 2, 3, 10 and 16.

In one embodiment, the kappa form of rifaximin is characterized by a DSC or TGA Thermogram substantially similar to FIGS. 6, 7, 11, 12 and 13.

In one embodiment, the kappa form of rifaximin is characterized by the peaks listed in Table 3.

In one embodiment, the kappa form of rifaximin is characterized by the peaks listed in Table 4.

In one embodiment, the kappa form of rifaximin exhibits an X-ray powder diffraction pattern having characteristic peaks expressed in degrees 2θ (+/−0.10 degree θ) at (6.45-6.67)±0.20, (6.83-6.94)±0.20 and (7.68-7.78)±0.20; (6.45-6.67)±0.20, (6.83-6.94)±0.20 and (18.46-18.61)±0.20; (6.45-6.67)±0.20, (6.83-6.94)±0.20 and (7.52-7.56)±0.20; (6.83-6.94)±0.20, (7.68-7.78)±0.20 and (18.46-18.61)±0.20; (6.45-6.67)±0.20, (6.83-6.94)±0.20, (7.68-7.78)±0.20 and (18.46-18.61)±0.20; (6.83-6.94)±0.20, (7.52-7.56)±0.20, (7.68-7.78)±0.20 and (18.46-18.61)±0.20; (6.45-6.67)±0.20, (6.83-6.94)±0.20, (7.52-7.56)±0.20, (7.68-7.78)±0.20 and (18.46-18.61)±0.20; (6.45-6.67)±0.20, (6.83-6.94)±0.20, (7.52-7.56)±0.20, (7.68-7.78)±0.20, (8.30-8.34)±0.20 and (18.46-18.61)±0.20; or (5.41-5.65)±0.20, (6.45-6.67)±0.20, (6.83-6.94)±0.20, (7.52-7.56)±0.20, (7.68-7.78)±0.20, (8.30-8.34)±0.20 and (18.46-18.61)±0.20.

In one embodiment, the rifaximin:piperazine cocrystal 1 is characterized by an XRPD substantially similar to one or more of FIGS. 17, 18, 19, 20, 23, 30 and/or 48.

In one embodiment, the rifaximin:piperazine cocrystal 1 is characterized by IR spectra substantially similar to FIG. 21 and/or FIG. 33.

In one embodiment, the rifaximin:piperazine cocrystal 1 is characterized by Raman spectra substantially similar to FIG. 22, FIG. 35 and/or one or more peaks of FIG. 36.

In one embodiment, the rifaximin:piperazine cocrystal 1 exhibits an X-ray powder diffraction pattern having characteristic peaks expressed in degrees 2θ (+/−0.10 degree θ) comprising one or more peaks listed in FIG. 26.

In one embodiment, the rifaximin:piperazine cocrystal 1 exhibits an X-ray powder diffraction pattern having characteristic peaks expressed in degrees 2θ (+/−0.10 degree θ) comprising one or more peaks listed in FIG. 27.

In one embodiment, the rifaximin:piperazine cocrystal 1 exhibits an X-ray powder diffraction pattern having characteristic peaks expressed in degrees 2θ (+/−0.10 degree θ) at 5.74±0.10; 6.58±0.10; 7.49±0.10; 8.21±0.10; and 9.83±0.10.

In one embodiment, the rifaximin:piperazine cocrystal 1 exhibits an X-ray powder diffraction pattern having characteristic peaks expressed in degrees 2θ (+/−0.10 degree θ) at 5.74±0.10; 7.49±0.10; 8.21±0.10; and 9.83±0.10.

In one embodiment, the rifaximin:piperazine cocrystal 1 exhibits an X-ray powder diffraction pattern having characteristic peaks expressed in degrees 2θ (+/−0.10 degree θ) at 5.74±0.10; 6.58±0.10; 8.21±0.10; and 9.83±0.10.

In one embodiment, the rifaximin:piperazine cocrystal 1 exhibits an X-ray powder diffraction pattern having characteristic peaks expressed in degrees 2θ (+/−0.10 degree θ) at 5.74±0.10; 6.58±0.10; 7.49±0.10; and 9.83±0.10.

In one embodiment, the rifaximin:piperazine cocrystal 1 exhibits an X-ray powder diffraction pattern having characteristic peaks expressed in degrees 2θ (+/−0.10 degree θ) at 5.74±0.10; 6.58±0.10; 7.49±0.10; and 8.21±0.10.

In one embodiment, the rifaximin:piperazine cocrystal 1 characterized by DSC and TGA curves substantially similar to FIG. 28.

In one embodiment, the rifaximin:piperazine cocrystal 1 characterized by DVS curves substantially similar to FIG. 29.

In one embodiment, the rifaximin:piperazine cocrystal 1 characterized by NMR spectra substantially similar to FIG. 31.

In one embodiment, the rifaximin:piperazine cocrystal 1 characterized by SSNMR substantially similar to FIG. 32.

In one embodiment, the rifaximin:piperazine cocrystal 1 exhibiting IR spectrum peaks as shown in FIG. 34.

In one embodiment, the rifaximin:piperazine cocrystal comprises cocrystal 2.

In one embodiment, the rifaximin:piperazine cocrystal 2 is characterized by an XRPD substantially similar to one or more of FIGS. 19, 20, 37 and/or 39.

In one embodiment, the rifaximin:piperazine cocrystal 2 is characterized by IR spectra substantially similar to FIG. 21 and/or FIG. 44.

In one embodiment, the rifaximin:piperazine cocrystal 2 exhibiting IR spectrum peaks as shown in FIG. 45.

In one embodiment, the rifaximin:piperazine cocrystal 2 is characterized by Raman spectra substantially similar to FIG. 22, FIG. 46 and/or one or more peaks of FIG. 47.

In one embodiment, the rifaximin:piperazine cocrystal 2 exhibits an X-ray powder diffraction pattern having characteristic peaks expressed in degrees 2θ (+/−0.10 degree θ) comprising one or more peaks listed in FIG. 40.

In one embodiment, the rifaximin:piperazine cocrystal 2 exhibits an X-ray powder diffraction pattern having characteristic peaks expressed in degrees 2θ (+/−0.10 degree θ) comprising one or more peaks listed in FIG. 41.

In one embodiment, the rifaximin:piperazine cocrystal 2 exhibits an X-ray powder diffraction pattern having characteristic peaks expressed in degrees 2θ (+/−0.10 degree θ) at 3.64±0.10; 5.58±0.10; 6.45±0.10; 7.29±0.10; 7.60±0.10; 8.27±0.10; and 9.01±0.10.

In one embodiment, the rifaximin:piperazine cocrystal 2 exhibits an X-ray powder diffraction pattern having characteristic peaks expressed in degrees 2θ (+/−0.10 degree θ) at 5.58±0.10; 6.45±0.10; 7.29±0.10; 7.60±0.10; 8.27±0.10; and 9.01±0.10.

In one embodiment, the rifaximin:piperazine cocrystal 2 exhibits an X-ray powder diffraction pattern having characteristic peaks expressed in degrees 2θ (+/−0.10 degree θ) at 3.64±0.10; 6.45±0.10; 7.29±0.10; 7.60±0.10; 8.27±0.10; and 9.01±0.10.

In one embodiment, the rifaximin:piperazine cocrystal 2 exhibits an X-ray powder diffraction pattern having characteristic peaks expressed in degrees 2θ (+/−0.10 degree θ) at 3.64±0.10; 5.58±0.10; 7.29±0.10; 7.60±0.10; 8.27±0.10; and 9.01±0.10.

In one embodiment, the rifaximin:piperazine cocrystal 2 exhibits an X-ray powder diffraction pattern having characteristic peaks expressed in degrees 2θ (+/−0.10 degree θ) at 3.64±0.10; 5.58±0.10; 6.45±0.10; 7.60±0.10; 8.27±0.10; and 9.01±0.10.

In one embodiment, the rifaximin:piperazine cocrystal 2 exhibits an X-ray powder diffraction pattern having characteristic peaks expressed in degrees 2θ (+/−0.10 degree θ) at 3.64±0.10; 5.58±0.10; 6.45±0.10; 7.29±0.10; 7.60±0.10; and 9.01±0.10.

In one embodiment, the rifaximin:piperazine cocrystal 2 exhibits an X-ray powder diffraction pattern having characteristic peaks expressed in degrees 2θ (+/−0.10 degree θ) at 3.64±0.10; 5.58±0.10; 6.45±0.10; 7.29±0.10; 7.60±0.10; and 8.27±0.10.

In one embodiment, the rifaximin:piperazine cocrystal 2 exhibits an X-ray powder diffraction pattern having characteristic peaks expressed in degrees 2θ (+/−0.10 degree θ) at 3.64±0.10; 5.58±0.10; 6.45±0.10; 7.29±0.10; and 7.60±0.10.

In one embodiment, the rifaximin:piperazine cocrystal 2 characterized by DSC and TGA curves substantially similar to FIG. 42.

In one embodiment, the rifaximin:piperazine cocrystal 2 characterized by NMR spectra substantially similar to FIG. 43.

In one embodiment, the Form kappa of rifaximin, the Form theta, a rifaximin:piperazine cocrystal 1 and/or the rifaximin:piperazine cocrystal 2 contain less than 5% by weight total impurities.

In one embodiment, the Form kappa of rifaximin, the Form theta of rifaximin, rifaximin:piperazine cocrystal 1 and/or the rifaximin:piperazine cocrystal 2 is at least 50% pure, or at least 75% pure, or at least 80% pure, or at least 90% pure, or at least 95% pure, or at least 98% pure.

In one embodiment, the Form kappa of rifaximin, the Form theta of rifaximin, the rifaximin:piperazine cocrystal 1 and/or the rifaximin:piperazine cocrystal 2 further comprise a pharmaceutically acceptable carrier.

In one embodiment, the Form kappa of rifaximin, the Form theta of rifaximin, the rifaximin:piperazine cocrystal 1 and/or the rifaximin:piperazine cocrystal 2 are formulated as coated or uncoated tablets, hard or soft gelatin capsules, sugar-coated pills, lozenges, wafer sheets, pellets or powders in sealed packets.

Provided herein are processes for producing Form Kappa of rifaximin comprising one or more of the methods listed in Table 1 or Table 2.

In one embodiment, provided is a method for producing Form Kappa or rifaximin comprising the steps of agitating Form α of rifaximin below 60° C. until a precipitate results and filtering said precipitate. In one embodiment, the agitation is stirring. In one embodiment, the agitation is sonication. In one embodiment, the temperature is room temperature. In one embodiment, the agitation is stirring and the temperature is above room temperature but below 60° C. In one embodiment, the agitation is sonication and the temperature is room temperature. In one embodiment, the filtered precipitate is further dried (e.g., over $P_2O_5$).

Provided herein are processes for producing rifaximin:piperazine cocrystals comprising one or more of the methods listed in Table 9.

In one embodiment, the composition further comprises one or more pharmaceutically acceptable excipients. The excipients may be one or more of a diluting agent, binding agent, lubricating agent, disintegrating agent, coloring agent, flavoring agent or sweetening agent.

According to one embodiment, the pharmaceutical composition may be formulated as coated or uncoated tablets, hard or soft gelatin capsules, sugar-coated pills, lozenges, wafer sheets, pellets or powders in a sealed packet. In a related embodiment, the pharmaceutical composition may also be formulated for topical use.

According to another aspect, provided herein are methods of treating, preventing or alleviating a bowel related disorder comprising administering to a subject in need thereof an effective amount of one or more of Form kappa of rifaximin, rifaximin:piperazine cocrystal 1 and/or rifaximin:piperazine cocrystal 2 of rifaximin.

According to another aspect, provided herein are methods of treating, preventing or alleviating a bowel related disorder comprising administering to a subject in need thereof an effective amount of one or more of a Form kappa of rifaximin, the rifaximin:piperazine cocrystal 1 and/or the rifaximin:piperazine cocrystal 2.

In one embodiment, the subject is suffering from at least one bowel related disorder selected from the group consisting of irritable bowel syndrome, travelers' diarrhea, small intestinal bacterial overgrowth, Crohn's disease, chronic pancreatitis, pancreatic insufficiency, hepatic encephalopathy, minimal hepatic encephalopathy, diverticulitis, enteritis and colitis.

Provided herein, according to one aspect, are processes for producing Form kappa of rifaximin, Form theta of rifaximin, or rifaximin:piperazine cocrystals 1 and/or 2. Methods are outlined in the Examples and in the Tables infra.

Provided herein, according to one aspect, are kits for treating a bowel disorder in a subject, comprising one or more of the Form kappa of rifaximin, the Form theta of rifaximin, the rifaximin:piperazine cocrystal 1 and/or the rifaximin:piperazine cocrystal 2 of rifaximin and instructions for use.

Provided herein, according to one aspect, are packaged compositions comprising, a therapeutically effective amount of one or more of the Form kappa of rifaximin, the Form theta of rifaximin, the rifaximin:piperazine cocrystal 1 and/or the rifaximin:piperazine cocrystal 2 of rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

In one aspect, a pharmaceutical composition is presented, which comprises one or more of the Form kappa of rifaximin, the Form theta of rifaximin, the rifaximin:piperazine cocrystal 1 and/or the rifaximin:piperazine cocrystal 2 of rifaximin and a pharmaceutically acceptable carrier.

In one embodiment, the pharmaceutical composition further comprises excipients.

According to another embodiment, the excipients are one or more of a diluting agent, binding agent, lubricating agent, disintegrating agent, coloring agent, flavoring agent or sweetening agent.

In another embodiment, the composition is formulated for selected coated and uncoated tablets, hard and soft gelatin capsules, sugar-coated pills, lozenges, wafer sheets, pellets and powders in sealed packets.

In one embodiment, the composition is formulated for topical use.

Presented herein, according to one aspect, are methods of treating, preventing, or alleviating a bowel related disorder comprising administering to a subject in need thereof a cell infected with a virus with an effective amount of one or more forms of rifaximin.

According to another embodiment, wherein the bowel related disorder is one or more of irritable bowel syndrome, travelers' diarrhea, small intestinal bacterial overgrowth, Crohn's disease, chronic pancreatitis, pancreatic insufficiency, hepatic encephalopathy, minimal hepatic encephalopathy, diverticulitis, enteritis and colitis.

Also presented herein, according to one aspect are packaged compositions comprising a therapeutically effective amount of one or more of Form kappa of rifaximin, the Form theta of rifaximin, the rifaximin:piperazine cocrystal 1 and/or the rifaximin:piperazine cocrystal 2 and a pharmaceutically acceptable carrier or diluents, wherein the composition is formulated for treating a subject suffering from or susceptible to a bowel disorder, and packaged with instructions to treat a subject suffering from or susceptible to a bowel disorder.

Also presented herein is the use of one or more of Form kappa of rifaximin, the Form theta of rifaximin, the rifaximin:piperazine cocrystal 1 and/or the rifaximin:piperazine cocrystal 2 of rifaximin as a medicament.

Presented herein, according to another aspect, is a process for producing a rifaximin:piperazine cocrystal 1 comprising dissolving rifaximin in acetonitrile with sonication; adding resulting solution to piperazine with stirring.

In one embodiment, the method may further comprise adding additional acetonitrile to the piperazine solution.

In one embodiment, the method may further comprise continuing to stir the piperazine solution for from between 1 hour and 3 days.

In one embodiment, the stirring is at ambient temperatures.

In one embodiment, the method may further comprise collecting solids by filtration.

In one embodiment, the method may further comprise drying the collected solids.

Presented herein, according to another aspect, is a process for producing a rifaximin:piperazine cocrystal 2 comprising exposing rifaximin:piperazine cocrystal 1 to acetonitrile vapors.

Presented herein in one aspect is rifaximin form theta. In one embodiment, the form theta of rifaximin is characterized by an XRPD substantially similar to FIG. 60, 67 or 72. In one embodiment, form theta of rifaximin comprises one or more of the peaks identified in FIG. 68. In one embodiment, form theta of rifaximin comprises a DSC substantially similar to FIG. 70. In one embodiment, form theta of rifaximin comprises a TGA substantially similar to FIG. 70. In one embodiment, form theta of rifaximin comprises a moisture sorption XRPD substantially similar to FIG. 71. In one embodiment, form theta of rifaximin comprises a post-moisture sorption XRPD substantially similar to FIG. 72.

In one embodiment, form theta of rifaximin comprises one or more of the peaks identified in Table 24. In one embodiment, form theta of rifaximin comprises one or more of the peaks identified in Table 25.

In one embodiment, the theta form of rifaximin exhibits an X-ray powder diffraction pattern having one or more of the following characteristic peaks expressed in degrees 2θ (+/−0.10 degree θ) at 5.48±0.10, 7.00±0.10, 7.75±0.10, 8.72±0.10, 9.09±0.10, or 10.96±0.10. In one embodiment, the theta form of rifaximin exhibits an X-ray powder diffraction pattern having characteristic peaks expressed in degrees 2θ (+/−0.10 degree θ) at 5.48±0.10, 7.00±0.10, 7.75±0.10, 8.72±0.10, 9.09±0.10, and 10.96±0.10; or 5.48±0.10, 7.00±0.10, 7.75±0.10, or 5.48±0.10, 7.75±0.10, and 8.72±0.10; or 5.48±0.10, 7.00±0.10, and 8.72±0.10; or 5.48±0.10, 8.72±0.10, and 9.09±0.10; or 5.48±0.10, 9.09±0.10, and 10.96±0.10; or 7.75±0.10, 8.72±0.10, and 9.09±0.10; or 7.00±0.10, 7.75±0.10, 8.72±0.10, and 10.96±0.10; or 8.72±0.10, 9.09±0.10, and 10.96±0.10; or 7.00±0.10, 7.75±0.10, 8.72±0.10, and 10.96±0.10; or 7.00±0.10, 8.72±0.10, and 10.96±0.10.

Presented herein in one aspect are methods of making rifaximin form eta.

Presented herein in one aspect are methods of making rifaximin form iota.

In one aspect, provided herein are methods of making rifaximin form eta, comprising: precipitating rifaximin from ethanol; drying the precipitated rifaximin under nitrogen; and maintaining the precipitated rifaximin at an elevated temperature for 30 minutes or longer.

In one embodiment the form precipitated comprises form zeta.

In one embodiment, the maintaining is at about 40° C. for about 2 hours or longer.

In one embodiment, the maintaining is under vacuum at about 60° C. for 2 hours or longer.

In one embodiment, the drying is for about 10 minutes or less.

In one aspect, provided herein are methods of making rifaximin form iota, comprising: precipitating rifaximin from ethanol; drying the precipitated rifaximin under nitrogen; and maintaining the rifaximin at ambient temperature.

In one embodiment the form precipitated comprises form zeta.

In one embodiment, the maintaining further comprises the rifaximin under vacuum for 6 or more hours.

In one embodiment, the maintaining further comprises the rifaximin at between about 22% and 50% humidity.

In one embodiment, the drying is for about 10 minutes or less.

In one aspect, provided herein are methods of making Form iota and Form theta mixtures, comprising precipitating rifaximin from ethanol; drying the precipitated rifaximin under nitrogen; and maintaining the rifaximin at from between about 10% RH to about 46% relative humidity (RH) at ambient temperatures from at least one hour to about 6 hours or longer. In other embodiments, the drying is for about 10 minutes or less.

Also presented herein are methods of making Form theta of rifaximin, comprising precipitating Form zeta of rifaximin from ethanol and drying under nitrogen from between 10 seconds and 10 minutes.

Other embodiment and aspects are disclosed infra.

BRIEF DESCRIPTION OF THE DRAWINGS

FIG. 26 is a list of observed XRPD peaks for Rifaximin:piperazine cocrystal 1.

FIG. 34 is a list of observed IR peaks for Rifaximin:piperazine cocrystal 1.

FIG. 36 is a list of observed Raman peaks for Rifaximin:piperazine cocrystal 1.

FIG. 40 is a list of observed XRPD peaks for Rifaximin: piperazine cocrystal 2.

FIG. 45 is an observed and Characteristic IR peaks for Rifaximin:piperazine cocrystal 2.

FIG. 47 is a list of observed and characteristic Raman peaks for Rifaximin:piperazine cocrystal 2.

FIG. 51 shows the conversion of rifaximin form ζ to rifaximin form η.

FIG. 52 shows the generation of rifaximin form η.

FIG. 53 shows the effect of stress on rifaximin form η.

FIG. 61 shows indexing solution of rifaximin Form θ. The bars indicate the allowed reflections based on the unit cell dimensions and the assigned space group (P2$_1$2$_1$2$_1$, #19).

DETAILED DESCRIPTION

Figure 1:
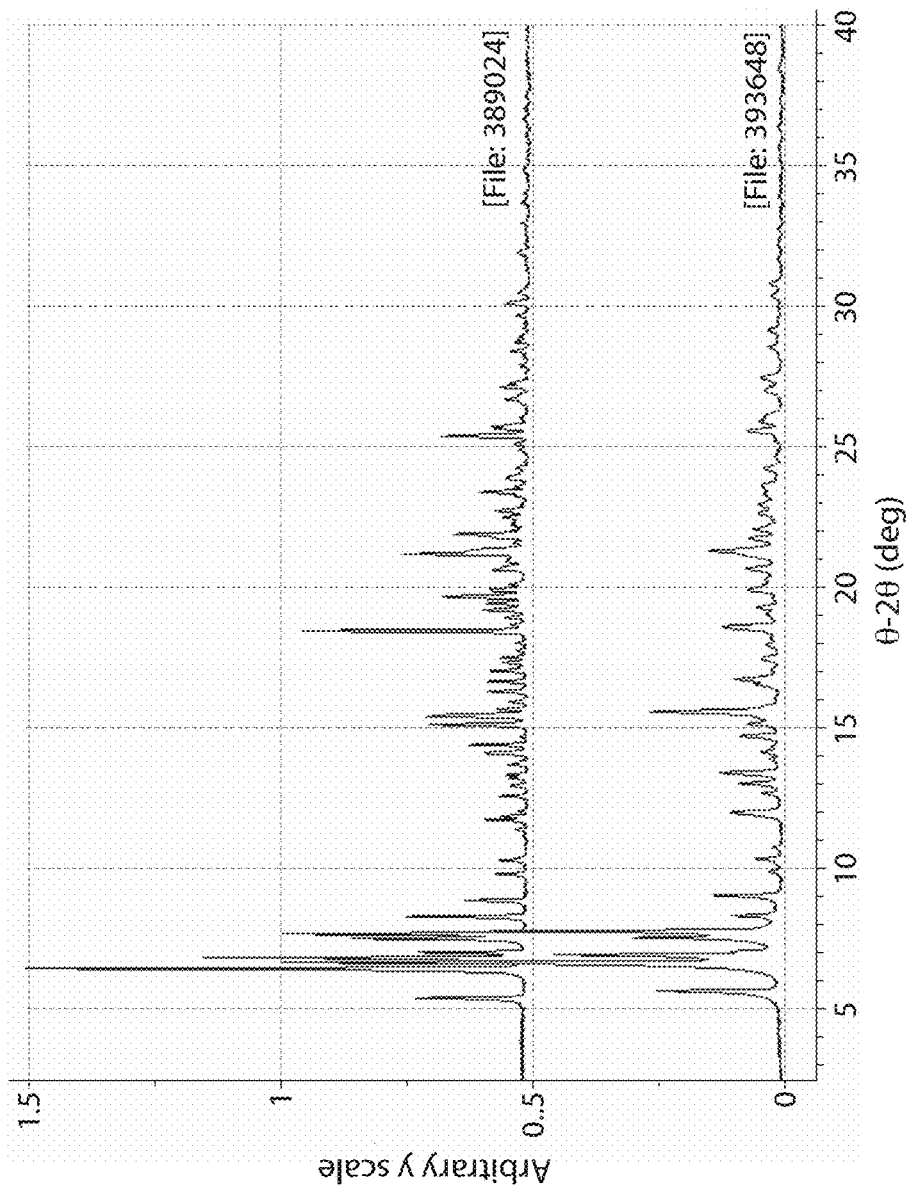
FIG. 1 shows XRPD patterns of rifaximin Form κ. The top XRPD pattern is as prepared. The bottom XRPD pattern is after drying over $P_2O_5$ at room temperature.

Embodiments described herein relate to the discovery of new polymorphic and cocrystal forms of rifaximin and the use of those forms as antibiotics. In one embodiment the use of one or more of Form kappa of rifaximin, Form theta of rifaximin, rifaximin:piperazine cocrystal 1 and/or rifaximin: piperazine cocrystal 2 (FIGS. 1-72) of the antibiotic known as Rifaximin (INN), in the manufacture of medicinal preparations for the oral or topical route is contemplated. Embodiments described herein also relate to administration of such medicinal preparations to a subject in need of treatment with antibiotics.

Rifaximin is a compound of the rifamycin class of antibiotics. Rifaximin is a compound having the structure of Formula I:

(I)

As used herein, "rifaximin Form kappa," "Form kappa," "Form kappa of rifaximin," "kappa form of rifaximin," "polymorph kappa," and "rifaximin kappa" and variations thereof are used interchangeably to denote the polymorphic form of rifaximin as further described herein by, for example, one or more peaks of an x-ray diffractogram, differential scanning calorimetry data. Form kappa comprises an x-ray powder diffraction pattern peak positions listed in Table 2 and 3 below and in the Examples and Figures.

As used herein, "rifaximin Form theta," "Form theta," "Form theta of rifaximin," "theta form of rifaximin," "polymorph theta," and "rifaximin theta" and variations thereof are used interchangeably to denote the polymorphic form of rifaximin as further described herein by, for example, one or more peaks of an x-ray diffractogram, differential scanning calorimetry data shown infra in the Tables, Examples and Figures.

As used herein, "rifaximin:piperazine cocrystal 1" and "rifaximin:piperazine cocrystal 2" and variations thereof are used to denote the cocrystal form of rifaximin as further described herein by, for example, one or more peaks of an x-ray diffractogram, differential scanning calorimetry data shown infra in the Tables, Examples and Figures. Together, the cocrystals may be referred to herein as rifaximin:piperazine cocrystals.

As used herein, the term polymorph is occasionally used as a general term in reference to the forms of rifaximin and includes within the context, salt, hydrate, polymorph co-crystal and amorphous forms of rifaximin. This use depends on context and will be clear to one of skill in the art.

As used herein, the term "about" when used in reference to x-ray powder diffraction pattern peak positions refers to the inherent variability of the peaks depending on, for example, the calibration of the equipment used, the process used to produce the polymorph, the age of the crystallized material and the like, depending on the instrumentation used. In this case the measure variability of the instrument was about +0.2 degrees 2-θ. A person skilled in the art, having the benefit of this disclosure, would understand the use of "about" in this context. The term "about" in reference to other defined parameters, e.g., water content, $C_{max}$, $t_{max}$, AUC, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word about.

As used herein, "similar" in reference to a form exhibiting characteristics similar to, for example, an XRPD, an IR, a Raman spectrum, a DSC, TGA, NMR, SSNMR, etc, indicates that the polymorph or cocrystal is identifiable by that method and could range from similar to substantially similar, so long as the material is identified by the method with variations expected by one of skill in the art according to the experimental variations, including, for example, instruments used, time of day, humidity, season, pressure, room temperature, etc.

Polymorphism, as used herein, refers to the occurrence of different crystalline forms of a single compound in distinct hydrate status, e.g., a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as solubility profiles, melting point temperatures, hygroscopicity, particle shape, density, flowability, compactibility and/or x-ray diffraction peaks. The solubility of each polymorph may vary, thus, identifying the existence of pharmaceutical polymorphs is essential for providing pharmaceuticals with predictable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, Pharm Manuf. 3, 33 (1986); J. K. Haleblian and W. McCrone, J. Pharm. Sci., 58, 911 (1969); and J. K. Haleblian, J. Pharm. Sci., 64, 1269 (1975), all of which are incorporated herein by reference.

As used herein, "subject" includes organisms which are capable of suffering from a bowel disorder or other disorder treatable by rifaximin or who could otherwise benefit from the administration of a rifaximin as described herein, such as human and non-human animals. Preferred human animals include human subjects. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to a bowel disorder is meant to include subjects at risk of developing a bowel disorder infection, e.g., subjects suffering from one or more of an immune suppression, subjects that have been exposed to other subjects with a bacterial infection, physicians, nurses, subjects traveling to remote areas known to harbor bacteria that causes travelers' diarrhea, subjects who drink amounts of alcohol that damage the liver, subjects with a history of hepatic dysfunction, etc.

The language "a prophylactically effective amount" of a compound refers to an amount of a compound of the invention of formula (I) or otherwise described herein which is effective, upon single or multiple dose administration to the subject, in preventing or treating a bacterial infection.

The language "therapeutically effective amount" of a compound of the invention refers to an amount of an agent which is effective, upon single or multiple dose administration to the subject to provide a therapeutic benefit to the subject. In one embodiment, the therapeutic benefit is inhibiting a virus, or in prolonging the survivability of a subject with such a viral infection. In another embodiment, the therapeutic benefit is inhibiting a bacterial infection or prolonging the survival of a subject with such a bacterial infection beyond that expected in the absence of such treatment.

Rifaximin exerts a broad antibacterial activity in the gastrointestinal tract against localized gastrointestinal bacteria that cause infectious diarrhea, including anaerobic strains. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res*, 14 (2), 51-56, (1994)).

In respect to possible adverse events coupled to the therapeutic use of rifaximin, the induction of bacterial resistance to the antibiotics is of particular relevance.

From this point of view, any differences found in the systemic absorption of the forms of rifaximin disclosed herein may be significant, because at sub-inhibitory concentration of rifaximin, such as in the range from 0.1 to 1 µg/ml, selection of resistant mutants has been demonstrated to be possible (Marchese A. et al. *In vitro activity of rifaximin, metronidazole and vancomycin against clostridium difficile and the rate of selection of spontaneously resistant mutants against representative anaerobic and aerobic bacteria, including ammonia-producing species. Chemotherapy*, 46(4), 253-266, (2000)).

Polymorphs of rifaximin have been found to have differing in vivo bioavailability properties. Thus, the polymorphs disclosed herein would be useful in the preparation of pharmaceuticals with different characteristics for the treatment of infections. This would allow generation of rifaximin preparations that have significantly different levels of adsorption with $C_{max}$ values from about 0.0 ng/ml to 5.0 µg/ml. This leads to preparation of rifaximin compositions that are from negligibly to significantly adsorbed by subjects undergoing treatment. One embodiment of the invention is modulating the therapeutic action of rifaximin by selecting the proper polymorphic form, or mixture of forms, for treatment of a patient. For example, in the case of invasive bacteria, the most bioavailable polymorphic form can be selected from those disclosed herein, whereas in case of non-invasive pathogens less adsorbed forms of rifaximin can be selected, since they may be safer for the subject undergoing treatment. Form of rifaximin may determine solubility, which may also determine bioavailability.

The above-mentioned forms disclosed herein can be advantageously used as pure and homogeneous products in the manufacture of medicinal preparations containing rifaximin.

For XRPD analysis, accuracy and precision associated with third party measurements on independently prepared samples on different instruments may lead to variability which is greater than ±0.1° 2Θ. For d-space listings, the wavelength used to calculate d-spacings was 1.541874 Å, a weighted average of the Cu—Kα1 and Cu—Kα2 wavelengths. Variability associated with d-spacing estimates was calculated from the USP recommendation, at each d-spacing, and provided in the respective data tables and peak lists.

Methods of Treatment

Provided herein are methods of treating, preventing, or alleviating bowel related disorders comprising administering to a subject in need thereof an effective amount of one or more of the Form kappa of rifaximin, the rifaximin:piperazine cocrystal 1 and/or the rifaximin:piperazine cocrystal 2. Bowel related disorders include one or more of irritable bowel syndrome, diarrhea, microbe associated diarrhea, *Clostridium difficile* associated diarrhea, travelers' diarrhea, small intestinal bacterial overgrowth, Crohn's disease, diverticular disease, chronic pancreatitis, pancreatic insufficiency, enteritis, colitis, hepatic encephalopathy, minimal hepatic encephalopathy or pouchitis. Topical skin infections and vaginal infections may also be treated with the rifaximin forms described herein.

The length of treatment for a particular bowel disorder will depend in part on the disorder. For example, travelers' diarrhea may only require treatment duration of 12 to about 72 hours, while Crohn's disease may require treatment durations from about 2 days to 3 months. Dosages of rifaximin will also vary depending on the diseases state. Proper dosage ranges are provided herein infra. The polymorphs and cocrystals described herein may also be used to treat or prevent a pathology in a subject suspected of being exposed to a biological warfare agent.

The identification of those subjects who are in need of prophylactic treatment for bowel disorder is well within the ability and knowledge of one skilled in the art. Certain of the methods for identification of subjects which are at risk of developing a bowel disorder which can be treated by the subject method are appreciated in the medical arts, such as family history, travel history and expected travel plans, the presence of risk factors associated with the development of that disease state in the subject. A clinician skilled in the art can readily identify such candidate subjects, by the use of, for example, clinical tests, physical examination and medical/family/travel history.

In yet another aspect, a method of treating a subject suffering from or susceptible to a bowel disorder comprises administering to a subject in need thereof a therapeutically effective amount of one or more rifaximin polymorphs and co-crystals described herein, to thereby treat the subject. Upon identification of a subject suffering from or susceptible to a bowel disorder, for example, IBS, one or more rifaximin polymorphs and/or cocrystals are administered.

Pharmaceutical Preparations

Embodiments also provide pharmaceutical compositions, comprising an effective amount of one or more rifaximin polymorphs and co-crystals described herein (e.g., described herein and a pharmaceutically acceptable carrier. In a further embodiment, the effective amount is effective to treat a bacterial infection, e.g., small intestinal bacterial overgrowth, Crohn's disease, hepatic encephalopathy, antibiotic associated colitis, and/or diverticular disease. Embodiments also provide pharmaceutical compositions, comprising an effective amount of one or more rifaximin polymorphs described herein in combination with one or more previously known polymorphs of rifaximin (e.g., alpha, beta, gamma, delta, epsilon, iota, zeta, eta and amorphous).

For examples of the use of rifaximin to treat Travelers' diarrhea, see Infante R M, Ericsson C D, Zhi-Dong J, Ke S, Steffen R, Riopel L, Sack D A, DuPont, H L. Enteroaggregative *Escherichia coli* Diarrhea in Travelers: Response to Rifaximin Therapy. *Clinical Gastroenterology and Hepatology*. 2004; 2:135-138; and Steffen R, M.D., Sack D A, M.D., Riopel L, PhD, Zhi-Dong J, Ph.D., Sturchler M, M.D., Ericsson C D, M.D., Lowe B, M. Phil., Waiyaki P, Ph.D., White M, Ph.D., DuPont H L, M.D. Therapy of Travelers' Diarrhea With Rifaximin on Various Continents. *The American Journal of Gastroenterology*. May 2003, Volume 98, Number 5, all of which are incorporated herein by reference in their entirety. Examples of treating hepatic encephalopathy with rifaximin see, for example, N. Engl J. Med. 2010 362 1071-1081.

Embodiments also provide pharmaceutical compositions comprising one or more of the Form kappa of rifaximin, the rifaximin:piperazine cocrystal 1 and/or the rifaximin:piperazine cocrystal 2 and a pharmaceutically acceptable carrier. That is, formulations may contain only one polymorph or cocrystal or may contain a mixture of more than one polymorph or cocrystal. Mixtures may be selected, for example on the basis of desired amounts of systemic adsorption, dissolution profile, desired location in the digestive tract to be treated, and the like. Embodiments of the pharmaceutical composition further comprise excipients, for example, one or more of a diluting agent, binding agent, lubricating agent, disintegrating agent, coloring agent, flavoring agent or sweetening agent. One composition may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In an embodiment, the rifaximin polymorph is administered to the subject using a pharmaceutically-acceptable formulation, e.g., a pharmaceutically-acceptable formulation that provides sustained delivery of the rifaximin polymorph to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those rifaximin polymorphs and cocrystals of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is preferably "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a rifaximin forms disclosed herein include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred %, this amount will range from about 1% to about ninety-nine % of active ingredient, preferably from about 5% to about 80%, or from about 10% to about 60%.

Methods of preparing these compositions include the step of bringing into association a rifaximin polymorph(s) and cocrystals with the carrier and, optionally, one or more accessory ingredients. In general, the formulations are prepared by uniformly and intimately bringing into association a rifaximin polymorph with liquid carriers, or finely divided solid carriers, or both, and then, if necessary, shaping the product.

Compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a rifaximin polymorph(s) and cocrystals as an active ingredient. A compound may also be administered as a bolus, electuary or paste.

The forms of rifaximin disclosed herein can be advantageously used in the production of medicinal preparations having antibiotic activity, containing rifaximin, for both oral and topical use. The medicinal preparations for oral use will contain one or more forms of rifaximin together with the usual excipients, for example diluting agents such as mannitol, lactose and sorbitol; binding agents such as starches, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starches, celluloses, alginates, gums and reticulated polymers; coloring, flavoring and sweetening agents.

Embodiments of the invention include solid preparations administrable by the oral route, for instance coated and uncoated tablets, of soft and hard gelatin capsules, sugar-coated pills, lozenges, wafer sheets, pellets and powders in sealed packets or other containers.

Medicinal preparations for topical use can contain one or more forms of rifaximin together with usual excipients, such as white petrolatum, white wax, lanoline and derivatives thereof, stearylic alcohol, propylene glycol, sodium lauryl sulfate, ethers of fatty polyoxyethylene alcohols, esters of fatty polyoxyethylene acids, sorbitan monostearate, glyceryl monostearate, propylene glycol monostearate, polyethylene glycols, methylcellulose, hydroxymethyl propylcellulose, sodium carboxymethylcellulose, colloidal aluminium and magnesium silicate, sodium alginate.

Embodiments of the invention relate to all of the topical preparations, for instance ointments, pomades, creams, gels and lotions.

In solid dosage forms of rifaximin for oral administration (capsules, tablets, pills, dragees, powders, granules and the like), the active ingredient is typically mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the rifaximin polymorph(s) and cocrystals include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active rifaximin polymorph(s) and cocrystals may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions for rectal or vaginal administration may be presented as a suppository, which may be prepared by mixing one or more rifaximin polymorph(s) and cocrystals with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions which are suitable for vaginal administration also include pessaries, tampons, creams, gels, pastes, foams or spray formulations containing such carriers as are known in the art to be appropriate.

Dosage forms for the topical or transdermal administration of a rifaximin polymorph(s) and cocrystals include powders, sprays, ointments, pastes, creams, lotions, gels, solutions, patches and inhalants. The active rifaximin polymorph(s) and cocrystals may be mixed under sterile conditions with a pharmaceutically-acceptable carrier, and with any preservatives, buffers, or propellants which may be required.

Ointments, pastes, creams and gels may contain, in addition to rifaximin polymorph(s) and cocrystals, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a rifaximin polymorph(s) and cocrystals, excipients such as lactose, talc, silicic acid, aluminium hydroxide, calcium silicates and polyamide powder, or mixtures of these substances. Sprays can additionally contain customary propellants, such as chlorofluorohydrocarbons and volatile unsubstituted hydrocarbons, such as butane and propane.

The rifaximin polymorph(s) and cocrystals can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

An aqueous aerosol is made, for example, by formulating an aqueous solution or suspension of the agent together with conventional pharmaceutically-acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a rifaximin polymorph(s) and cocrystals to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions suitable for parenteral administration may comprise one or more rifaximin polymorph(s) and cocrystals in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, to prolong the effect of a drug, it is desirable to alter the absorption of the drug. This may be accomplished by the use of a liquid suspension of crystalline, salt or amorphous material having poor water solubility. The rate of absorption of the drug may then depend on its rate of dissolution which, in turn, may depend on crystal size and crystalline form. Alternatively, delayed absorption of a drug form is accomplished by dissolving or suspending the drug in an oil vehicle.

Injectable depot forms are made by forming microencapsule matrices of rifaximin polymorph(s) and cocrystals in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the rifaximin polymorph(s) and cocrystals are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the rifaximin polymorph(s) and cocrystals, which may be used in a suitable hydrated form, and/or the pharmaceutical compositions of the present invention, are formulated into pharmaceutically-acceptable dosage forms by methods known to those of skill in the art.

Actual dosage levels and time course of administration of the active ingredients in the pharmaceutical compositions may be varied so as to obtain an amount of the active ingredient which is effective to achieve the desired therapeutic response for a particular subject, composition, and mode of administration, without being toxic to the subject. An exemplary dose range is from 25 to 3000 mg per day. Other doses include, for example, 600 mg/day, 1100 mg/day and 1650 mg/day. Other exemplary doses include, for example, 1000 mg/day, 1500 mg/day, from between 500 mg to about 1800 mg/day or any value in-between.

A preferred dose of the rifaximin polymorph or cocrystals disclosed herein is the maximum that a subject can tolerate without developing serious side effects. Preferably, the rifaximin polymorph of the present invention is administered at a concentration of about 1 mg to about 200 mg per kilogram of body weight, about 10 to about 100 mg/kg or about 40 mg to about 80 mg/kg of body weight. Ranges intermediate to the above-recited values are also intended to be part. For example, doses may range from 50 mg to about 2000 mg/day.

In combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment in which another therapeutic agent is administered to an animal, the effective amount of the compound of this invention is less than its effective amount in case the other therapeutic agent is not administered. In another embodiment, the effective amount of the conventional agent is less than its effective amount in case the compound of this invention is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same subject's visit.

In certain embodiments, one or more compounds and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same compounds may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a rifaximin polymorph may be repeated and the administration may be separated by at least 1 day, 2 days, 3 days, 5 days, 10 days, 15 days, 30 days, 45 days, 2 months, 75 days, 3 months, or at least 6 months.

Certain indications may require longer treatment times. For example, travelers' diarrhea treatment may only last from between about 12 hours to about 72 hours, while a treatment for Crohn's disease may be from between about 1 day to about 3 months. A treatment for hepatic encephalopathy may be, for example, for the remainder of the subject's life span. A treatment for IBS may be intermittent for weeks or months at a time or for the remainder of the subject's life.

Article of Manufacture

Another embodiment includes articles of manufacture that comprise, for example, a container holding a pharmaceutical composition suitable for oral or topical administration of rifaximin in combination with printed labeling instructions providing a discussion of when a particular dosage form should be administered with food and when it should be taken on an empty stomach. Exemplary dosage forms and administration protocols are described infra. The composition will be contained in any suitable container capable of holding and dispensing the dosage form and which will not significantly interact with the composition and will further be in physical relation with the appropriate labeling. The labeling instructions will be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

Another aspect is an article of manufacture that comprises a container containing a pharmaceutical composition comprising rifaximin wherein the container holds preferably rifaximin composition in unit dosage form and is associated with printed labeling instructions advising of the differing absorption when the pharmaceutical composition is taken with and without food.

Packaged compositions are also provided, and may comprise a therapeutically effective amount of rifaximin. Rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

Kits are also provided herein, for example, kits for treating a bowel disorder in a subject. The kits may contain, for example, one or more of the Form kappa of rifaximin, the rifaximin:piperazine cocrystal 1 and/or the rifaximin:piperazine cocrystal 2 of rifaximin and instructions for use. The instructions for use may contain proscribing information, dosage information, storage information, and the like.

Packaged compositions are also provided, and may comprise a therapeutically effective amount of one or more of a polymorph of rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

EXAMPLES

Example 1

Form κ

Form κ is a variable solvate with unit cell structure capable of expanding and/or shrinking to accommodate different amounts of IPA. Form Kappa (κ) was obtained by dissolving Form Alpha (α) in isopropanol at loadings ranging from 57 to 197 mg/mL followed by mechanical agitation.

Form κ is identified as a variable system of which the unit cell parameters may change via expansion or contraction to accommodate the solvent. XRPD peak positions are a direct result of the unit cell parameters, and therefore one single XRPD pattern may not be representative of the crystal Form. Multiple XRPD patterns obtained on various samples suggest that a range exist for the reflection peaks observed in Form κ. Indexing solutions were obtained on two representative XRPD patterns of Form κ but do not necessarily indicate the upper and lower limit of the range. Rather they should be considered two discrete examples of the Form κ series. Theoretical calculation from the indexing solutions indicates that Form κ may be able to accommodate up to 4 moles of IPA per mole of rifaximin based on the void space within the unit cell. One sample contains two moles of IPA per mole of rifaximin and negligible amount of water by $^1$H-NMR and Karl-Fischer titration. Another sample, with the unit cell volume being smaller by about 75 $Å^3$ contains 0.4 mole of IPA per mole of rifaximin and 0.76 wt % of water.

Preparation and Drying Studies

Preparation

Form κ can be prepared from isopropanol (IPA, see Table 1).

TABLE 1

Preparation of Rifaximin Form κ

| Rifaximin (mg) | IPA (mL) | Condition | Observation | XRPD result |
|---|---|---|---|---|
| 108.5 | 0.55 | Sonication/RT | Orange solid, B/E | κ |
| 88 | 0.5 | Sonication/RT | Orange plates, B/E | κ |
| 93.6 | 0.5 | Stirring/heat | Mixture of orange and red solid, B/E | κ |
| 56.5 | 1 | Stirring/heat | Orange solid, B/E | κ |
| 57.7 | 1 | Stirring/heat | Orange solid, B/E | κ |
| 24237.9 | 130 | Stirring | Yellow solid | κ |

$^a$RT = room temperature; heat = set hotplate to 60° C. while the actual temperature of sample may be lower;
$^b$B = birefringent; E = extinction.

IPA was added to rifaximin Form α at loadings from 57 to 197 mg/mL. To facilitate the dissolution of solid, mechanical agitation was applied either by sonication at room temperature or by magnetic stirring at slightly elevated temperature (e.g., below 60° C.). Under both conditions, Form κ precipitated out from the isopropanol solution and was subsequently isolated by vacuum filtration. The material stored at ambient appeared birefringent with extinction under polarized light microscope.

Details of each experiment are presented in Table 1. For example, one sample was prepared by adding 0.55 mL IPA into a 2-dram vial containing 108.5 mg of Form α. A red solution, as well as some undissolved solids were observed. The vial was then sonicated in a sonication bath at room temperature. More solids crashed out after sonication and were isolated by vacuum filtration. Drying of Form κ can be achieved by storing in a closed container over $P_2O_5$ at ambient temperature or under vacuum at ambient or elevated temperatures. Representative XRPD patterns of pre- and post-drying Form κ samples are shown in FIG. 1. The experimental conditions used to dry Form κ are included in Table 2.

TABLE 2

Drying Experiments of Rifaximin Form κ

| Starting Material | Sample Size | Condition[a] | Observations[b] | XRPD Result[c] |
|---|---|---|---|---|
| κ | —[d] | 86° C./Vacuum, 2 h | Red solid, B/E | Disordered κ |
| | 340.3 mg | Vacuum/RT, ~8 h | Red solid, partially B/E | κ |
| | 314.2 mg | Vacuum/RT, 4 h | Red solid, B/E | κ |
| | <314.2 mg | Vacuum/RT, 4 h + P$_2$O$_5$ storage | — | κ + amorph |
| | 610.5 mg | Vacuum/40° C., ~36 h | Red solid, B/E | κ + amorph |
| | 454.7 mg | P$_2$O$_5$/RT, 6 days | Red solid, B/E | κ |
| | —[d] | P$_2$O$_5$/RT, 31 days + vacuum/ RT, 4 days | — | κ |
| | —d | Undissolved solid in an IPA solution | Red gel, and B/E particles | κ |

[a]d = days, h = hours, RT = room temperature;
[b]B = birefringent; E = extinction;
[c]Amorph = x-ray amorphous;
[d]Precise sample weight was not obtained.

Characterization

The material was analyzed by x-ray powder diffractometry (XRPD) and the patterns were indexed. In addition, the material was characterized by differential scanning calorimetry (DSC), thermogravimetric analysis (TGA), dynamic vapor sorption (DVS), Karl-Fischer titration (KF), solution proton ($^1$H-) and solid-state (SS-) nuclear magnetic resonance (NMR), and attenuated total reflectance infrared (ATR-IR) and Raman spectroscopy.

XRPD Indexing (Non-GMP)

The XRPD patterns of two Form κ samples are shown in FIG. 1. Since Form κ is a variable system with flexible unit cell structure that may readily expand or contract to accommodate various amounts of solvent, it should be noted that the illustrated patterns are only representations of two discrete examples of a series of peak ranges that may be exhibited by Form κ.

Figure 2:
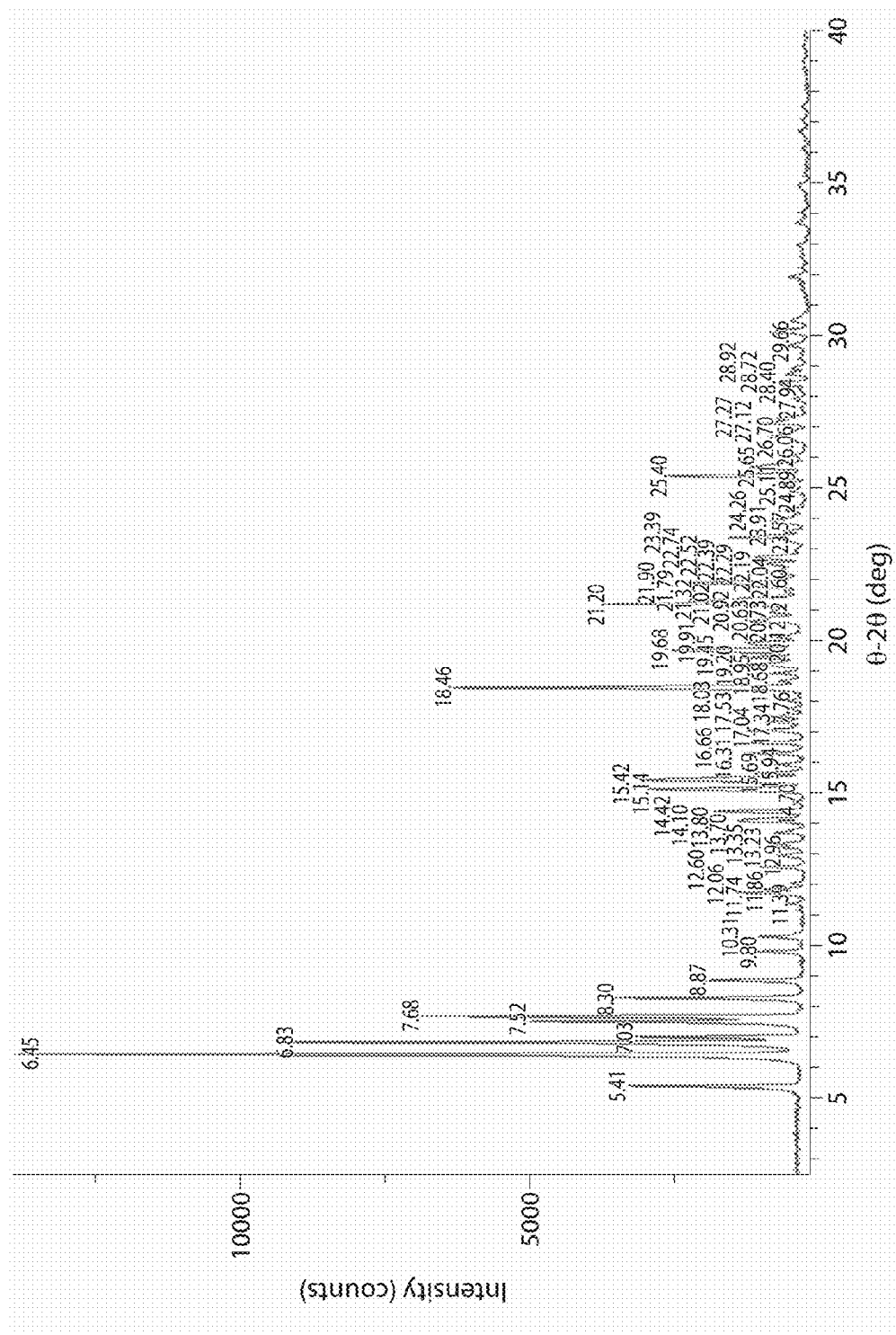
FIG. 2 is a list of observed peaks for rifaximin Form κ, corresponding to the XRPD pattern as prepared. Note that the peak labels in this image are meant as a visual aid. Consult Tables 3 and 4 for accurate 2θ positions.
Figure 3:
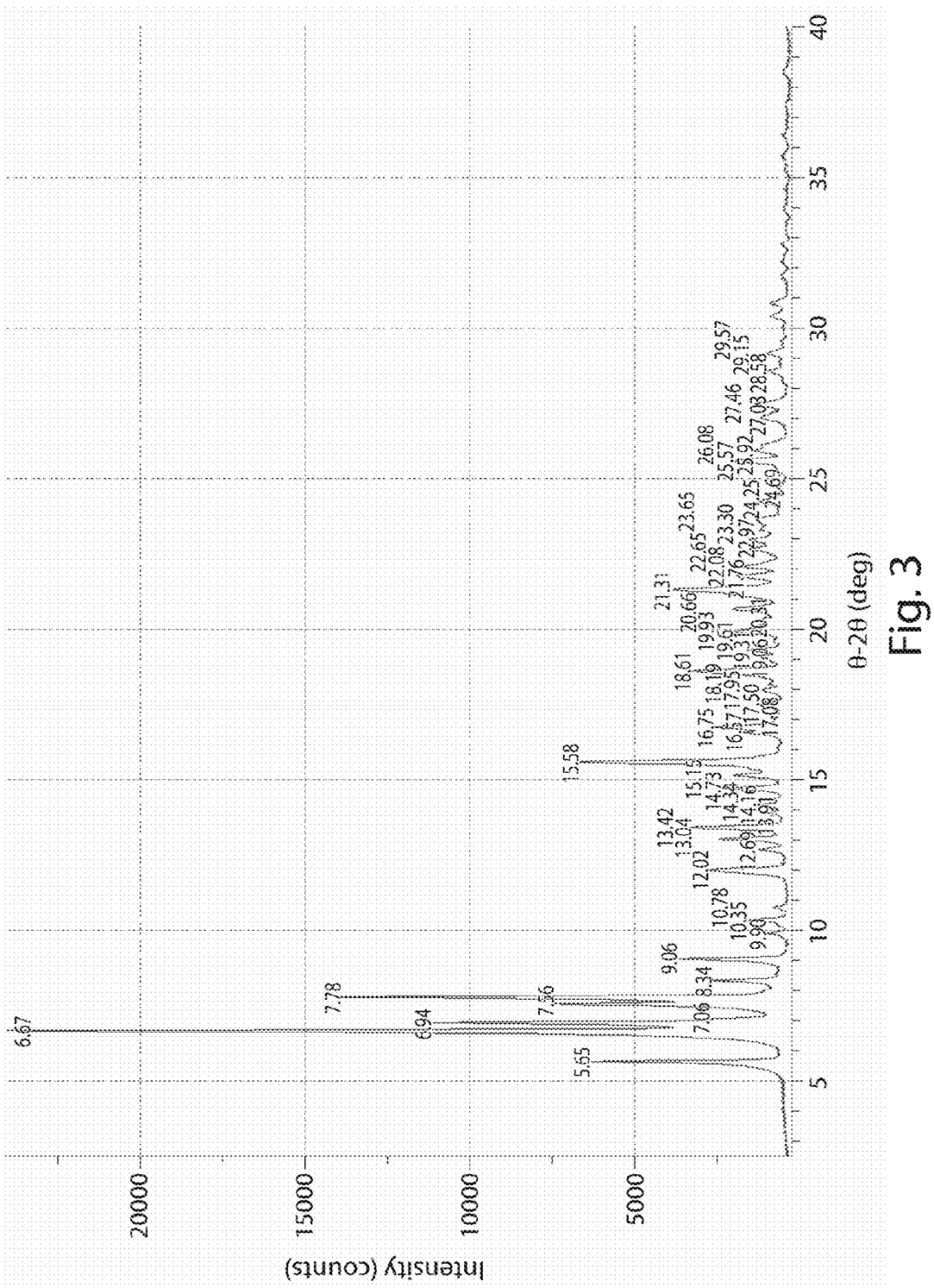
FIG. 3 is a list of observed peaks for rifaximin Form κ, corresponding to the XRPD pattern after drying. Note that the peak labels in this image are meant as a visual aid. Consult Tables 3 and 4 for accurate 2θ positions.

The list of peak positions for each XRPD pattern of rifaximin Form κ compared in FIG. 1 are presented in FIG. 2 and FIG. 3, respectively. Observed and prominent peak lists are included in Table 3 and Table 4.

TABLE 3

Observed Peaks for Rifaximin Form κ (XRPD Files FIG. 2 and FIG. 3)

| °2θ | d space (Å) | Intensity (%) |
|---|---|---|
| (5.41-5.65) ± 0.20 | 16.337 ± 0.627-15.631 ± 0.573 | 24-26 |
| (6.45-6.67) ± 0.20 | 13.713 ± 0.439-13.245 ± 0.409 | 100 |
| (6.83-6.94) ± 0.20 | 12.942 ± 0.390-12.736 ± 0.377 | 65-46 |
| (7.03-7.06) ± 0.20 | 12.574 ± 0.368-12.525 ± 0.365 | 23-12 |
| (7.52-7.56) ± 0.20 | 11.764 ± 0.321-11.695 ± 0.317 | 36-31 |
| (7.68-7.78) ± 0.20 | 11.508 ± 0.307-11.369 ± 0.300 | 50-58 |
| (8.30-8.34) ± 0.20 | 10.652 ± 0.263-10.596 ± 0.260 | 25-11 |
| (8.87-9.06) ± 0.20 | 9.971 ± 0.230-9.758 ± 0.220 | 14-15 |
| (9.80-9.90) ± 0.20 | 9.021 ± 0.187-8.936 ± 0.184 | 8-4 |
| (10.31-10.35) ± 0.20 | 8.584 ± 0.169-8.547 ± 0.168 | 8-7 |
| (10.39-10.78) ± 0.20 | 8.515 ± 0.167-8.204 ± 0.155 | 3-3 |
| (11.39-11.85) ± 0.20 | 7.768 ± 0.138-7.466 ± 0.128 | 4-6 |
| (11.74-11.95) ± 0.20 | 7.536 ± 0.130-7.404 ± 0.126 | 10-10 |
| (11.86-12.02) ± 0.20 | 7.462 ± 0.128-7.362 ± 0.124 | 7-12 |
| (12.06-12.41) ± 0.20 | 7.339 ± 0.123-7.135 ± 0.116 | 4-2 |
| (12.60-12.69) ± 0.20 | 7.028 ± 0.113-6.976 ± 0.111 | 7-6 |
| (12.96-13.04) ± 0.20 | 6.830 ± 0.107-6.789 ± 0.105 | 5-10 |
| (13.23-13.42) ± 0.20 | 6.692 ± 0.102-6.596 ± 0.099 | 5-14 |
| (13.35-13.34) ± 0.20 | 6.634 ± 0.100-6.637 ± 0.101 | 6-9 |
| (13.70-13.91) ± 0.20 | 6.465 ± 0.095-6.367 ± 0.092 | 6-4 |
| (13.80-13.86) ± 0.20 | 6.418 ± 0.094-6.390 ± 0.093 | 4-4 |
| (14.10-14.16) ± 0.20 | 6.282 ± 0.090-6.255 ± 0.089 | 10-6 |
| (14.13-14.34) ± 0.20 | 6.267 ± 0.090-6.175 ± 0.087 | 10-4 |
| (14.42-14.73) ± 0.20 | 6.144 ± 0.086-6.015 ± 0.082 | 13 |
| (14.70-15.38) ± 0.20 | 6.026 ± 0.083-5.761 ± 0.075 | 3-7 |
| (15.14-15.55) ± 0.20 | 5.854 ± 0.078-5.700 ± 0.074 | 21-24 |
| (15.42-15.58) ± 0.20 | 5.747 ± 0.075-5.688 ± 0.074 | 22-28 |
| (15.69-15.80) ± 0.20 | 5.649 ± 0.073-5.610 ± 0.071 | 8-5 |
| (15.94-16.57) ± 0.20 | 5.561 ± 0.070-5.351 ± 0.065 | 5-7 |
| (16.31-16.75) ± 0.20 | 5.436 ± 0.067-5.293 ± 0.064 | 9-11 |
| (16.66-16.75) ± 0.20 | 5.323 ± 0.064-5.293 ± 0.064 | 9-11 |
| (17.04-17.08) ± 0.20 | 5.203 ± 0.061-5.190 ± 0.061 | 9-4 |
| (17.34-17.50) ± 0.20 | 5.114 ± 0.059-5.067 ± 0.058 | 7-6 |
| (17.53-17.95) ± 0.20 | 5.061 ± 0.058-4.941 ± 0.055 | 7-5 |
| (17.76-18.39) ± 0.20 | 4.994 ± 0.056-4.825 ± 0.053 | 4-5 |
| (18.03-18.19) ± 0.20 | 4.921 ± 0.055-4.878 ± 0.054 | 4-4 |
| (18.46-18.61) ± 0.20 | 4.806 ± 0.052-4.769 ± 0.051 | 46-14 |
| (18.68-18.91) ± 0.20 | 4.751 ± 0.051-4.694 ± 0.050 | 5-4 |
| (18.95-19.06) ± 0.20 | 4.684 ± 0.050-4.657 ± 0.049 | 6-5 |
| (19.20-19.31) ± 0.20 | 4.624 ± 0.048-4.597 ± 0.048 | 11-7 |
| (19.45-19.54) ± 0.20 | 4.565 ± 0.047-4.543 ± 0.047 | 10-3 |
| (19.68-19.93) ± 0.20 | 4.511 ± 0.046-4.456 ± 0.045 | 18-9 |
| (19.91-20.66) ± 0.20 | 4.458 ± 0.045-4.299 ± 0.042 | 9-9 |

TABLE 4

Observable Peaks for Rifaximin Form κ (XRPD Files FIG. 2 and FIG. 3)

| °2θ | d space (Å) | Intensity (%) |
|---|---|---|
| (5.41-5.65) ± 0.20 | 16.337 ± 0.627-15.631 ± 0.573 | 24-26 |
| (6.45-6.67) ± 0.20 | 13.713 ± 0.439-13.245 ± 0.409 | 100 |
| (6.83-6.94) ± 0.20 | 12.942 ± 0.390-12.736 ± 0.377 | 65-46 |
| (7.52-7.56) ± 0.20 | 11.764 ± 0.321-11.695 ± 0.317 | 36-31 |
| (7.68-7.78) ± 0.20 | 11.508 ± 0.307-11.369 ± 0.300 | 50-58 |
| (8.30-8.34) ± 0.20 | 10.652 ± 0.263-10.596 ± 0.260 | 25-11 |
| (18.46-18.61) ± 0.20 | 4.806 ± 0.052-4.769 ± 0.051 | 46-14 |

Figure 4:
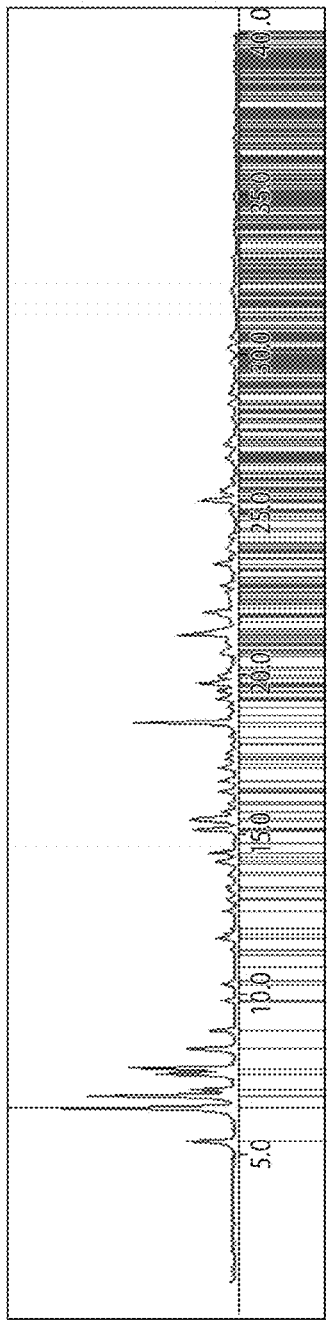
FIG. 4 shows a tentative indexing solution for rifaximin Form κ, as prepared. The bars indicate allowed reflections based on the unit cell dimensions and the assigned space group ($P2_1$, #4).
Figure 5:
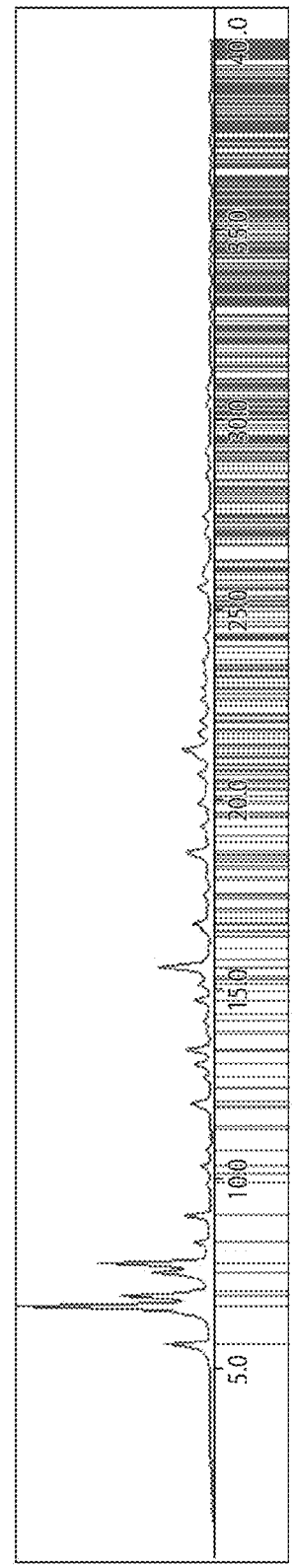
FIG. 5 shows a tentative indexing solution for rifaximin Form κ, after drying. The bars indicate allowed reflections based on the unit cell dimensions and the assigned space group ($P2_1$, #4).

The XRPD patterns of rifaximin Form κ were indexed using proprietary SSCI software and are illustrated in FIG. 4 and FIG. 5. Indexing is the process of determining the size and shape of the unit cell given the peak positions in a diffraction pattern. The term gets its name from the assignment of Miller index labels to individual peaks. For most applications, the index labels are less important than are the unit cell length and angle parameters that provide the link between unit cell properties and the diffraction pattern. The indexed solutions were verified and illustrated using CheckCell version Nov. 1, 2004.

Agreement between the allowed peak positions, marked with bars in FIG. 4 and FIG. 5, and the observed peaks indicates a consistent unit cell determination. Successful indexing of the pattern indicates that each sample is composed primarily of a single crystalline phase. Space groups consistent with the assigned extinction symbol, unit cell parameters, and derived quantities are tabulated in Table 5. To confirm the indexing solution, the molecular packing motifs within the crystallographic unit cells must be determined. No attempts at molecular packing were performed.

TABLE 5

Tentative Indexing Solutions and Derived Quantities of Rifaximin Form κ

| Pattern | Form κ | Form κ (post-drying) |
|---|---|---|
| Family and Space Group | Monoclinic $P2_1$ (#4) | Monoclinic $P2_1$ (#4) |
| Z'/Z | 2/4 | 2/4 |
| a (Å) | 13.390 | 13.324 |
| b (Å) | 25.140 | 24.978 |
| c (Å) | 16.918 | 16.331 |
| α (deg) | 90 | 90 |
| β (deg) | 105.19 | 107.15 |
| γ (deg) | 90 | 90 |
| Volume (Å³/cell) | 5496.0 | 5193.4 |
| V/Z (Å³/formula unit) | 1374.0 | 1298.4 |
| Assumed Composition[a] | $C_{43}H_{51}N_2O_{11} \cdot xC_3H_8O$ $0 \leq x \leq 4$ | $C_{43}H_{51}N_2O_{11} \cdot xC_3H_8O$ $0 \leq x \leq 3$ |
| Density (g/cm³)[a] | $0.95 \leq y \leq 1.24$ | $1.01 \leq y \leq 1.24$ |
| Weight Fraction Solvent (%)[a] | $0 \leq z \leq 23.4$ | $0 \leq z \leq 18.6$ |

[a]Density and weight fraction solvent based on the assumed composition.

The volume of rifaximin (1027 Å³/molecule) was derived from a previous rifaximin hydrate structure. Assuming two independent rifaximin molecules in the asymmetric unit, there is sufficient volume remaining for up to four molecules of IPA per molecule of rifaximin from the indexing solution. Density and solvent values calculated in Table 5. Table 5 are listed with a range of zero to four molecules of IPA per molecule of rifaximin. A second XRPD pattern of Form κ was also indexed with a volume per formula unit of 1295 Å³, and up to 3 moles of IPA per rifaximin are possible in the available volume. Analysis of Form κ samples by KF and ¹H-NMR shows that a sample with similar XRPD pattern contains negligible amount of water and approximately 2 moles of IPA per mole of rifaximin, while a post-drying sample similar to that for contains approximately 0.4 mole of IPA per mole of rifaximin and 0.75 wt % of water (Table 6 and Table 7), respectively.

TABLE 6

Characterizations of As-Prepared Rifaximin Form κ

| Analytical Technique | Results[a] |
|---|---|
| DSC | Broad endo: <100° C. |
| | Endo: 124° C. (max) |
| | Endo or baseline shift: 203° C. |
| TGA | Weight loss: 0.6% up to 60° C., 10.4% from 60 to 200° C. |
| Karl-Fischer | Water amount undetectable |
| Hot-stage Microscope | 23.3° C.: crystalline, heating 5° C./min |
| | 80.1° C.: no apparent change |
| | 101.9° C.: loss of birefringence in many particles, likely collapse of crystal (no melt) |
| | 109.2° C.: same as at 101.9° C. |
| | 123.2° C.: nearly all birefringence lost, no melt |
| | 150.1° C.: trace birefringence, change to 10° C./min |
| | 203.1° C.: isotropic but original shape retained |
| | 213.1° C.: flow observed, started to cool |
| | —: cools to an isotropic glass |
| ATR-IR | Spectrum acquired |
| ¹H-NMR | Chemical structure intact |
| | Approx 2 moles IPA present per mole rifaximin |
| Solid-state ¹³C NMR | Spectrum acquired |
| Moisture Balance | 7.5% wt loss upon equilibration at 5% RH |
| | 4.6% wt gain from 5 to 95% RH |
| | 12% wt loss from 95 to 5% RH. |
| | Overall wt loss = 14.9% (equivalent to ~2 moles of IPA) |
| Post-MB XRPD | Disordered |

[a]Endo = endotherm.

TABLE 7

Characterizations of Post-Drying Rifaximin Form κ

| Analytical Technique | Results[a] |
|---|---|
| DSC | Endo: −23, 76, 137, 204 |
| TGA | 1.4% wt loss up to 60, 9.7% wt loss from 60 to 200 |
| | 1.1% wt loss up to 60, 5.2% wt loss from 60 to 200 |
| Karl-Fischer | 0.76 wt % of water |
| ATR-IR | Spectrum acquired |
| ¹H-NMR | Structure intact, 0.4 mole of IPA per mole of API |
| | Structure intact, 0.57 mole of IPA per mole of API |
| Solid-state ¹³C NMR | Spectrum acquired |
| Moisture Balance | 0.1% wt loss upon equilibration at 5% RH |
| | 7.7% wt gain from 5%-95% RH |
| | 11.0% wt lost from 95%-5% RH |
| Post-MB XRPD | Disordered κ |

Both XRPD patterns discussed above represent a single phase of rifaximin, designated as Form κ. Because Form κ is a variable solvate, the unit cell parameters may change via expansion or contraction to accommodate the solvent. XRPD peak positions are a direct result of the unit cell parameters, and therefore one single XRPD pattern will not be representative of the crystal Form, but merely a snapshot of the form in one position and can still be used to identify the form. Thus, if a material is found to have the same XRPD pattern, it is identifiable as Form κ Likewise, materials that fall within the indexing of Form κ are also identifiable as Form κ. Peak lists are presented for the two patterns above and are combined in Table 3 and Table 4 to provide peak position ranges. Please note that these ranges only illustrate the typical peak positions observed for Form κ and do not necessarily establish the upper and lower limit of Form κ peak positions.

Additional Characterization

Additional characterization data for as-prepared rifaximin Form κ are presented in FIG. 6 through FIG. 9, and are summarized in Table 6.

Figure 6:
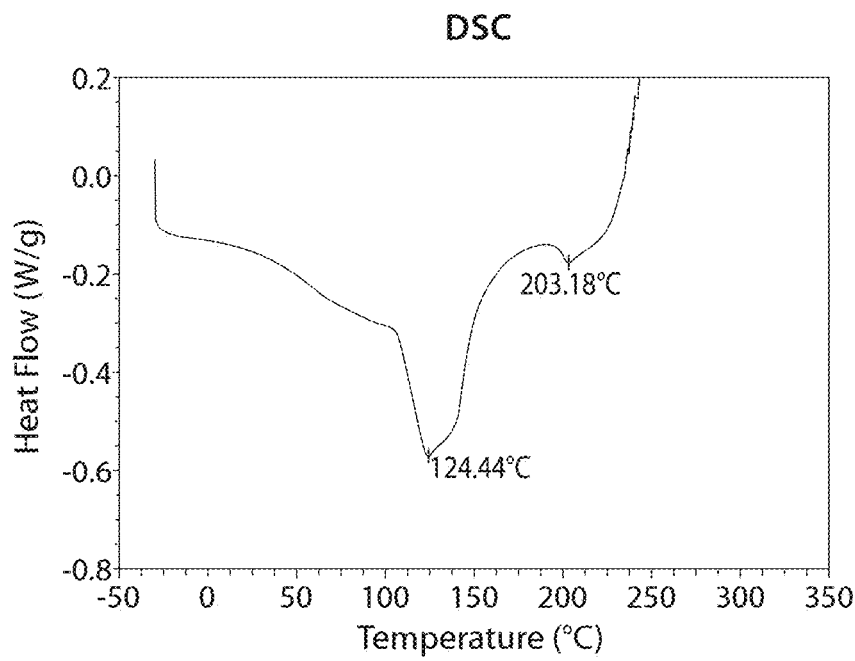
FIG. 6 is a DSC thermogram of rifaximin Form κ, as prepared.
Figure 7:
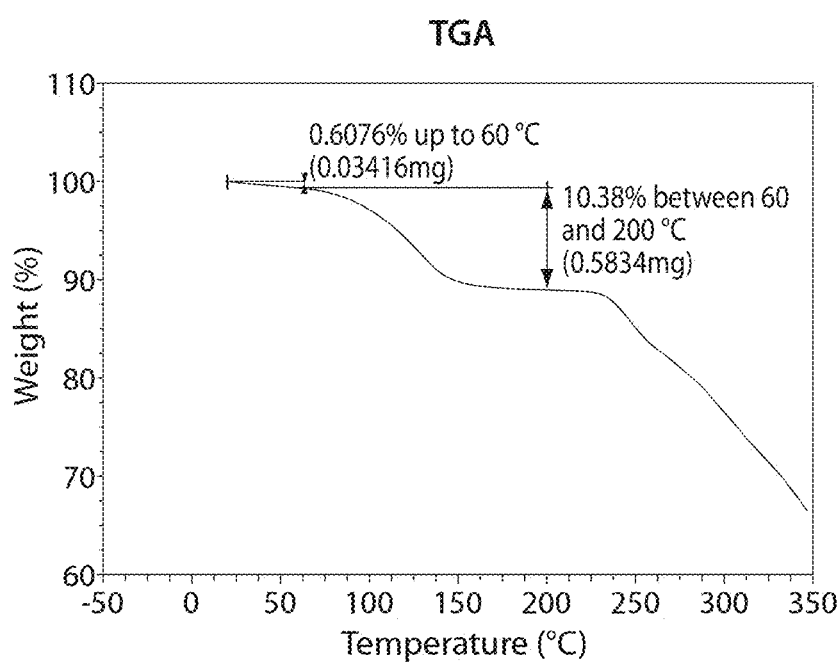
FIG. 7 is a TGA thermogram of rifaximin Form κ, as prepared.
Figure 8A:
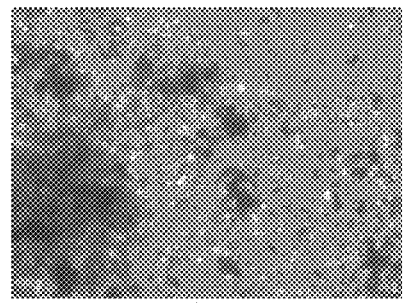
FIG. 8a was taken at 23.3° C., FIG. 8b was taken at 80.1° C., FIG. 8c was taken at 101.9° C., FIG. 8d was taken at 109.2° C., FIG. 8e was taken at 123.2° C., FIG. 8f was taken at 150.1° C., FIG. 8g was taken at 203.1° C.
Figure 8B:
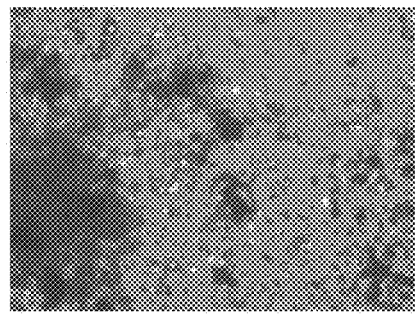
FIG. 8 are hot-stage micrographs of rifaximin Form κ.
FIG. 8h was taken at 213.1° C.
Figure 8C:
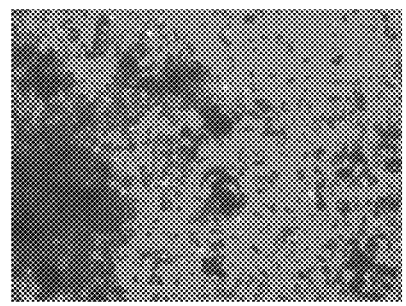
Figure 8D:
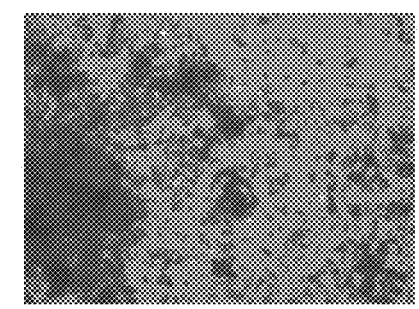
Figure 8E:
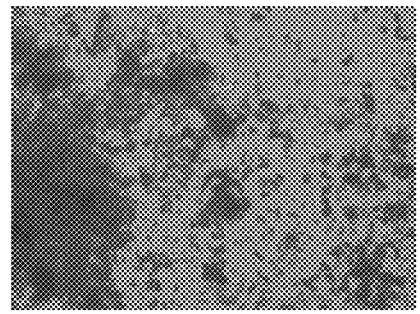
Figure 8F:
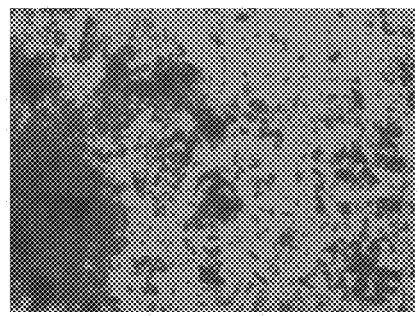
Figure 8G:
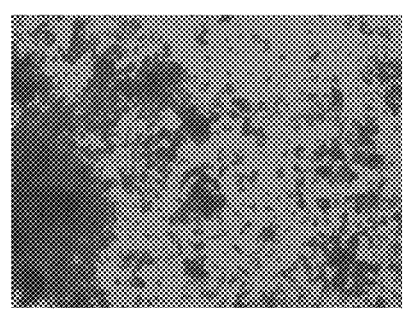
Figure 8H:

DSC and TG thermograms of Form κ are shown in FIGS. 6 and 7, respectively. The absence of a sharp melt endotherm in the DSC thermogram further suggests that Form κ may be a nonstoichiometric solvate. Loss of birefringence was observed from approximately 102° C. in hot-stage microscope, and flow was noted above approximately 213° C. (FIG. 8, Table 6).

Figure 9:
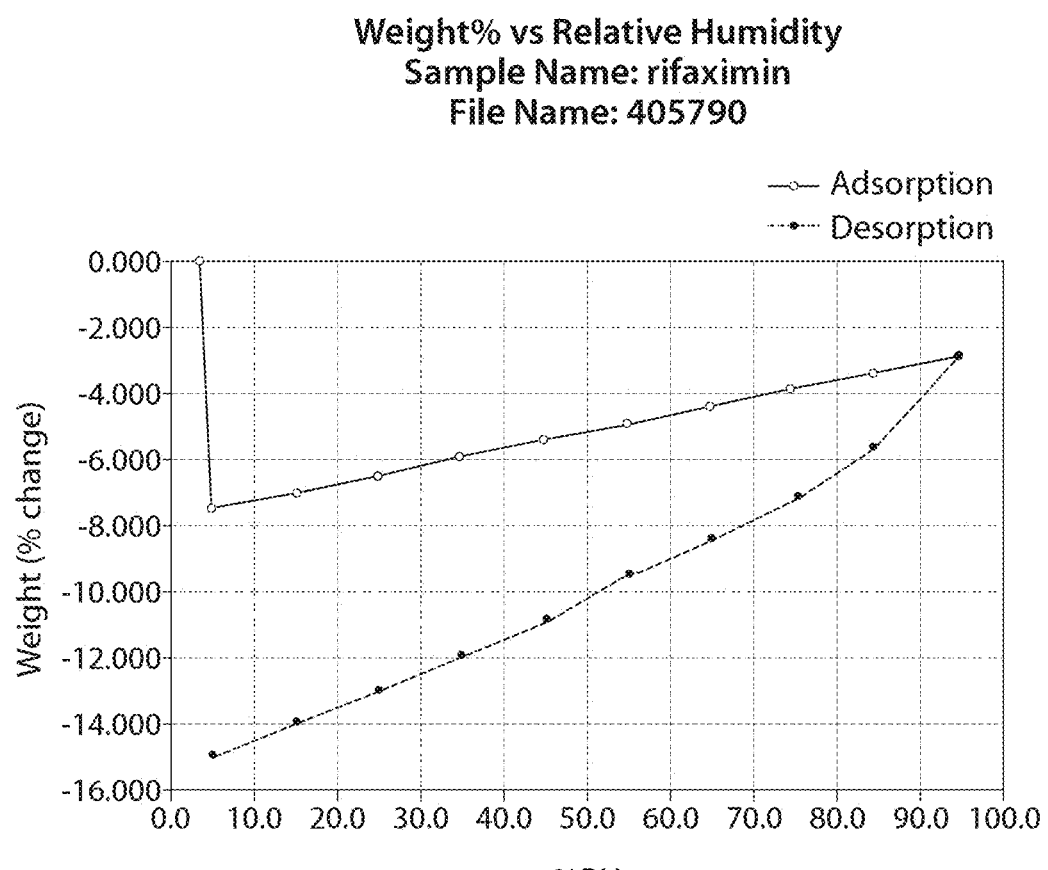
FIG. 9 shows the moisture sorption of rifaximin Form κ.
Figure 10:
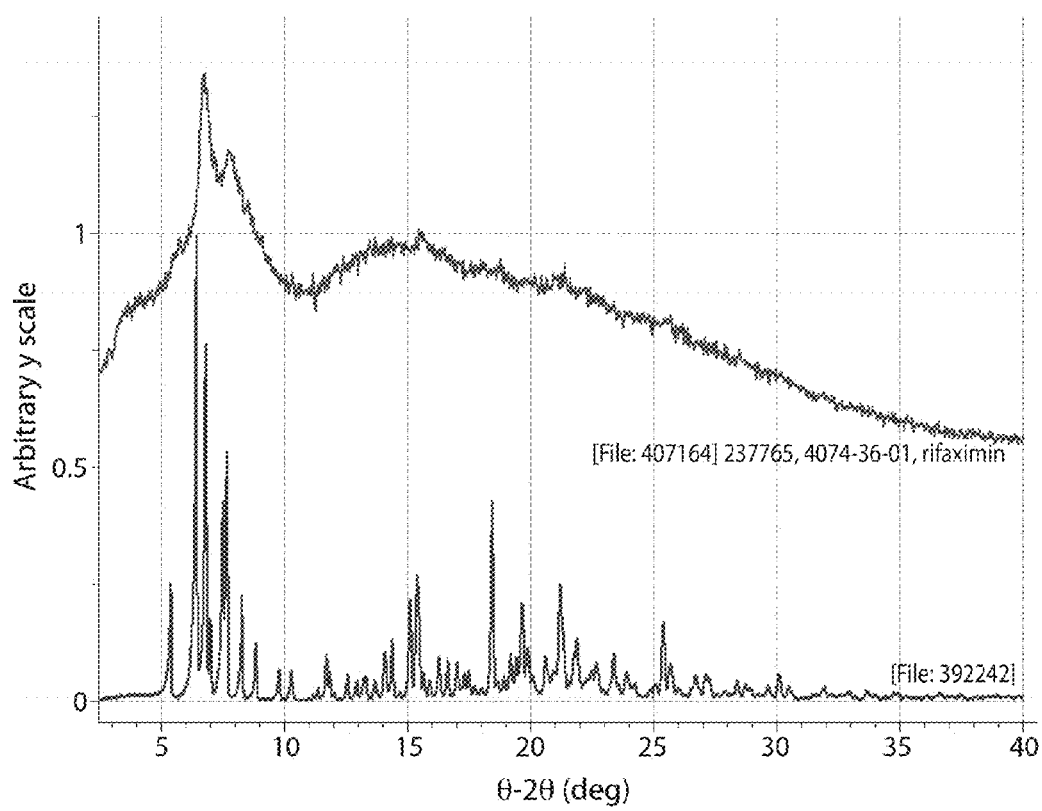
FIG. 10 shows the post-moisture sorption XRPD of rifaximin Form κ. The top XRPD patter is after moisture sorption. The bottom XRPD is before moisture sorption.

Moisture sorption data for rifaximin Form κ are shown in FIG. 9. An initial weight loss of 7.5% was observed upon equilibration at 5% RH. The material exhibited a 4.6% weight gain from 5 to 95% RH and a 12% weight loss from 95 to 5% RH. The overall weight loss is approximately 14.9%, which is consistent with the loss of approximately 2 moles of IPA. The XRPD pattern of the specimen post-moisture sorption (FIG. 10) indicates the material is disordered as judged visually by the presence of broadened reflection peaks and increased baseline.

Post-Drying Form κ

Additional characterization data for post-drying samples of rifaximin Form κ are presented in FIG. 11 to FIG. 14, and are summarized in Table 7 and Table 8.

TABLE 8

Stress Study of Post-drying Rifaximin Form κ

| Condition | Observations | XRPD Result |
|---|---|---|
| 84% RH, RT, 19 days | Red solid | Disordered κ |

Figure 11:
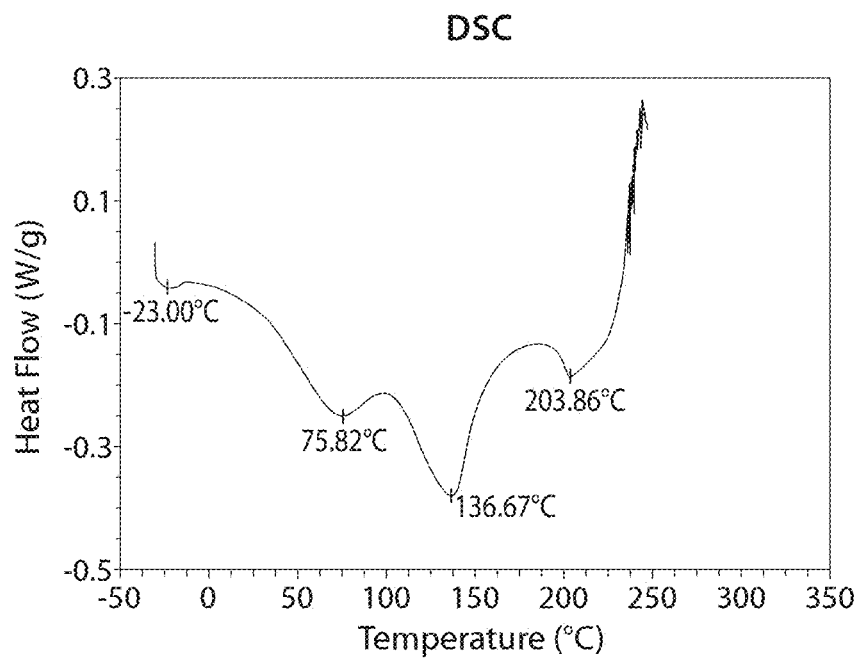
FIG. 11 is a DSC thermogram of rifaximin Form κ, post-drying.
Figure 12:
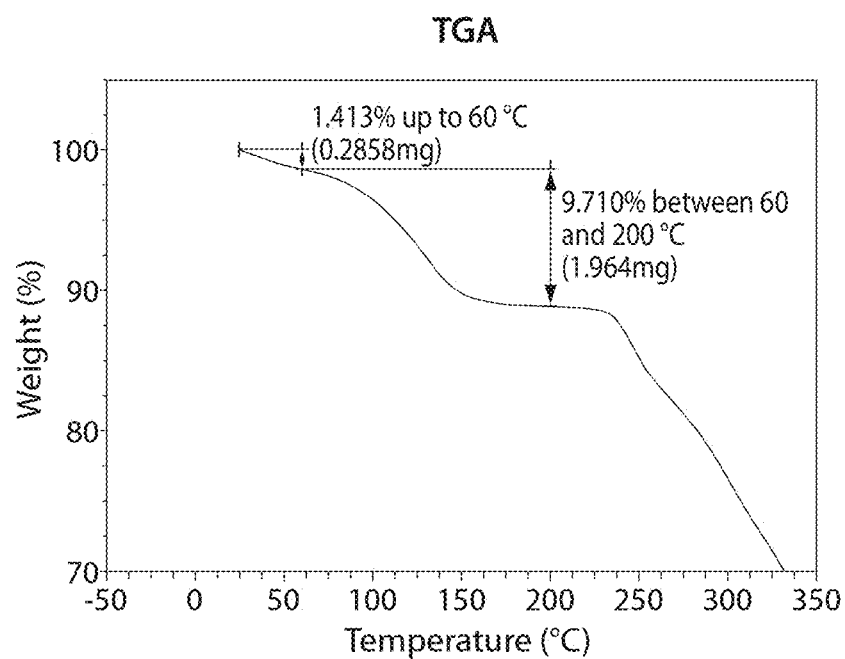
FIG. 12 is a TGA thermogram of rifaximin Form κ, post-drying.
Figure 13:
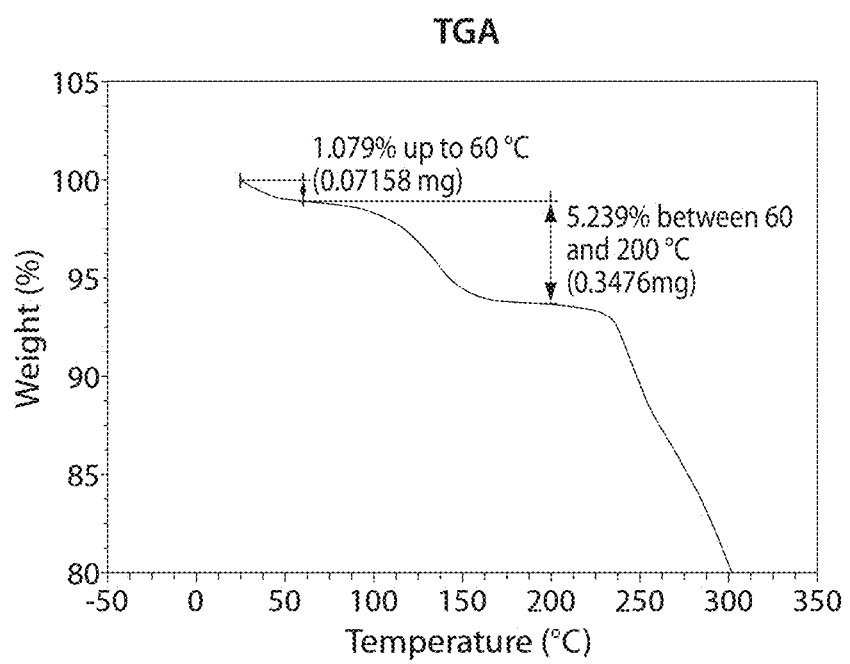
FIG. 13 is a TGA thermogram of rifaximin Form κ, post-drying after $P_2O_5$ storage.
Figure 14:
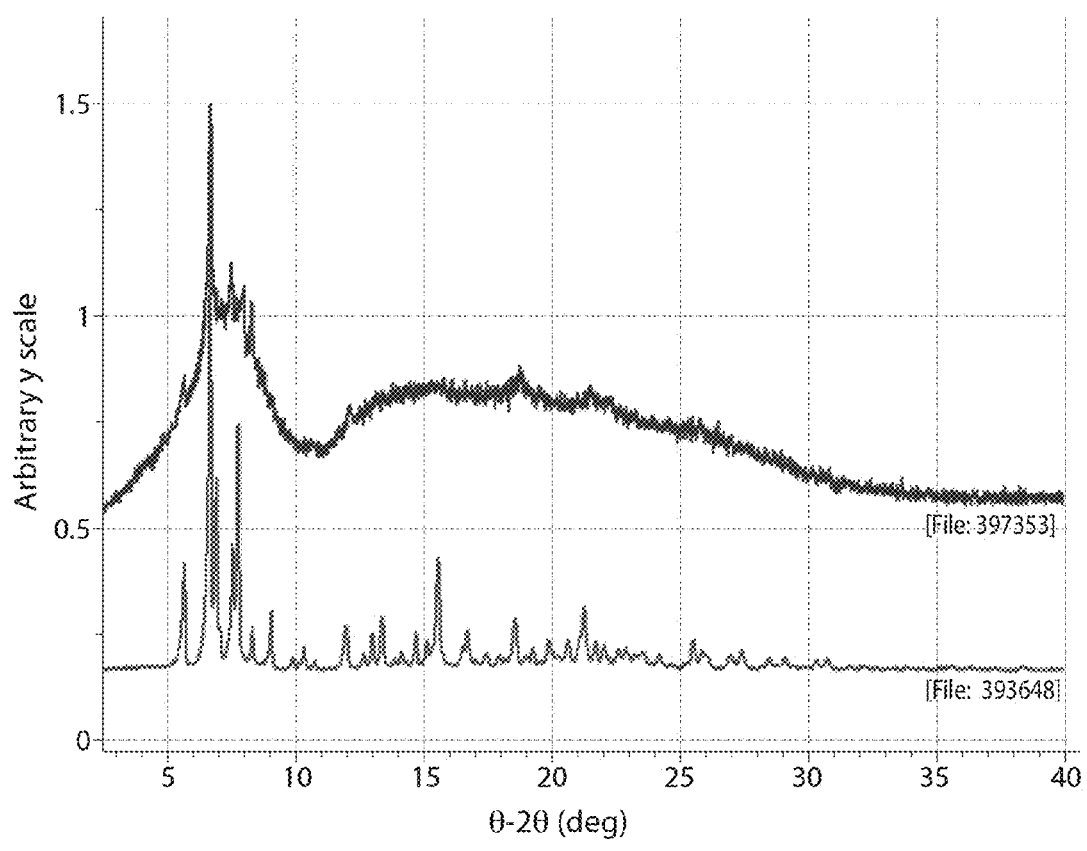
FIG. 14 is an XRPD patter of post-drying Form κ after 84% RH stress. The top XRPD pattern is after stress. The bottom XRPD pattern is starting material.

DSC and TG thermograms of post-drying Form κ are shown in FIG. 11 and FIG. 12. The absence of a sharp melt endotherm in the DSC thermogram further suggests that Form κ may be a nonstoichiometric solvate.

Figure 15:
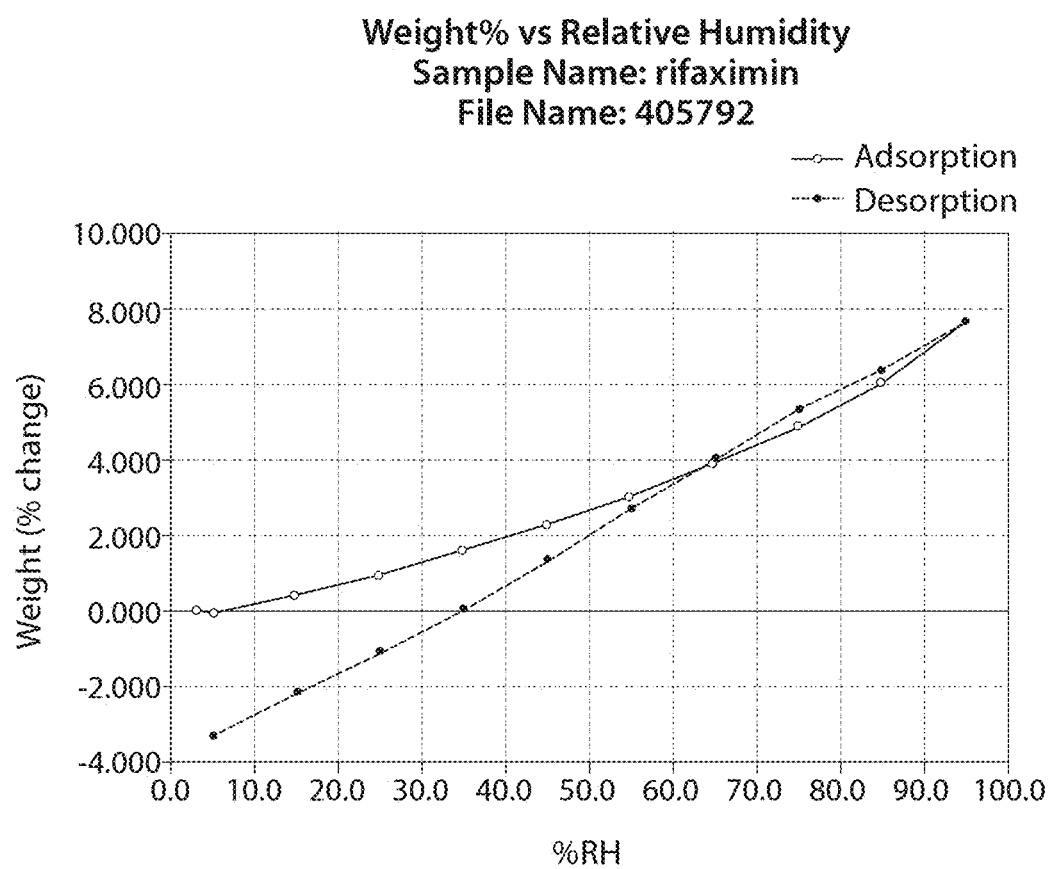
FIG. 15 shows moisture sorption of post-drying rifaximin Form κ.
Figure 16:
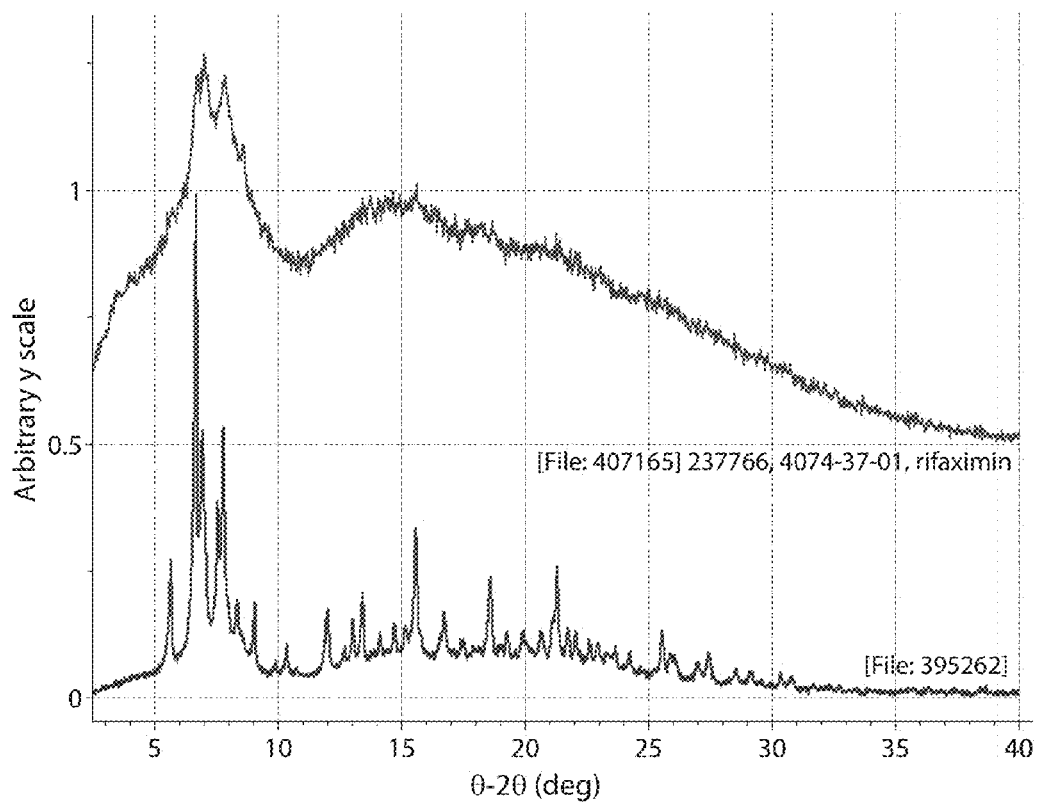
FIG. 16 shows post-moisture sorption of XRPD rifaximin Form κ, post drying. The top XRPD pattern is after moisture sorption. The bottom XRPD pattern is before moisture sorption.

Moisture sorption data for post-drying rifaximin Form κ are shown in FIG. 15 and summarized in Table 7. An initial weight loss of 0.1% was observed upon equilibration at 5% RH. The material exhibited a 7.7% weight gain from 5 to 95% RH and a 11% weight loss from 95 to 5% RH. The overall weight loss is approximately 3.3%. The XRPD pattern of the specimen post-moisture sorption FIG. 16 indicates the material is disordered as judged visually by the presence of broadened reflection peaks and increased baseline.

Form Kappa (κ) was obtained by dissolving Form Alpha (α) in isopropanol at loadings ranging from 57 to 197 mg/mL followed by mechanical agitation.

Form κ is identified as a variable system of which the unit cell parameters may change via expansion or contraction to accommodate the solvent. Multiple XRPD patterns obtained on various samples suggest that a range exist for the reflection peaks observed in Form κ. Indexing solutions were obtained on two representative XRPD patterns of Form κ but do not necessarily indicate the upper and lower limit of the range. Rather they should be considered two discrete examples of the Form κ series. Theoretical calculation from the indexing solutions indicates that Form κ may be able to accommodate up to 4 moles of IPA per mole of rifaximin based on the void space within the unit cell. One sample contains two moles of IPA per mole of rifaximin and negligible amount of water by $^1$H-NMR and Karl-Fischer titration. Another sample, with the unit cell volume being smaller by about 75 Å$^3$ contains 0.4 mole of IPA per mole of rifaximin and 0.76 wt % of water.

Indexing solutions revealed that Form κ is indeed a variable solvate with unit cell structure capable of expanding and/or shrinking to accommodate different amounts of IPA. The absence of a sharp melt endotherm in DSC further supports the nonstoichiometric nature of Form κ.

B. Computational Methods

1. X-ray Powder Diffraction Peak Identification

The data presented in this report contain x-ray diffraction patterns with labeled peaks and tables with peak lists. The range of data collected is typically provided in the scientific report in which the data was initially reported, and is instrument dependent. Under most circumstances, peaks within the range of up to about 30° 2θ were selected. Although peaks are labeled on diffraction patterns and listed in tables, for technical reasons, different rounding algorithms were used to round each peak to the nearest 0.1° or 0.01° 2θ, depending upon the instrument used to collect the data and/or the inherent peak resolution. The peaks identified in the tables should be used for reporting purposes. The location of the peaks along the x-axis (° 2θ) in both the figures and the tables were automatically determined using proprietary software (PatternMatch™ 3.0.4) and rounded to one or two significant figures after the decimal point based upon the above criteria. Peak position variabilities are given to within ±0.2° 2θ based upon recommendations outlined in the USP discussion of variability in x-ray powder diffraction (United States Pharmacopeia, USP 32, NF 27, Vol. 1, pg. 392, 2009). The accuracy and precision associated with any particular measurement reported herein has not been determined. Moreover, third party measurements on independently prepared samples on different instruments may lead to variability which is greater than ±0.1° 2θ. For d-space listings, the wavelength used to calculate d-spacings was 1.541874 Å, a weighted average of the Cu—K$_{α1}$ and Cu—K$_{α2}$ wavelengths. Variability associated with d-spacing estimates was calculated from the USP recommendation, at each d-spacing, and provided in the respective data tables.

For samples with only one XRPD pattern and no other means to evaluate whether the sample provides a good approximation of the powder average, peak tables contain data identified only as "Prominent Peaks." These peaks are a subset of the entire observed peak list. Prominent peaks are selected from observed peaks by identifying preferably non-overlapping, low-angle peaks, with strong intensity.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks". In general, the more data collected to determine Representative Peaks, the more confident one can be of the classification of those peaks.

"Characteristic peaks," to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2 2θ. Not all crystalline polymorphs of a compound necessarily have at least one characteristic peak.

C. Instrumental Techniques

The following methods have not been validated for compliance with 21 CFR211.165(e).

1. Differential Scanning Calorimetry (DSC)

DSC was performed using a TA Instruments Q2000 differential scanning calorimeter. Temperature calibration was performed using NIST traceable indium metal. The sample was placed into an aluminum DSC pan, covered with a lid, and the weight was accurately recorded. A weighed aluminum pan configured as the sample pan was placed on the reference side of the cell. The data acquisition parameters and pan configuration for each thermogram are displayed in the image in the Data section of this report. The method code on the thermogram is an abbreviation for the start and end temperature as well as the heating rate; e.g., 25-250-10 means "from 25° C. to 250° C., at 10° C./min." The following table summarizes the abbreviations used in each image for pan configurations:

| Abbreviation (in comments) | Meaning |
|---|---|
| LP | Lid perforated with a laser pinhole |
| HS | Lid hermetically sealed |
| HSLP | Lid hermetically sealed and perforated with a laser pinhole |
| C | Lid crimped |
| NC | Lid not crimped |

2. Dynamic Vapor Sorption (DVS)

Automated vapor sorption (VS) data were collected on a VTI SGA-100 Vapor Sorption Analyzer. NaCl and PVP were used as calibration standards. Samples were not dried prior to analysis. Sorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

3. Hot-Stage Microscopy

Hot stage microscopy was performed using a Linkam hot stage (FTIR 600) with a TMS93 controller mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20×0.4 N.A. long working distance objective with crossed polarizers and a first order red compensator. Images were captured using SPOT software (v. 4.5.9).

4. Infrared Spectroscopy (IR)

IR spectra were acquired on Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. Wavelength verification was performed using NIST SRM 1921b (polystyrene). An attenuated total reflectance (ATR) accessory (Thunderdome™, Thermo Spectra-Tech), with a germanium (Ge) crystal was used for data acquisition. Each spectrum represents 256 co-added scans collected at a spectral resolution of 4 $cm^{-1}$ A background data set was acquired with a clean Ge crystal. A Log 1/R (R=reflectance) spectrum was obtained by taking a ratio of these two data sets against each other.

5. Karl-Fischer Titration (KF)

Coulometric Karl Fischer (KF) analysis for water determination was performed using a Mettler Toledo DL39 KF titrator. A blank titration was carried out prior to analysis. The sample was prepared under a dry nitrogen atmosphere, where approximately 1 gram of the sample were dissolved in approximately 1 mL dry Hydranal-Coulomat AD in a pre-dried vial. The entire solution was added to the KF coulometer through a septum and mixed for 10 seconds. The sample was then titrated by means of a generator electrode, which produces iodine by electrochemical oxidation: $2\ I^- \rightarrow I_2 + 2e^-$. Two replicates were obtained to ensure reproducibility.

6. Proton NMR Spectroscopy a. Solution 1D $^1$H NMR Spectroscopy (SSCI)

The solution NMR spectra were acquired with a Varian$^{UNITY}$/NOVA-400 spectrometer. The samples were prepared by dissolving approximately 5 to 10 mg of sample in $CDCl_3$ containing TMS. The data acquisition parameters are displayed in the first plot of the spectrum in the Data section of this report.

b. Solution 1D $^1$H NMR Spectroscopy (SDS, Inc.)

One solution $^1$H NMR spectrum (LIMS 228228, filename 389420) was acquired by Spectral Data Services of Champaign, Ill. at 25° C. with a Varian$^{UNITY}$/NOVA-400 spectrometer at a $^1$H Larmor frequency of 399.796 MHz. The samples were dissolved in $CDCl_3$. The spectra were acquired with a $^1$H pulse width of 6.0 μs, a 5 second delay between scans, a spectral width of 10 KHz with 35K data points, and 40 co-added scans. The free induction decay (FID) was processed with 64K points and an exponential line broadening factor of 0.2 Hz to improve the signal-to-noise ratio.

7. Solid-State NMR Spectroscopy (SSNMR)

The solid-state $^{13}$C cross polarization magic angle spinning (CP/MAS) NMR spectra were acquired at ambient temperature on a Varian$^{UNITY}$/NOVA-400 spectrometer (Larmor frequencies: $^{13}$C=100.542 MHz, $^1$H=399.787 MHz). The sample was packed into a 4 mm PENCIL type zirconia rotor and rotated at 12 kHz at the magic angle. The first three data points of the FID were back predicted using the VNMR linear prediction algorithm to produce a flat baseline. The chemical shifts of the spectral peaks were externally referenced to the carbonyl carbon resonance of glycine at 176.5 ppm.

8. Thermogravimetry (TGA)

TGA analyses were performed using a TA Instruments 2950 or Q5000 IR thermogravimetric analyzer. Temperature calibration was performed using nickel and Alumel™. Each sample was placed in an aluminum pan. The sample was hermetically sealed and the lid was pierced (for Q5000 only), then inserted into the TG furnace. The furnace was heated under nitrogen. The method code on the thermogram is an abbreviation for the start and end temperature as well as the heating rate; e.g., 25-350-10 means "from 25° C. to 350° C., at 10° C./min."

9. X-Ray Powder Diffraction (XRPD)

a. Bruker D-8 Discover Diffractometer

XRPD patterns were collected using a Bruker D8 DISCOVER diffractometer and Bruker's General Area-Detector Diffraction System (GADDS, v. 4.1.20). An incident microbeam of Cu Kα radiation was produced using a long, fine-focus tube (40 kV, 40 mA), a parabolically graded multilayer mirror, and a 0.5 mm double-pinhole collimator. Prior to the analysis, a silicon standard (NIST SRM 640c) was analyzed to verify the Si 111 peak position. A specimen of the sample was packed between 3 ion thick films to form a portable, disc-shaped specimen. The prepared specimen was loaded in a holder secured to a translation stage. A video camera and laser were used to position the area of interest to intersect the incident beam in transmission geometry. The incident beam was scanned and rastered to optimize sampling and orientation statistics. A beam-stop was used to minimize the background from air. Diffraction patterns were collected using a HISTAR™ area detector located 15 cm from the sample and processed using GADDS. The intensity in the GADDS image of the diffraction pattern was integrated and displayed as a function of 2θ.

b. Inel XRG-3000 Diffractometer

XRPD patterns were collected with an Inel XRG-3000 diffractometer. An incident beam of Cu Kα radiation was produced using a fine-focus tube and a parabolically graded multilayer mirror. Prior to the analysis, a silicon standard (NIST SRM 640c) was analyzed to verify the Si 111 peak position. A specimen of the sample was packed into a thin-walled glass capillary, and a beam-stop was used to minimize the background from air. Diffraction patterns were collected in transmission geometry using Windif v. 6.6 software and a curved position-sensitive Equinox detector with a 2θ range of 120°.

c. PANalytical X'Pert PRO MPD Diffractometer

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640c) was analyzed to verify the Si 111 peak position. A specimen of the sample was sandwiched between 3 μm-thick films and analyzed in transmission geometry. A beam-stop was used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

Example 2

Rifaximin:Piperazine Cocrystals

Both rifaximin:piperazine cocrystals were isolated only from acetonitrile-containing solvent systems and occur in a 2:1 rifaximin:piperazine stoichiometric ratio by proton NMR (Table 9 and Table 10).

TABLE 9

Cocrystal Screen with Piperazine

| Coformer | Molar Ratio[a] | Solvent System | Conditions | Habit/Description | XRPD Result |
|---|---|---|---|---|---|
| piperazine | ~6:1 | ACN | added 1 mL of ACN | orange solids | cocrystal 2 |
|  | — | — | vacuum dry 3838-21-02, RT, 1 day | orange solids | similar to cocrystal 1 + peak at ~17 °2θ |
|  | 1:1 | ACN | mill at 30 Hz, 10 min. total | orange solids | low crystalline β |
|  | 1:1 | ACN | SE | orange solids, birefringent | cocrystal 1 + cocrystal 2 |
|  | 1:1 | acetone | refrigerator 1 day | dark red solution, solid coating bottom; dark orange, aggregates and tiny particles, partially birefringent | disordered; 3 relatively intense low-angle peaks |
| piperazine | 1:1 | ACN | dry under reduced pressure ~7 min. | dry solid; bright orange, aggregates and tiny particles, not birefringent | cocrystal 1 |
| piperazine | 2:1 | acetone | VD w/ ACN, 1 day | solid present; dark orange, morphology unknown and small amount small plates, birefringent; aggregates, not birefringent | cocrystal 1 |
|  | 2:1 | DCM | VD w/ ACN, 4 days | dry solid; reddish-brown, irregular particles and aggregates, birefringent (possible single crystals) | cocrystal 2 |
|  | 2:1 | DCM | VD w/ ACN, 3 days | brown, spherulites of tiny needles and irregular plates, aggregates, birefringent; (maybe single crystals) | cocrystal 1 + cocrystal 2 |
|  | 2:1 | DCM | seeded w/rifaximin, VD w/ ACN, 3 days | brown, aggregates, birefringent at edge (no single crystals) | cocrystal 2 |
|  | 5:1 | ACN, scale-up | dry under reduced pressure ~6 min. | orange, aggregates and tiny particles, partially birefringent; | cocrystal 1 (Panalytical) |
|  | 5:1 | ACN, scale-up | dry under reduced pressure ~8 min. | orange, tiny particles and aggregates, partially birefringent | cocrystal 1 (Panalytical) |

[a]Ratio given is rifaximin:coformer.

TABLE 10

Characterization of Rifaximin:Piperazine Cocrystal

| Sample Source | Technique | Analysis/Result |
|---|---|---|
| sample 1, | XRPD | cocrystal 2 |
|  | DSC[a] | broad endo 116, possible small exo 159 or small endo 170 |
|  | TGA[b] | 8.35% weight loss from 25-190° C. |
|  | $^1$H NMR | 2:1 rifaximin:piperazine ratio, possible acetonitrile present |
| sample 2, | XRPD | cocrystal 2 |
|  | SCXRD (initial eval.) | moderate probability crystals; crystal size limiting |
|  | SCXRD | no data collected, crystal size too small |
| sample 3, | XRPD | cocrystal 1 + cocrystal 2 |
|  | SCXRD (initial eval.) | low probability crystals |
| sample 4, | XRPD (Panalytical) | cocrystal 1 |
|  | $^1$H NMR | 2:1 rifaximin:piperazine cocrystal, no solvents present, minor impurities present |
|  | DSC[a] | broad endo 108, small broad endo 173 |
|  | TGA[b] | 7.12% weight loss from 25-195° C. |
|  | DVS | 3.54% weight loss at 5% RH 10.78% weight gain from 5-95% RH 11.47% weight loss from 95-5% RH |

TABLE 10-continued

Characterization of Rifaximin:Piperazine Cocrystal

| Sample Source | Technique | Analysis/Result |
|---|---|---|
| sample 5, post-DVS | XRPD | broad peaks, similar to cocrystal 1 + peaks at ~5 and 17 °2θ |
| sample 6, | XRPD | cocrystal 2 |
|  | $^1$H NMR | 2:1 rifaximin:piperazine cocrystal, no solvents present, minor impurities present |

$^a$Endo = endotherm, exo = exotherm. Temperatures (° C.) reported are transition maxima. Temperatures are rounded to the nearest degree.
$^b$Weight loss (%) at a certain temperature; weight changes (%) are rounded to 2 decimal places; temperatures are rounded to the nearest degree.

Cocrystal 1 resulted mainly from experiments in which the solids were dried thoroughly (generally under reduced pressure during vacuum filtration), while cocrystal 2 was generally seen when materials were not dried as thoroughly. Additionally, vapor stressing of cocrystal 1 in acetonitrile caused conversion to cocrystal 2, and vacuum drying of cocrystal 2 resulted in material similar to cocrystal 1 (with an additional peak) by XRPD (Table 11). Thus, it is suspected that cocrystal 1 is unsolvated, whereas cocrystal 2 likely contains acetonitrile. Proton NMR data for each cocrystal was then acquired in CDCl$_3$, and both spectra show no solvents present, although it is likely that the time lapse between XRPD and NMR analyses allowed for desolvation of cocrystal 2.

TABLE 11

Stressing of Rifaximin:Piperazine Cocrystal 1

| Conditions | Time | Habit/Description | XRPD Result |
|---|---|---|---|
| VS w/ ACN | 7 days | orange, slightly damp solids | cocrystal 2 |
| VS w/ ACN ~75% RH | 3 days | dry orange solid similar to | broad peaks, cocrystal 1 + |
| ~97% RH | 1 week | dry orange solid | peak at ~5 °2θ broad peaks, similar to cocrystal 1 + peak at ~5 °2θ |
|  | 2 weeks | dry orange solid | broad peaks, similar to cocrystal 1 + peak at ~5 °2θ |
|  | 3 days | dry orange solid | API, Form β-1 |
|  | 1 week | dry orange solid | API, Form β-1 |
|  | 2 weeks | dry orange solid | — |

Figure 17:
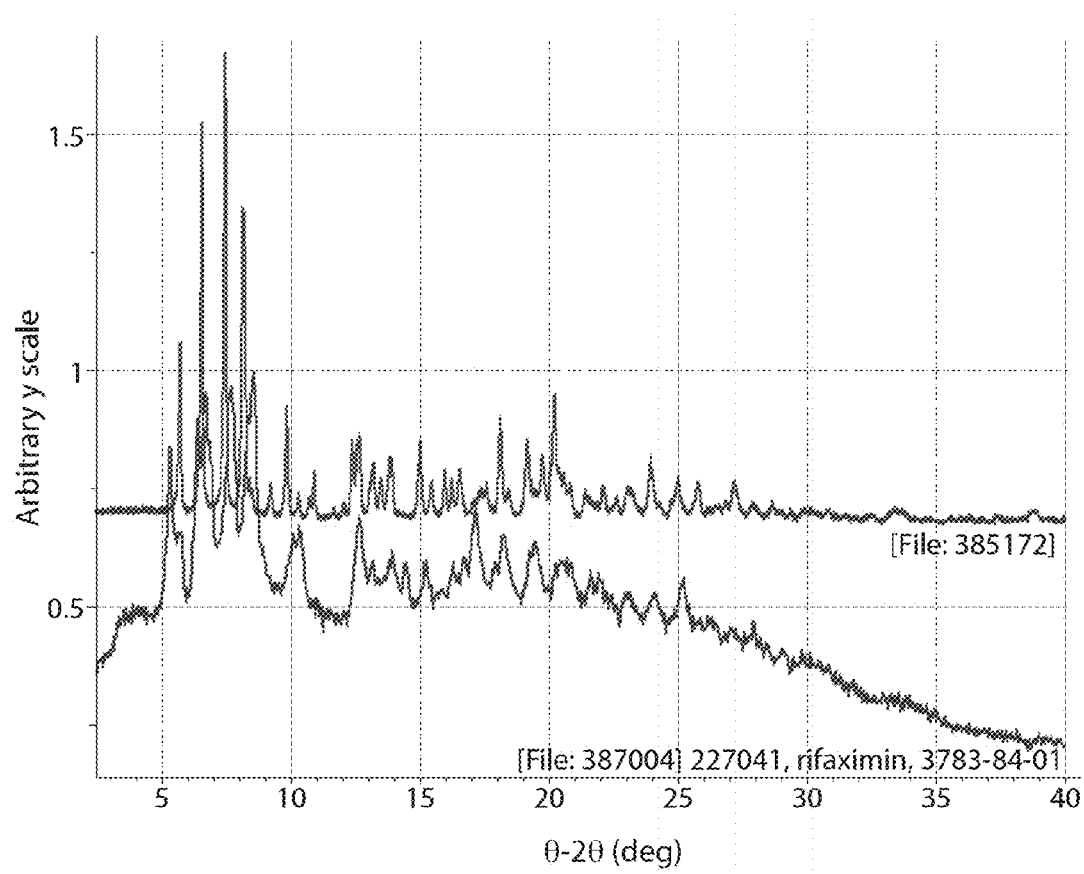
FIG. 17 shows an exemplary XRPD overlay of Rifaximin:piperazine cocrystal, post-DVS. The top XRPD pattern is pre-DVS cocrystal 1. The bottom XRPD pattern is post-DVS, broad peaks, similar to cocrystal 1+peaks at ~5 and 17°θ.

The DVS of cocrystal 1 indicates the material is quite hygroscopic. XRPD of the post-DVS material shows a pattern with broad peaks, similar to cocrystal 1 with additional peaks at approximately 5 and 17° 2θ (Table 10, FIG. 17).

Figure 18:
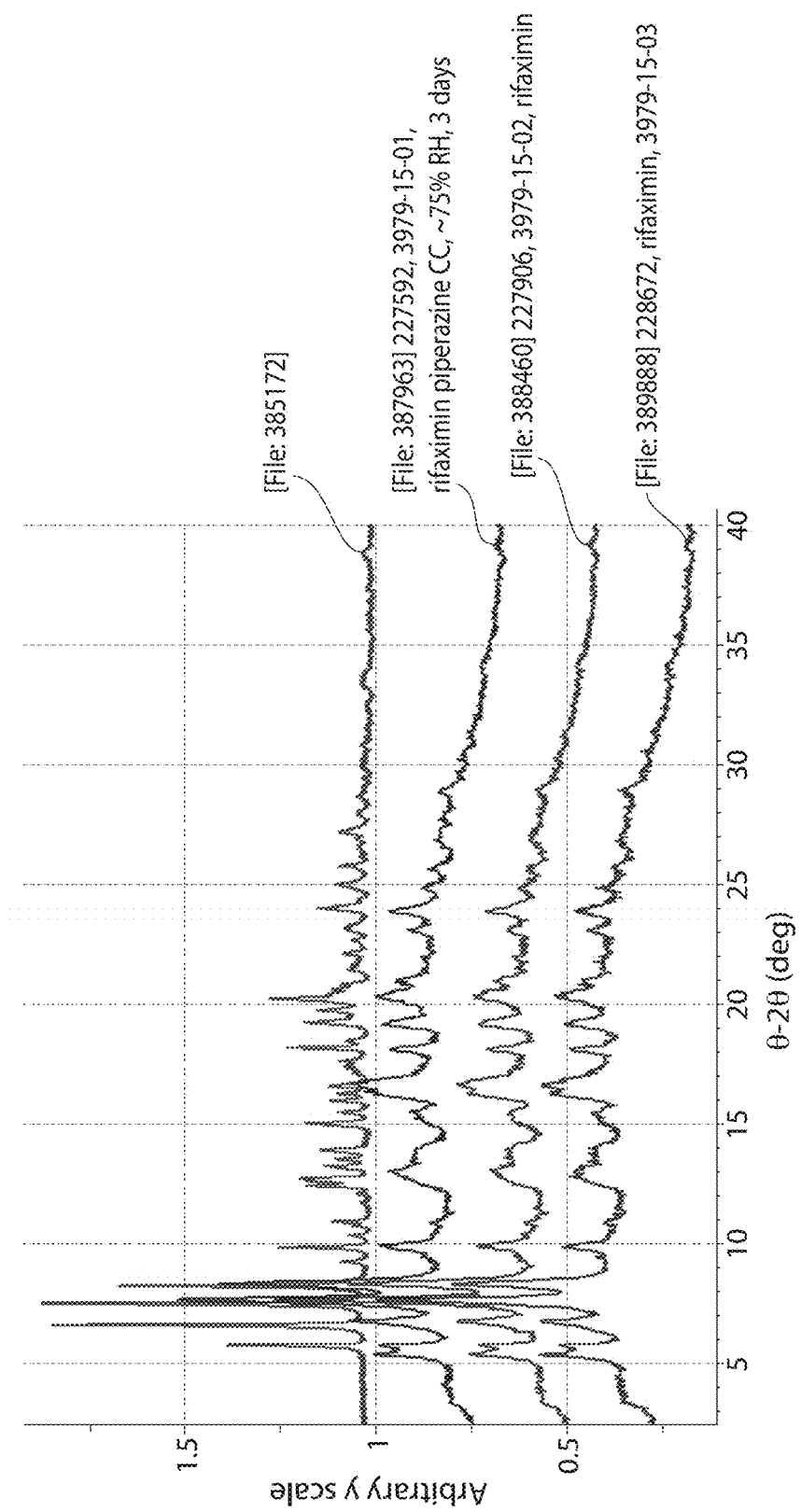
FIG. 18 is an XRPD overlay of Rifaximin:piperazine cocrystal, post-RH stressing. Top to bottom: cocrystal 1, unstressed; broad peaks, similar to cocrystal 1+peak at ~5° 2θ, 3 days at ~75% RH; broad peaks, similar to cocrystal 1+peak at ~5° 2θ, 1 week at ~75% RH; broad peaks, similar to cocrystal 1+peak at ~5° 2θ, 2 weeks at ~75% RH.

Relative humidity stressing experiments of cocrystal 1 at approximately 75% RH also resulted in material exhibiting an XRPD pattern with broad peaks, similar to cocrystal 1 with an additional peak at approximately 5° 2θ (Table 11, FIG. 18). Conversion to a hydrated form of rifaximin was observed from all pulls at approximately 97% RH.

A 2:1 Rifaximin:piperazine cocrystal was found in two forms: a non-solvated/hydrated form, cocrystal 1, and an acetonitrile solvate, cocrystal 2. Information regarding preparation and characterization of the two cocrystals is summarized in the Table 12 below. The scheme below illustrates the relationship between the cocrystals.

TABLE 12

Preparation of Rifaximin Co-Crystals

| Rifaximin:Piperazine Cocrystal | Preparation | Properties | Characterization Performed |
|---|---|---|---|
| cocrystal 1 | precipitation from ACN acetone, VD with ACN RC with ACN, dried under reduced pressure likely desolvation of cocrystal 2 at ambient conditions | non-solvated/hydrated hygroscopic single crystalline phase unstable upon exposure to water, elevated RH, and compression likely falls apart upon heating | XRPD, DSC, TGA, DVS, Proton NMR, Solid-state NMR, and IR and Raman Spectroscopy (with peak picking) XRPD successfully indexed (with peak picking) |
| cocrystal 2 | RC with ACN DCM, VD with ACN VS of cocrystal 1 with ACN | ACN solvate (1 mole) single crystalline phase unstable upon exposure to ambient conditions likely falls apart upon heating | XRPD, DSC, TGA, Proton NMR, and IR and Raman Spectroscopy (with peak picking) XRPD successfully indexed (with peak picking) |

TABLE 13

Abbreviations

| Type | Abbreviations/Acronyms | Full Name/Description |
|---|---|---|
| Solvent | ACN | acetonitrile |
| | DCM | dichloromethane |
| | EtOH | ethanol |
| | EtOAc | ethyl acetate |
| | IPA | isopropanol |
| | IPE | isopropyl ether |
| | MeOH | methanol |
| | MEK | methyl ethyl ketone |
| | MTBE | tert-butyl methyl ether |
| | THF | tetrahydrofuran |
| | TFE | 2,2,2-trifluoroethanol |
| Methods | CP | crash precipitation |
| | RC | reaction crystallization |
| | SC | slow cool |
| | SE | slow evaporation |
| | VD | vapor diffusion |
| | VS | vapor stress |
| | VSE | very slow evaporation |
| Techniques | DSC | differential scanning calorimetry |
| | $^1$H NMR | proton nuclear magnetic resonance spectroscopy |
| | IR | infrared spectroscopy |
| | DVS | dynamic vapor sorption |
| | TG or TGA | thermogravimetric analysis |
| Other | SSNMR | solid-state nuclear magnetic resonance spectroscopy |
| | XRPD | x-ray powder diffraction |
| | API | active pharmaceutical ingredient |
| | deg | degrees |
| | endo | endotherm |
| | eval. | evaluation |
| | exo | exotherm |
| | IS | insufficient solid |
| | ppt. | precipitate or precipitation |
| | RH | relative humidity |
| | RT | room (ambient) temperature |

Characterization of Starting Materials

Rifaximin was received and characterization was performed. The material was crystalline, exhibiting the previously-known form of α-dry by XRPD. A proton NMR spectrum of the material was consistent with the structure. Solid-state NMR, IR, and Raman spectra were also collected for comparison purposes.

Solid-state NMR, IR, and Raman spectra of piperazine were also collected for comparison with corresponding data from the cocrystals of Rifaximin and piperazine made during the screen.

Manual cocrystal screen experiments were set up with Rifaximin, utilizing piperazine (Table 14).

TABLE 14

Expanded Cocrystal Screen of Rifaximin

| Coformer | Molar Ratio[a] | Solvent System | Conditions | Habit/Description | XRPD Result |
|---|---|---|---|---|---|
| piperazine | | | added 1 mL of ACN | orange solids | cocrystal 2 |
| | 1:1 | ACN | SE | orange solids, birefringent | cocrystal 1 + cocrystal 2 |
| | Molar Ratioa | Solvent System | Conditions | Habit/Description | XRPD Result |
| | | | dry under reduced pressure ~7 min. | dry solid; bright orange, aggregates and tiny particles, not birefringent | cocrystal 1 |
| | 2:1 | acetone | VD w/ ACN, 1 day | solid present; dark orange, morphology unknown and small amount small plates, birefringent; aggregates, not birefringent | cocrystal 1 |
| | 2:1 | DCM | VD w/ ACN, 4 days | dry solid; reddish-brown, irregular particles and aggregates, birefringent (possible single crystals) | cocrystal 2 |
| | 2:1 | DCM | VD w/ ACN, 3 days | brown, spherulites of tiny needles and irregular plates, aggregates, birefringent; (maybe single crystals) | cocrystal 1 + cocrystal 2 |
| | 2:1 | DCM | seeded w/ rifaximin, VD w/ ACN, 3 days | brown, aggregates, birefringent at edge (no single crystals) | cocrystal 2 |
| | 5:1 | ACN, scale-up | dry under reduced pressure ~6 min. | orange, aggregates and tiny particles, partially birefringent | cocrystal 1 (Panalytical) |

TABLE 14-continued

Expanded Cocrystal Screen of Rifaximin

| Coformer | Molar Ratio[a] | Solvent System | Conditions | Habit/Description | XRPD Result |
|---|---|---|---|---|---|
| | 5:1 | ACN, scale-up | dry under reduced pressure ~8 min. | orange, tiny particles and aggregates, partially birefringent | cocrystal 1 (Panalytical) |

[a]Ratio given is API: coformer.

Figure 19:
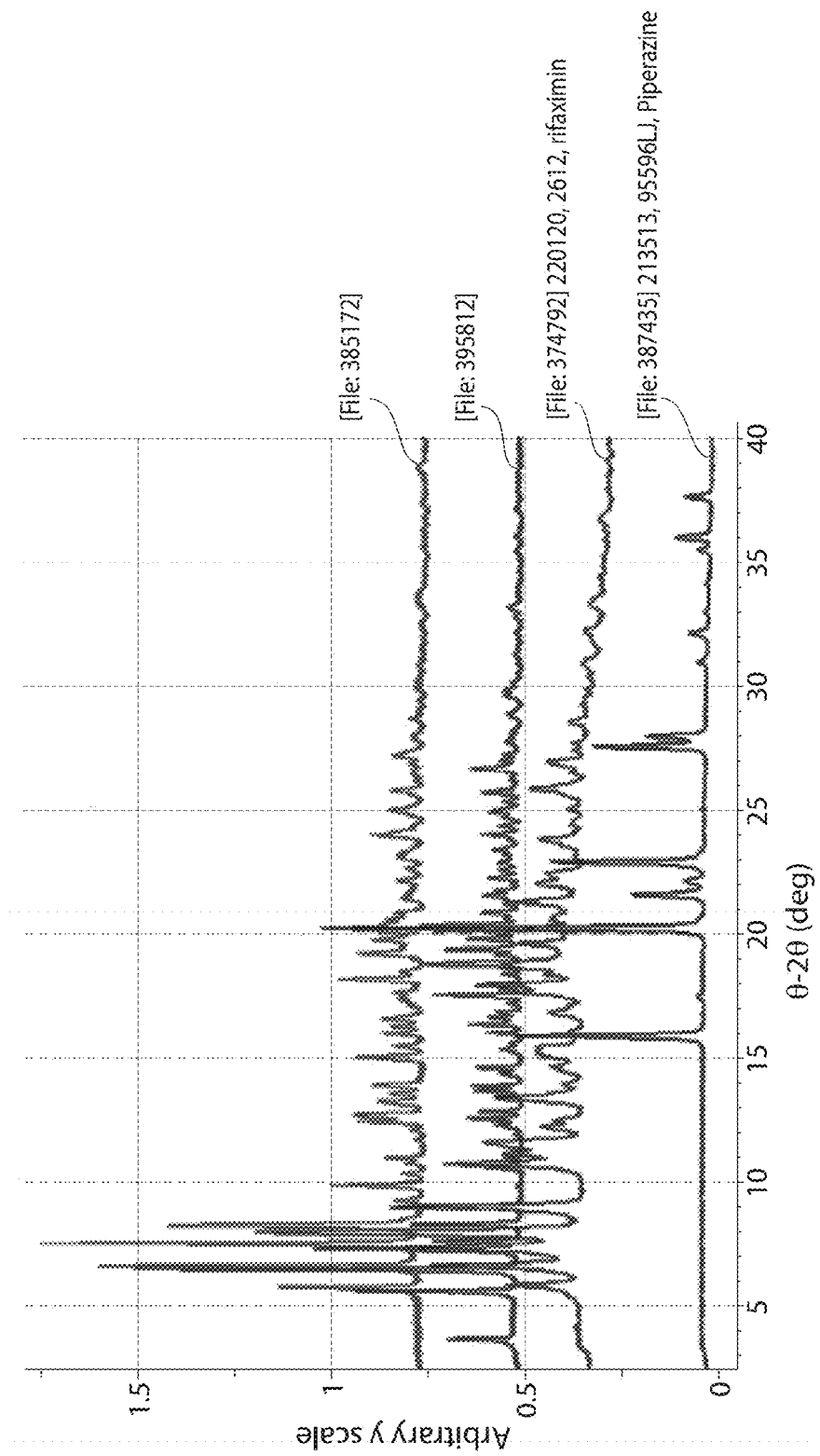
FIG. 19 shows an XRPD overlay of Rifaximin:piperazine cocrystals. From top to bottom: cocrystal 1, cocrystal 2, rifaximin, Form α-dry, piperazine.

Cocrystals were made with piperazine. Throughout the screen, two forms of this cocrystal, determined by XRPD, were found and were designated as cocrystal 1 and cocrystal 2 (FIG. 19).

Rifaximin:Piperazine Cocrystals

Preparation and Relationship of Cocrystals

Both Rifaximin:piperazine cocrystals were isolated only from acetonitrile-containing solvent systems, and occur in a

TABLE 15

Characterization of Rifaximin:Piperazine Cocrystals

| Cocrystal[a] | Technique | Analysis/Result |
|---|---|---|
| cocrystal 2 | XRPD | cocrystal 2 |
| possible | DSC[b] | broad endo 116, possible small exo 159 or small endo 170 |
| cocrystal 2 | TGA[c] | 8.35% weight loss from 25-190° C. |
| | $^1$H NMR[d] | 2:1 Rifaximin:piperazine ratio, possible acetonitrile present |
| cocrystal 2 | XRPD | cocrystal 2 |
| possible | SCXRD (initial | moderate probability crystals; crystal size limiting |
| cocrystal 2 | eval.) | |
| | SCXRD | no data collected, crystal size too small |
| cocrystal 1 + 2 | XRPD | cocrystal 1 + cocrystal 2 |
| possible | SCXRD (initial | low probability crystals |
| cocrystal 1 + 2 | eval.) | |
| cocrystal 1 | XRPD (Panalytical) | cocrystal 1 |
| | $^1$H NMR[f] | 2:1 Rifaximin:piperazine cocrystal, no solvents present, minor impurities present |
| | DSC[b] | broad endo 108, small broad endo 173 |
| | TGA[c] | 7.12% weight loss from 25-195° C. |
| | DVS | 3.54% weight loss at 5% RH |
| | | 10.78% weight gain from 5-95% RH |
| | | 11.47% weight loss from 95-5% RH |
| | SSNMR | spectrum acquired |
| | IR | spectrum acquired |
| | Raman | spectrum acquired |
| — | XRPD | broad peaks, similar to cocrystal 1 + peaks at ~5 and 17 °2θ |
| cocrystal 2 | XRPD | cocrystal 2 |
| possible | $^1$H NMR[h] | 2:1 Rifaximin:piperazine cocrystal, no solvents present, minor impurities present |
| cocrystal 1 | | |
| cocrystal 2 | XRPD[j] (Panalytical) | cocrystal 2 |
| | $^1$H NMR[i,j] | 2:1 Rifaximin:piperazine cocrystal, 1 mole ACN present, minor impurities present |
| likely cocrystal 2 | IR[j] | spectrum acquired |
| likely cocrystal 2 | Raman[j] | spectrum acquired |
| — | XRPD | broad peaks, similar to cocrystal 1 + peaks at ~5 and 17 °2θ |

[a]Due to the nature of cocrystal 2 to quickly desolvate and undergo form conversion upon exposure to ambient conditions, any delay between XRPD and other characterization techniques adds uncertainty to the form that was actually tested.
[b]Temperatures (° C.) reported are transition maxima. Temperatures are rounded to the nearest degree.
[c]Weight loss (%) at a certain temperature; weight changes (%) are rounded to 2 decimal places; temperatures are rounded to the nearest degree.
[d]solvent: deuterated DMSO.
e. After initial single crystal evaluation, sample was uncapped and placed inside a vial of hexanes for 2 days for vapor stress in an attempt to loosen potential single crystals from sides of vial; however, no suitable single crystals were observed after stressing.
[f]solvent: deuterated chloroform
[h]solvent: deuterated chloroform. 6 days elapsed between XRPD and proton NMR analyses.
[i]solvent: deuterated chloroform.
[j]Samples were analyzed quickly after isolation.

Figure 31:
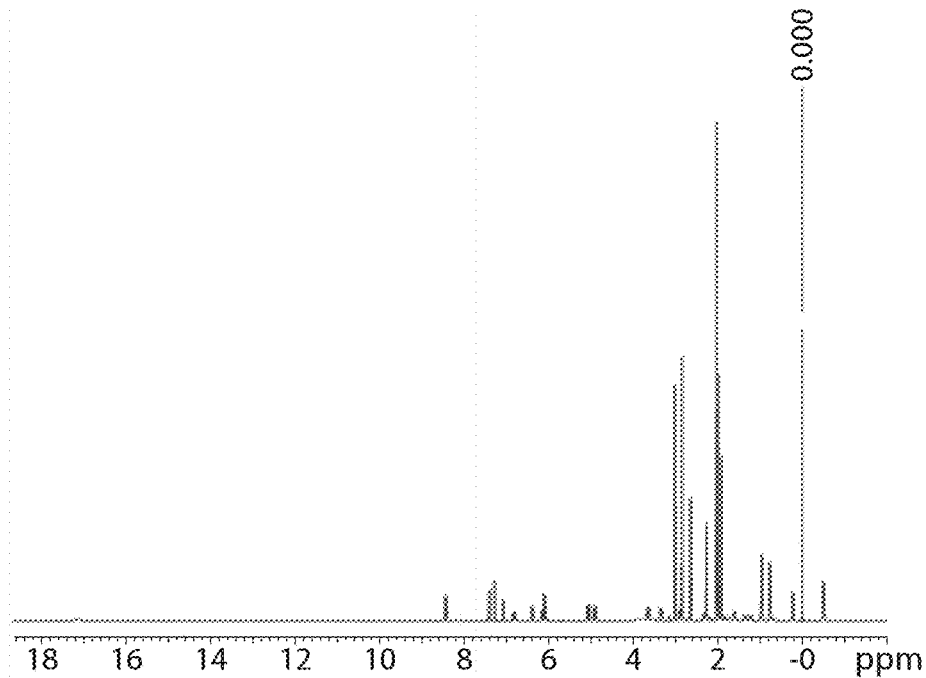
FIG. 31 is an exemplary proton NMR of Rifaximin:piperazine cocrystal 1.
Figure 43:
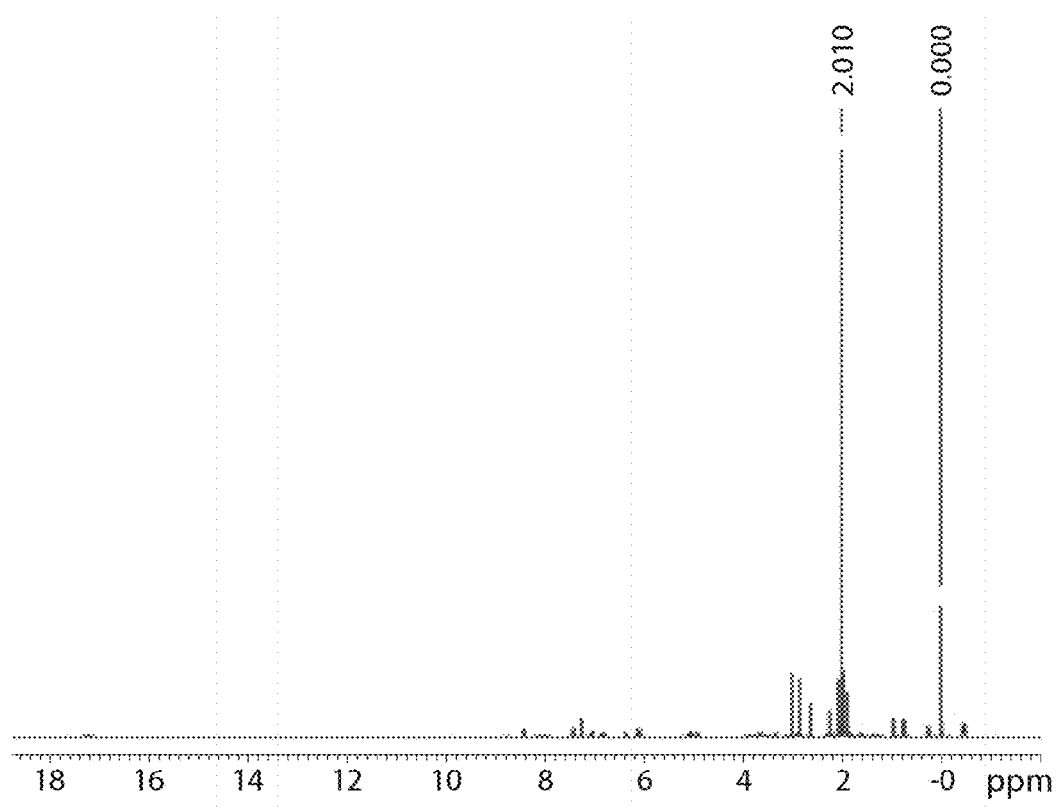
FIG. 43 shows proton NMR of Rifaximin:piperazine cocrystal 2.

2:1 Rifaximin:piperazine stoichiometric ratio by proton NMR (Table 14, Table 15, FIG. 31 and FIG. 43). An XRPD overlay for both cocrystals is presented in FIG. 19. Detailed preparation procedures for each cocrystal are provided infra.

While both cocrystals were seen from reaction crystallization and vapor diffusion experiments with acetonitrile, cocrystal 1 also resulted by spontaneous precipitation in acetonitrile, whereas a slow evaporation experiment in acetonitrile, as well as a vapor diffusion in dichloromethane utilizing acetonitrile as the antisolvent, produced mixtures of cocrystal 1 and cocrystal 2. Scale-ups of the reaction crystallization experiment in acetonitrile all gave cocrystal 1. It was then noted that cocrystal 1 resulted mainly when the solids were dried thoroughly (generally under reduced pressure during vacuum filtration), while cocrystal 2 was generally seen when materials were not dried as thoroughly, indicating cocrystal 2 may be an acetonitrile solvate.

The initial proton NMR spectrum of possible cocrystal 2 (form is uncertain due to the tendency of cocrystal 2 to undergo form conversion upon exposure to ambient conditions, discussed below) collected in deuterated DMSO was inconclusive in determining acetonitrile content due to significant peak overlap in the region of interest, ~2.07 ppm (Table 15).

Figure 20:
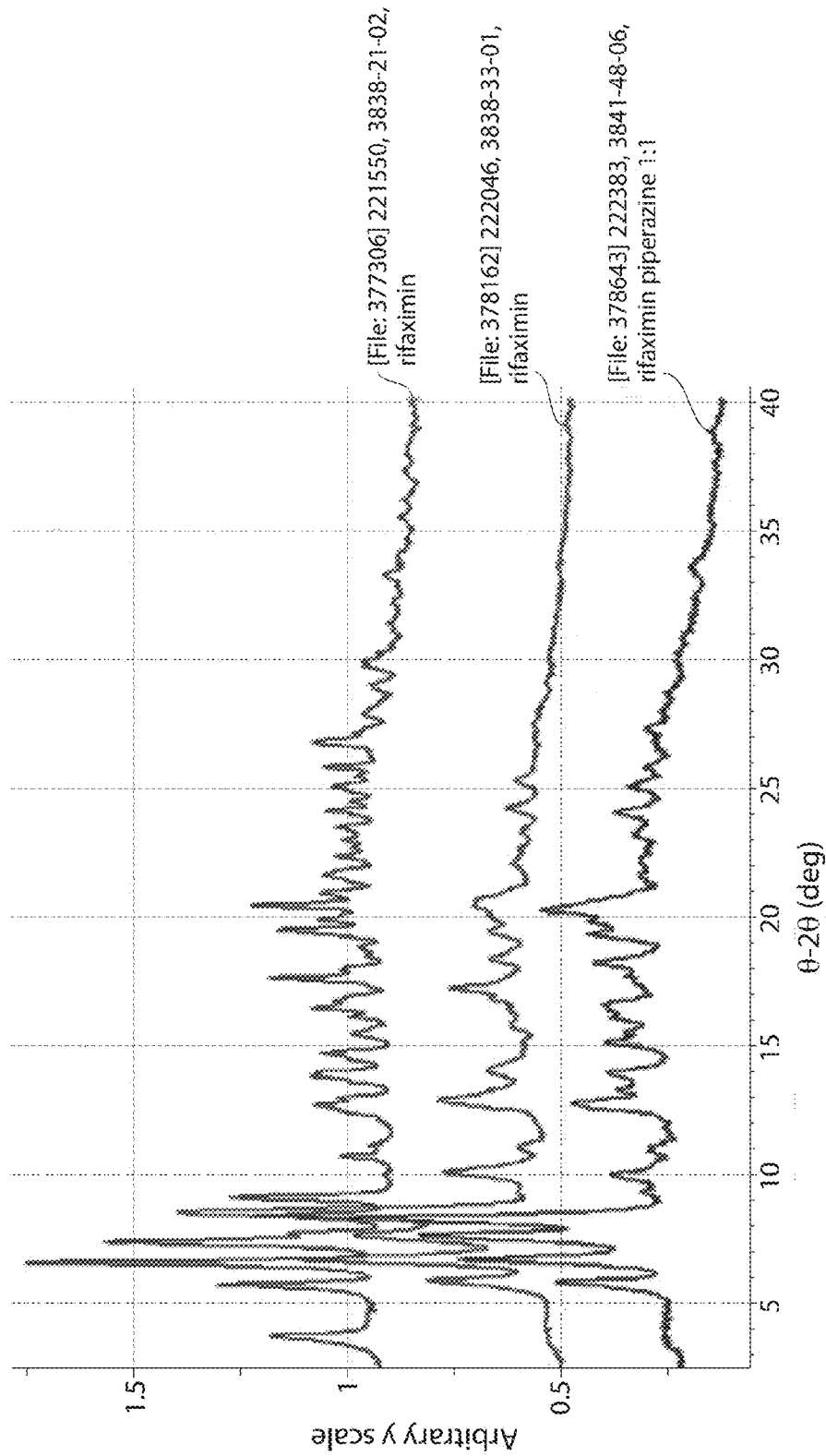
FIG. 20 shows an XRPD overlay of Rifaximin:piperazine cocrystal 2, pre- and post-vacuum drying. From top to bottom: cocrystal 2, pre-vacuum drying; similar to cocrystal 1+peak at ~17°θ, post-vacuum drying, cocrystal 1 (Inel pattern for comparison).

An experiment in which cocrystal 2 was vacuum dried at ambient temperature for 1 day gave material similar to cocrystal 1 with an additional peak at approximately 17° 2θ by XRPD (Table 16, FIG. 20).

TABLE 16

Vacuum Drying of Rifaximin:Piperazine Cocrystal 2

| Conditions | Habit/Description | Technique | Result |
|---|---|---|---|
| RT, 1 day | orange solids | XRPD | similar to cocrystal 1 + peak at ~17 °2θ |
|  |  | $^1$H NMR$^a$ | possible acetonitrile present |

$^a$Solvent: deuterated DMSO.

Proton NMR of this sample, also collected in deuterated DMSO (submitted prior to receiving the result of the initial NMR spectrum), also showed peak overlap in the region where acetonitrile would appear, proving inconclusive in measuring solvent content. Thus, subsequent NMR spectra were collected in deuterated chloroform to allow for peak separation to assess acetonitrile content.

Proton NMR of cocrystal 1, collected in deuterated chloroform, showed no solvent or water present, indicating it is a non-solvated/hydrated material (FIG. 31, Table 15). Based on this result and previous observations, cocrystal 1 was vapor stressed in acetonitrile for 7 days, resulting in conversion to cocrystal 2 (Table 17).

TABLE 17

Stressing of Rifaximin:Piperazine Cocrystal 1

| Conditions | Time | Habit/Description | XRPD Result |
|---|---|---|---|
| VS w/ ACN | 7 days | orange, slightly damp solids | cocrystal 2 |
| VS w/ ACN | 24 days | dark orange, slightly damp solids | cocrystal 1$^b$ (Panalytical) |
| VS w/ ACN | 7 days, sub-sample | — | cocrystal 2$^c$ (Panalytical) |

TABLE 17-continued

Stressing of Rifaximin:Piperazine Cocrystal 1

| Conditions | Time | Habit/Description | XRPD Result |
|---|---|---|---|
|  | of 4025-41-01 |  |  |
| ~75% RH | 3 days | dry orange solid | broad peaks, similar to cocrystal 1 + peak at ~5 °2θ |
|  | 1 week | dry orange solid | broad peaks, similar to cocrystal 1 + peak at ~5 °2θ |
|  | 2 weeks | dry orange solid | broad peaks, similar to cocrystal 1 + peak at ~5 °2θ |
| ~97% RH | 3 days | dry orange solid | API, Form β-1 |
|  | 1 week | dry orange solid | API, Form β-1 |

[[a.]]
$^b$Sample stood (capped) at ambient conditions for approximately 5-6 hours prior to XRPD analysis.
$^c$XRPD analysis was conducted quickly after isolating sample.

No solvent was present in this material by proton NMR; however, it is likely that the time lapse between XRPD and NMR analyses allowed for desolvation of cocrystal 2. A replication of this vapor stressing experiment, in which cocrystal 1 was stressed for 24 days, gave cocrystal 1 by XRPD, likely due again to a time lapse of approximately 5 to 6 hours between isolation of solids and XRPD analysis. It was concluded from these experiments that cocrystal 2 rapidly desolvates upon exposure to ambient conditions. Upon desolvation, cocrystal 2 appears to convert to cocrystal 1 after relatively short exposure time (ex. 5-6 hours), whereas longer exposure time (ex. 12 days) caused conversion to material similar to cocrystal 1, but exhibiting broad peaks with additional peaks at approximately 5 and 17° 2θ by XRPD (Table 15).

Figure 30:
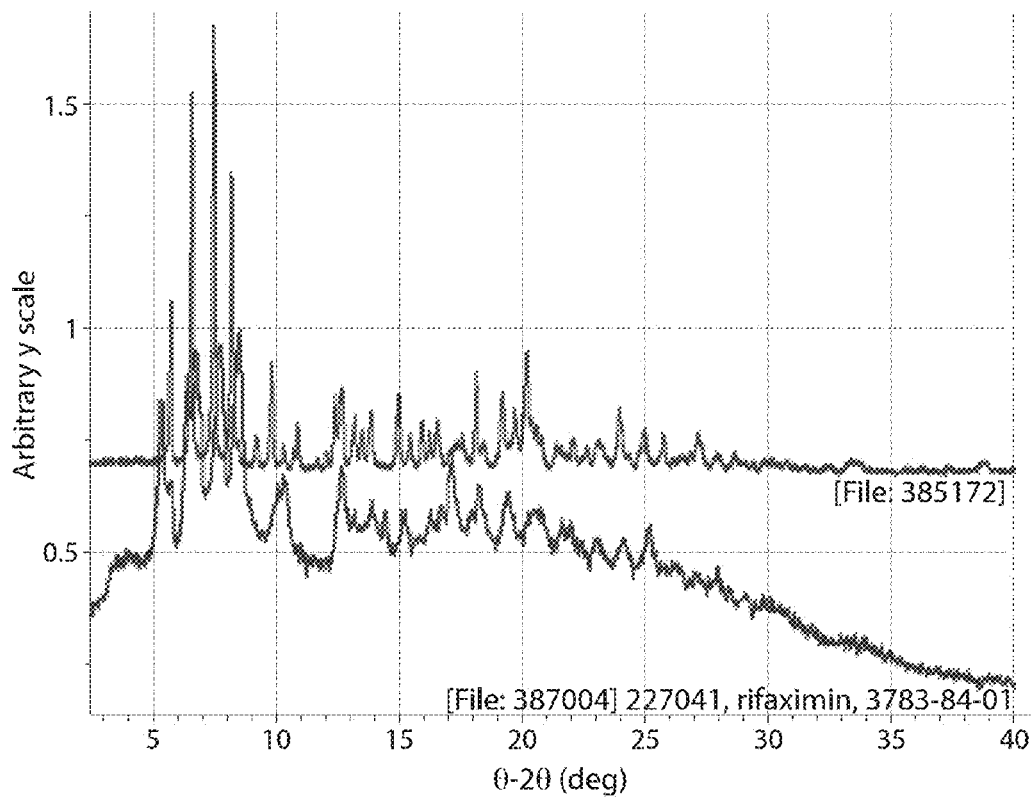
FIG. 30 shows an XRPD overlay of Rifaximin:piperazine cocrystal 1, post-DVS. Top to bottom: Pre-DVS cocrystal 1; post-DVS of the sample, broad peaks, similar to cocrystal 1+peaks at ~5 and 17° 2θ.

Cocrystal 1 was again stressed with acetonitrile vapor for 7 days, and XRPD and NMR analyses were conducted very quickly (~1 hr) after isolation of the solids. Cocrystal 2 resulted by XRPD, and proton NMR of the sample, conducted in deuterated chloroform, indicated 1 mole of acetonitrile was present (FIG. 30). Subsequent characterization of cocrystal 2 was conducted quickly after isolating vapor stressed samples.

Characterization of Cocrystals

Characterization data for the Rifaximin:piperazine cocrystals is summarized in Table 15. As previously discussed, cocrystal 2 is likely an acetonitrile solvate, and showed a tendency to desolvate upon exposure to ambient conditions. Please note in the first column of Table 15 that a cocrystal designated as "possible cocrystal 2" may have undergone form conversion between XRPD and additional characterization techniques. Similarly, "possible cocrystal 1" refers to a sample which is believed to have converted from cocrystal 2 to cocrystal 1 at ambient conditions. Finally, a designation of "likely cocrystal 2" refers to material analyzed quickly after isolation, but XRPD data was not acquired to confirm the form.

Cocrystal 1

Figure 24:
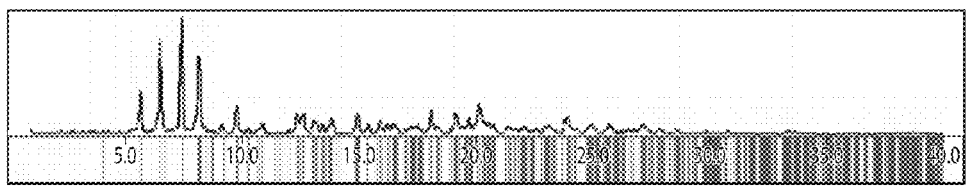
FIG. 24 is an indexing solution for Rifaximin:piperazine cocrystal 1. The bars indicate allowed reflections based on the unit cell dimensions and the assigned space group ($P2_12_11_1$, #19).
Figure 25:
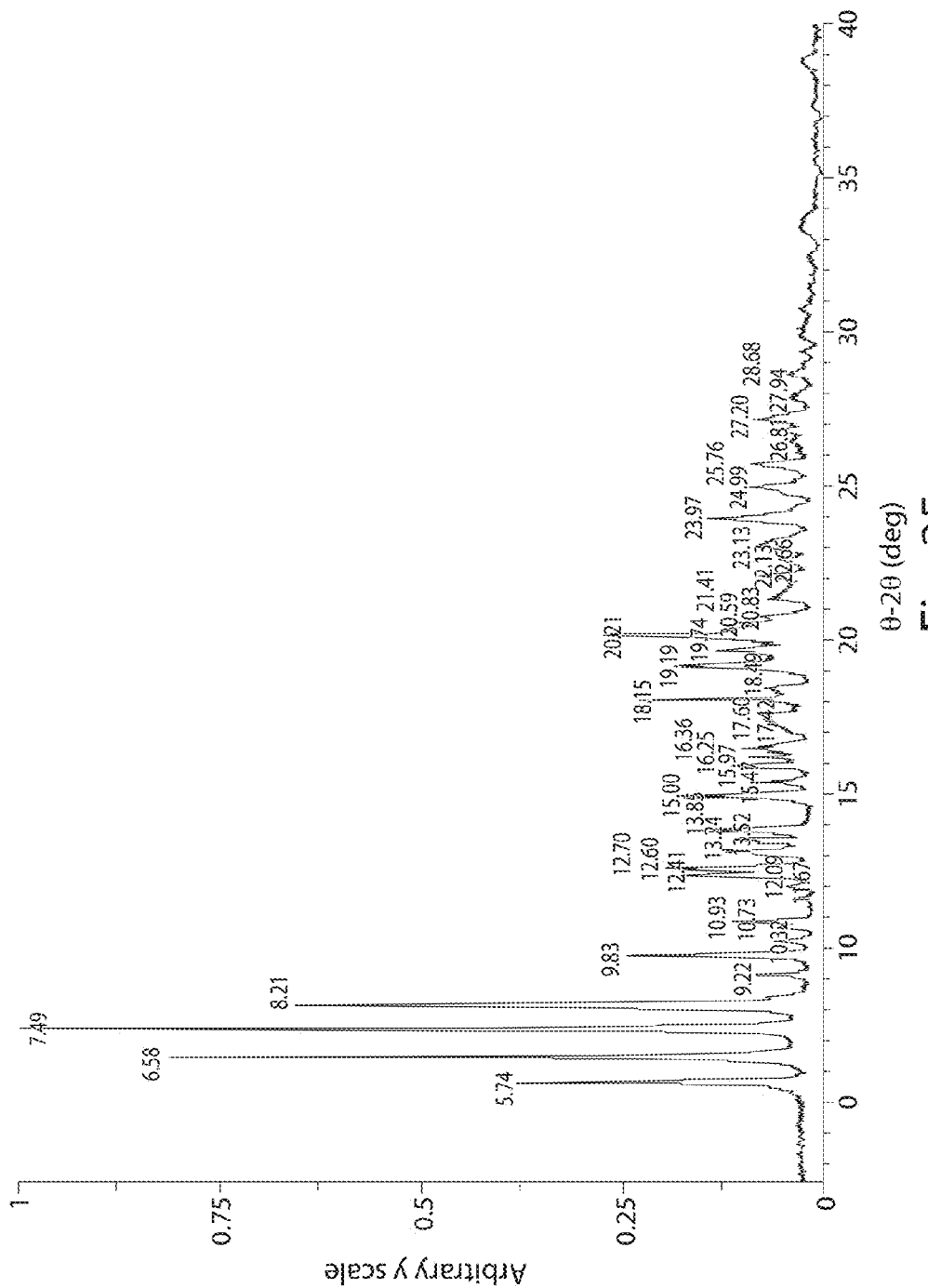
FIG. 25 shows labeling of XRPD peak for Rifaximin:piperazine cocrystal 1. Note that the peak labels in this image are meant as a visual aid. See FIG. 26 for accurate 2θ positions.

A high-resolution XRPD pattern of cocrystal 1 is presented in FIG. 19. The pattern was successfully indexed, indicating it consists of a pure, single crystalline phase (FIG. 24). Peak picking of the XRPD pattern was performed. One Panalytical pattern and one Inel pattern were analyzed for this material, and therefore preferred orientation and particle statistic effects could be assessed through comparison of multiple patterns. Minor preferred orientation effects were observed, though the patterns appeared to be in relatively good agreement. Observed peaks are shown in FIG. 25 and FIG. 26, and representative peaks are listed in FIG. 27.

Figures 27, 28:
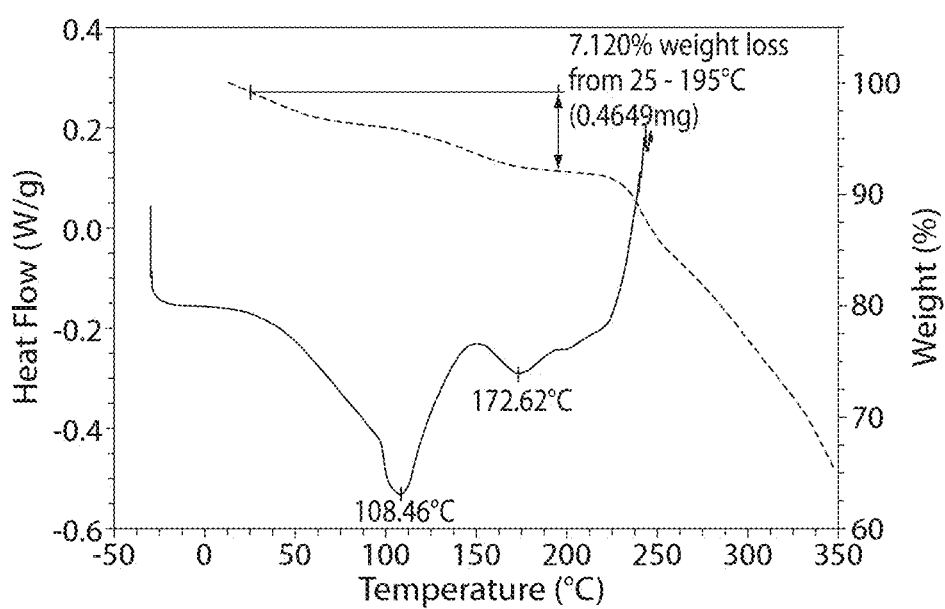
FIG. 27 is a representative list of observed XRPD peaks for Rifaximin:piperazine cocrystal 1.
FIG. 28 shows an exemplary DSC and TGA overlay of Rifaximin:piperazine cocrystal 1.

Broad endotherms in the DSC thermogram combined with constant weight loss by TGA likely indicate that the cocrystal falls apart upon heating (FIG. 28).

Figure 29:
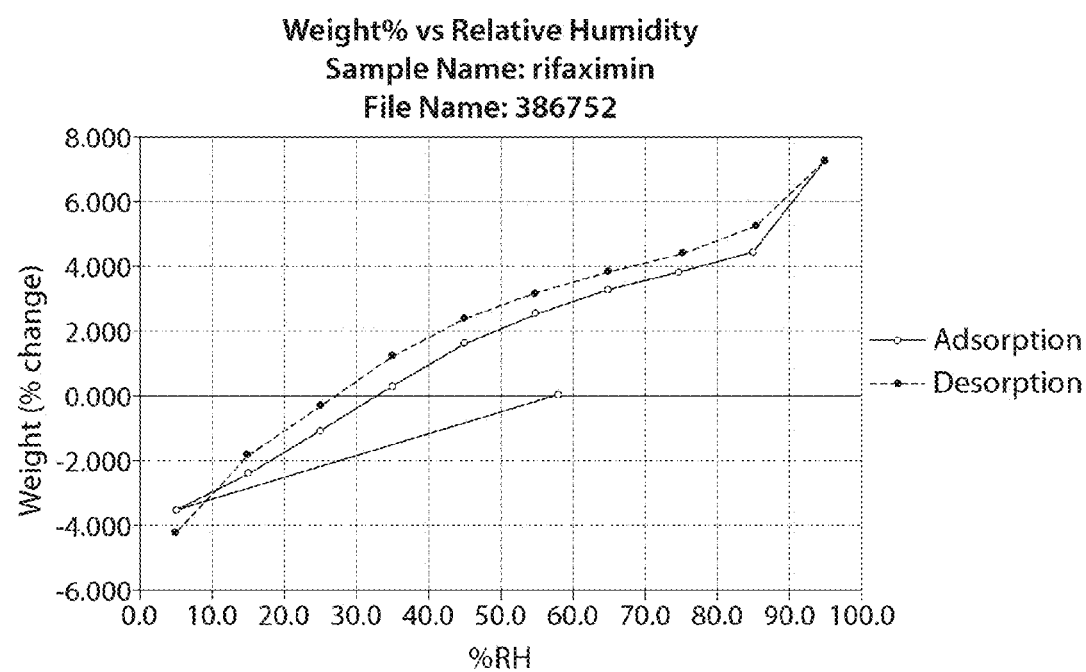
FIG. 29 shows an exemplary DVS curves for Rifaximin:piperazine cocrystal 1.

Analysis by DVS indicates the material is quite hygroscopic (FIG. 29). Approximately 11% weight gain was observed upon sorption from 5% to 95% RH, and all of that weight was lost on desorption. XRPD of the post-DVS material exhibits broad peaks, similar to cocrystal 1 plus peaks at approximately 5 and 17° 2θ (FIG. 15).

A proton NMR spectrum of cocrystal 1 is given in FIG. 31. The spectrum indicates a 2:1 Rifaximin:piperazine stoichiometry with no solvents present. The presence of small peaks throughout the spectrum indicates partial decomposition of the molecule in this solvent.

Figure 21:
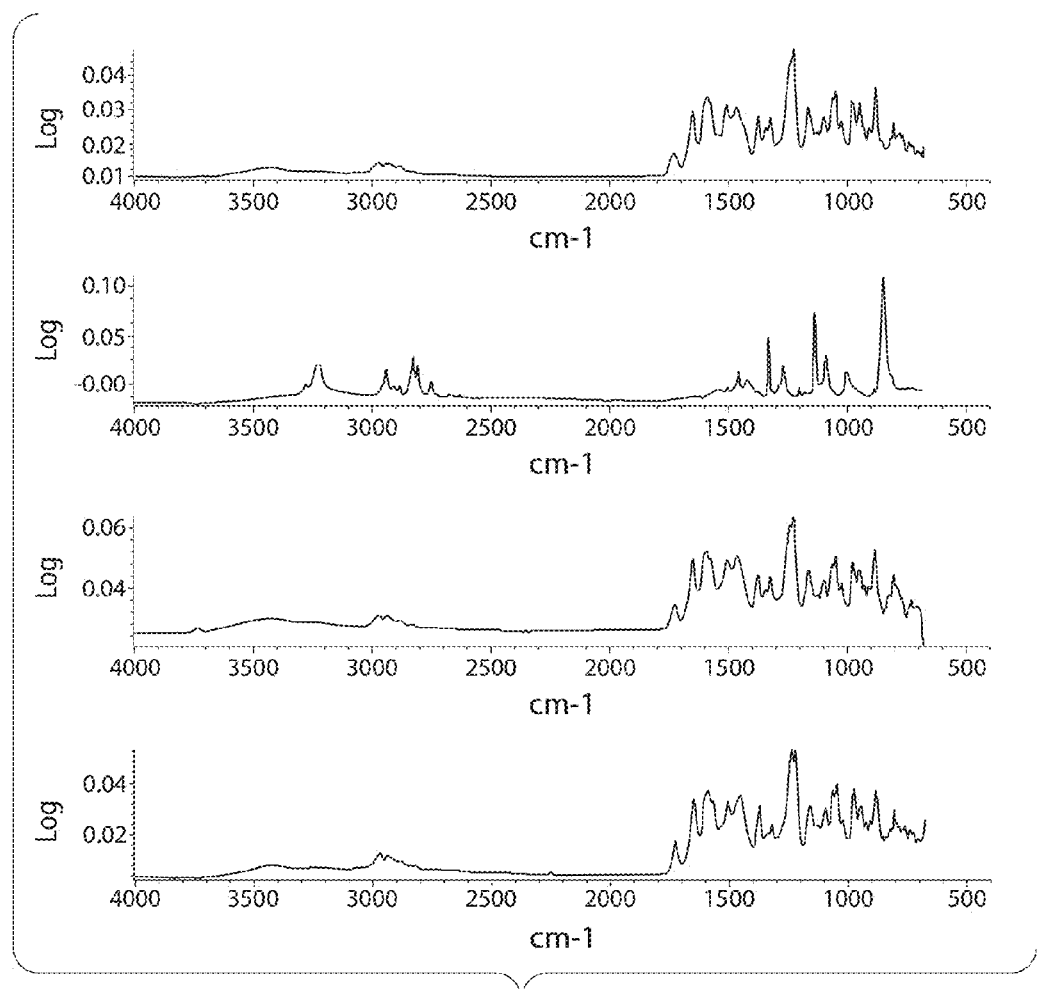
FIG. 21 show an overlay of IR spectra for Rifaximin, piperazine, and cocrystals. From top to bottom: Rifaximin, as received, piperazine, as received, Rifaximin:piperazine cocrystal 1, Rifaximin:piperazine likely cocrystal 2.
Figure 22:
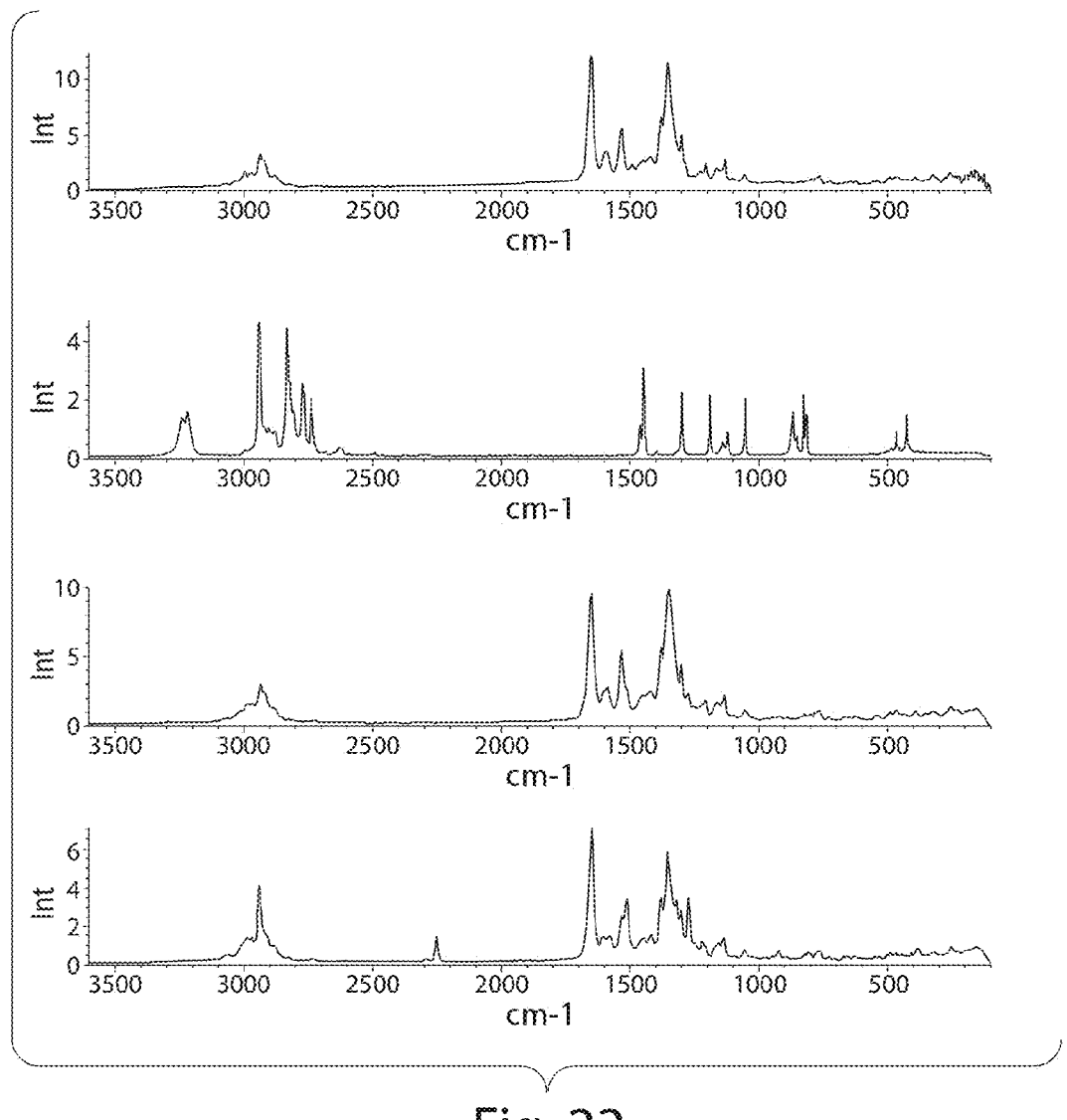
FIG. 22 depicts an overlay of Raman spectra for Rifaximin, piperazine, and cocrystals. From top to bottom: Rifaximin, as received, piperazine, as received from Sigma-Aldrich, Rifaximin:piperazine cocrystal 1, Rifaximin:piperazine likely cocrystal 2.
Figure 23:
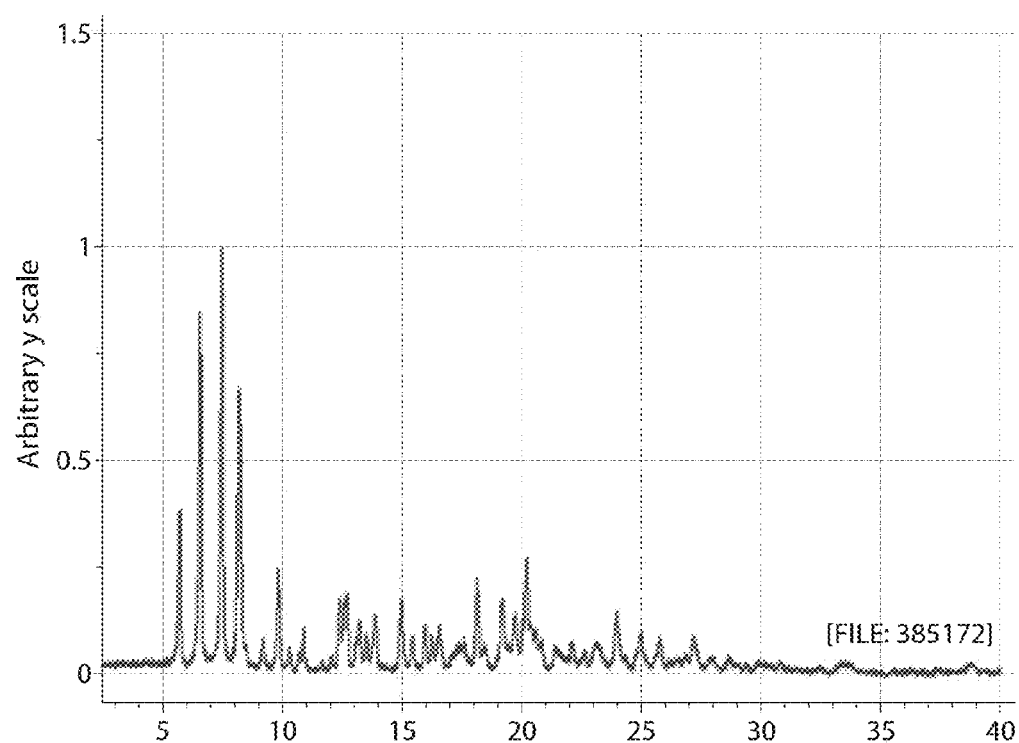
FIG. 23 shown an exemplary XRPD of Rifaximin:piperazine cocrystal 1.
Figure 32:
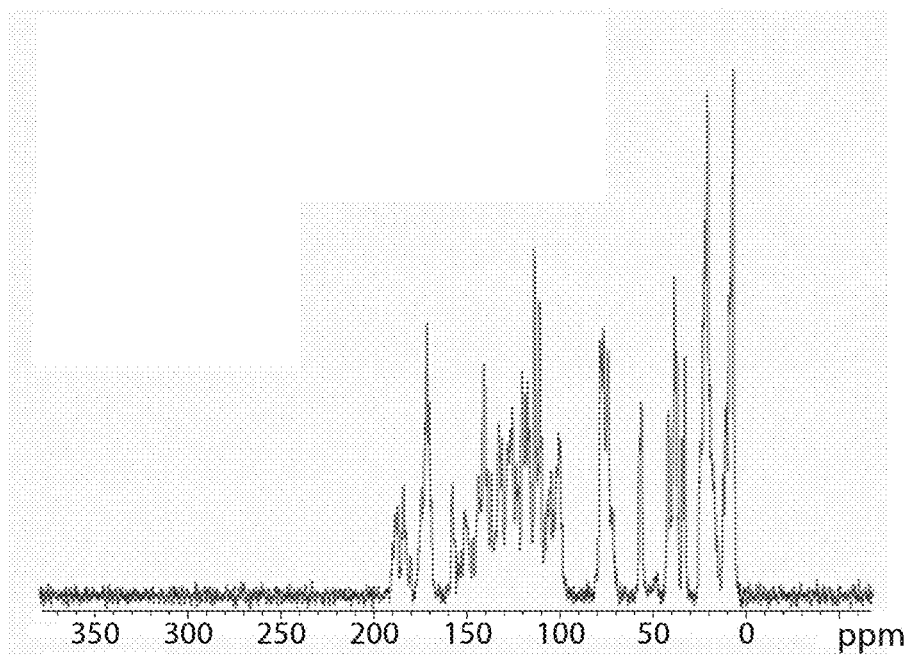
FIG. 32 is an SSNMR of Rifaximin:piperazine cocrystal 1.
Figure 33:
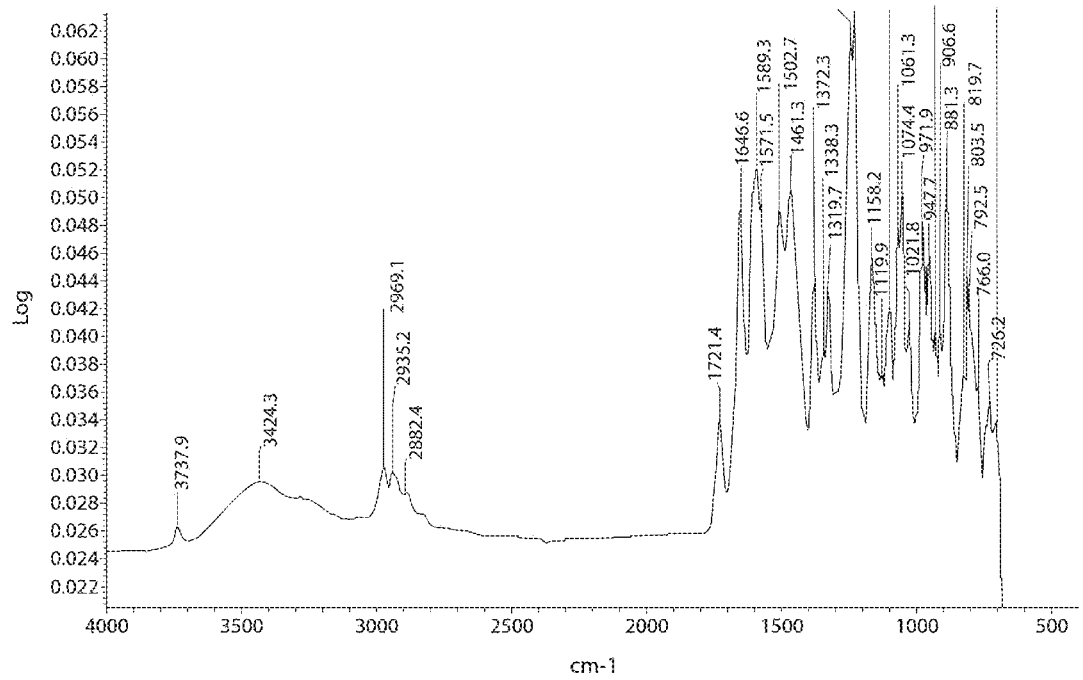
FIG. 33 shows an IR spectrum of Rifaximin:piperazine cocrystal 1.
Figure 35:
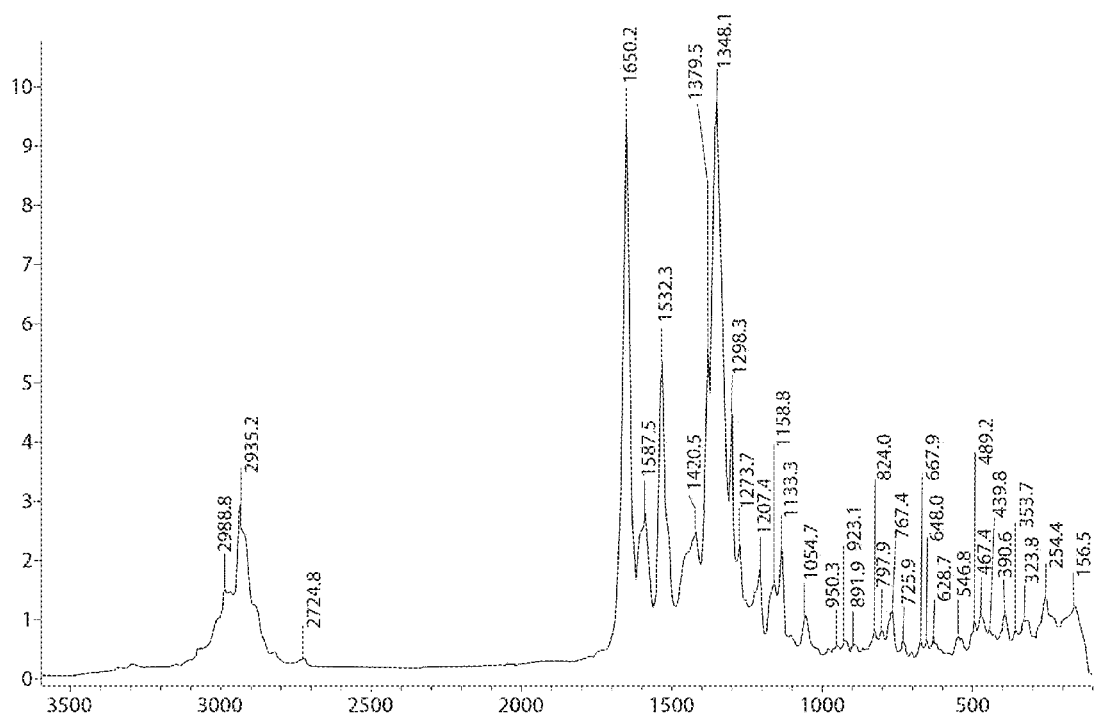
FIG. 35 is an exemplary Raman spectrum of Rifaximin:piperazine cocrystal 1.

A solid-state NMR spectrum of the material is unique to the cocrystal, by comparison with that of the starting materials (FIG. 32). IR and Raman spectra were collected and subjected to peak picking (FIG. 33 through FIG. 36). Overlays of the IR and Raman spectra with those of the starting materials and cocrystal 2 are presented in FIG. 21 and FIG. 22.

Cocrystal 2

Figure 37:
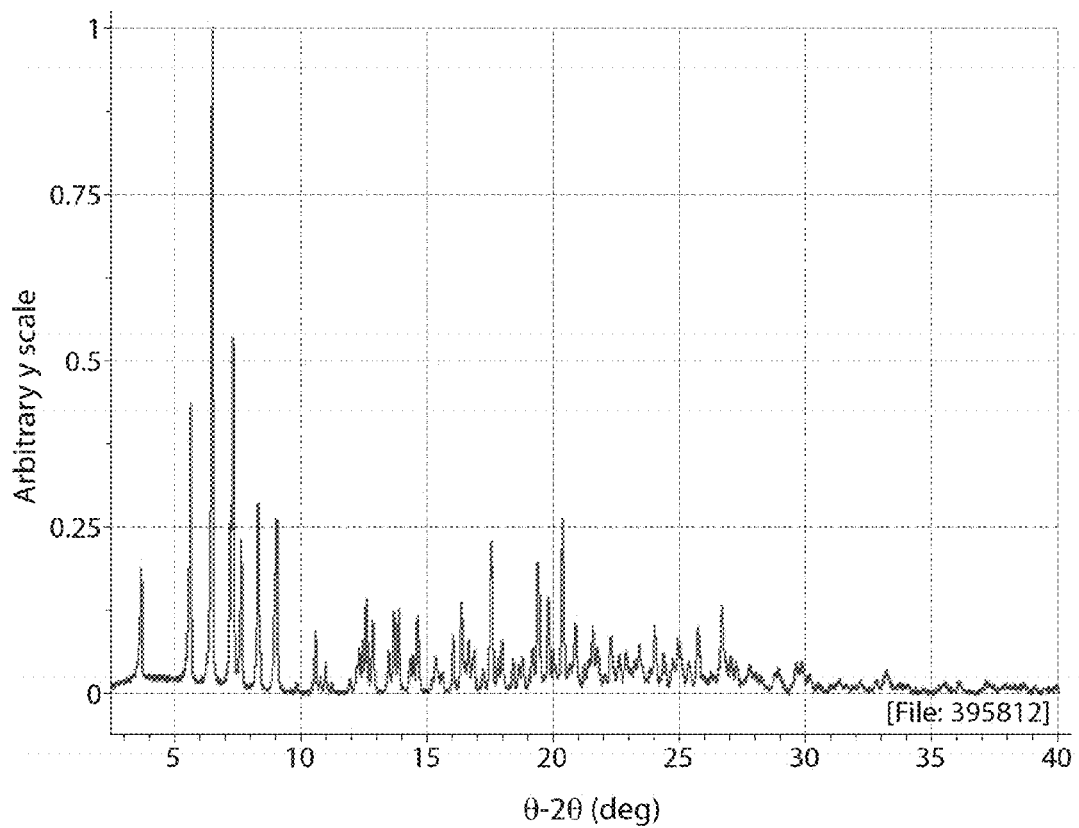
FIG. 37 is an exemplary XRPD of Rifaximin:piperazine cocrystal 2.
Figure 38:
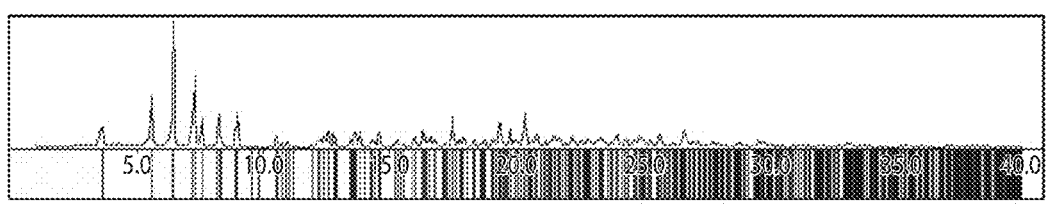
FIG. 38 is an indexing solution for Rifaximin:piperazine cocrystal 2. The bars indicate allowed reflections based on the unit cell dimensions and the assigned space group (P2$_1$2$_1$2$_1$, #19).
Figure 39:
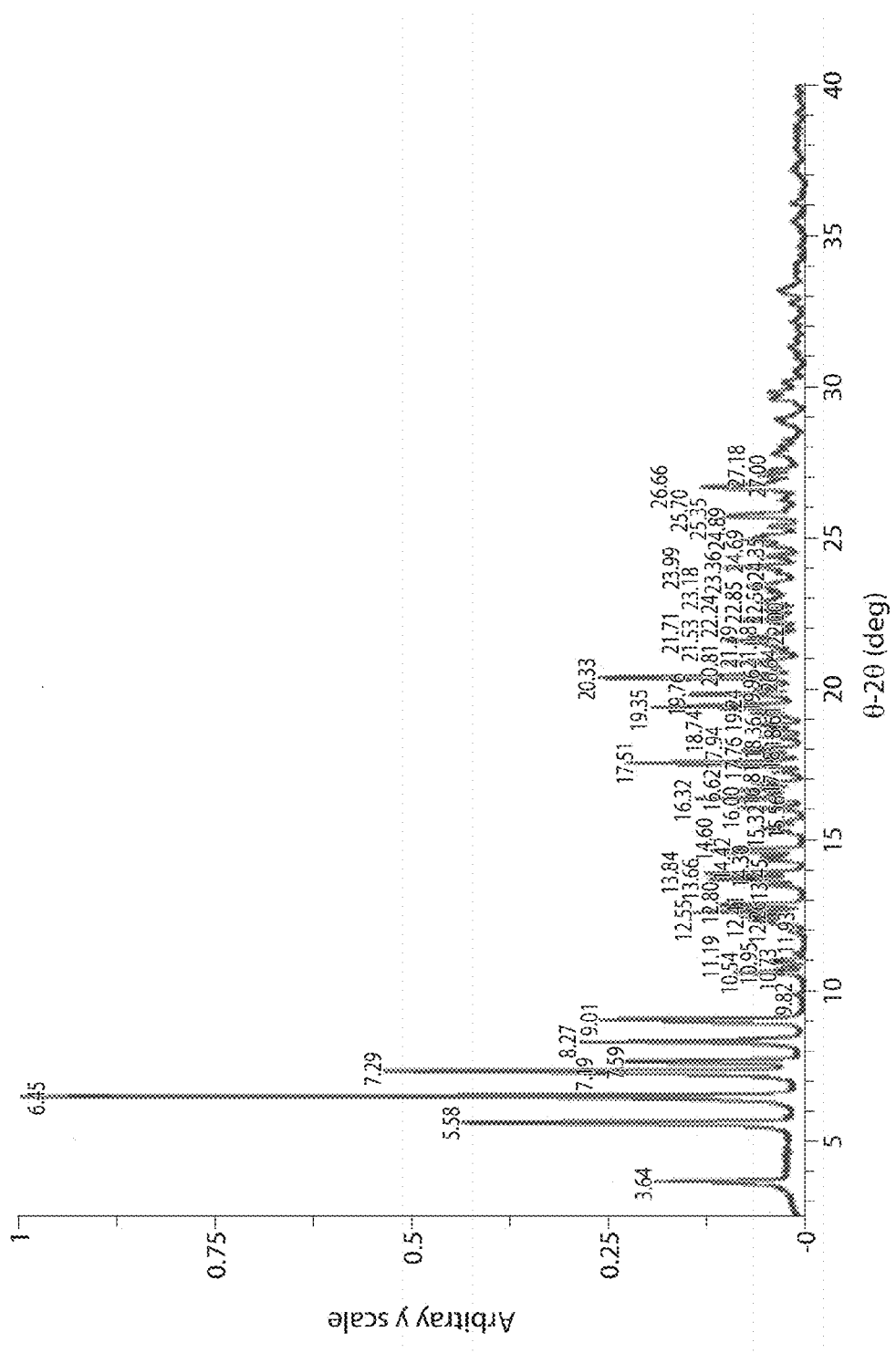
FIG. 39 shows an XRPD labeled with peaks for Rifaximin: piperazine cocrystal 2.

A high-resolution XRPD pattern of cocrystal 2 is given in FIG. 37. This pattern, like that for cocrystal 1, was also successfully indexed, indicating it consists of a pure, single crystalline phase of solvated material (FIG. 38). Peak picking of the XRPD pattern was performed. One Panalytical pattern and one Inel pattern was analyzed for this material, and therefore preferred orientation and particle statistic effects could be assessed through comparison of multiple patterns. Good agreement between patterns indicates that the observed patterns are free of orientation and particle statistic effects. Observed peaks are shown in FIG. 39 and FIG. 40, and representative peaks are listed in FIG. 41.

Figures 41, 42:
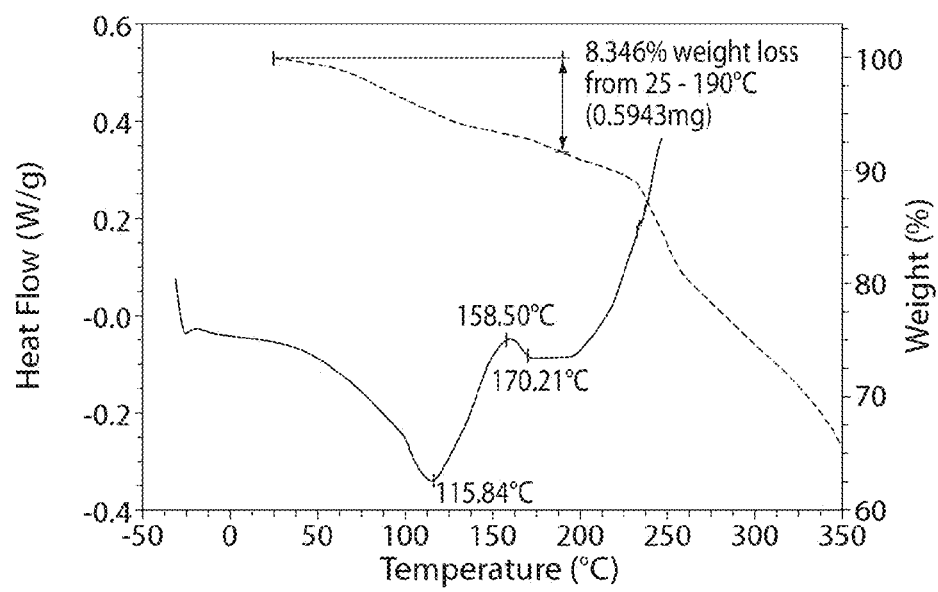
FIG. 41 is a representative list of observed XRPD peaks for Rifaximin:piperazine cocrystal 2.
FIG. 42 is an exemplary DSC and TGA overlay of Rifaximin:piperazine cocrystal 2.

For material that is possibly cocrystal 2, a constant weight loss of approximately 8.35% observed by TGA from approximately 25 to 190° C., coupled with a very broad endotherm at approximately 116° C. in the DSC thermogram, likely indicates decomposition of the cocrystal (FIG. 42).

Proton NMR of cocrystal 2 indicates the material consists of a 2:1 Rifaximin:piperazine cocrystal with approximately 1 mole of acetonitrile (FIG. 43). Similar to the spectrum of cocrystal 1, the presence of small peaks throughout the spectrum indicates partial decomposition of the molecule in this solvent.

Figure 44:
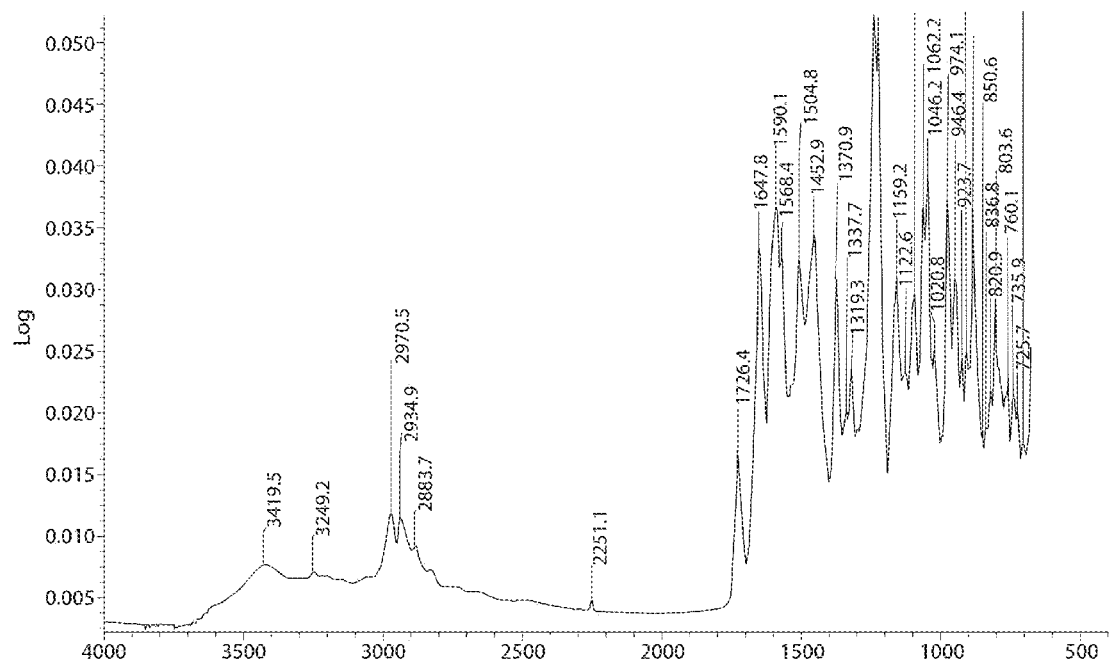
FIG. 44 is an exemplary IR spectrum of Rifaximin:piperazine cocrystal 2.
Figure 46:
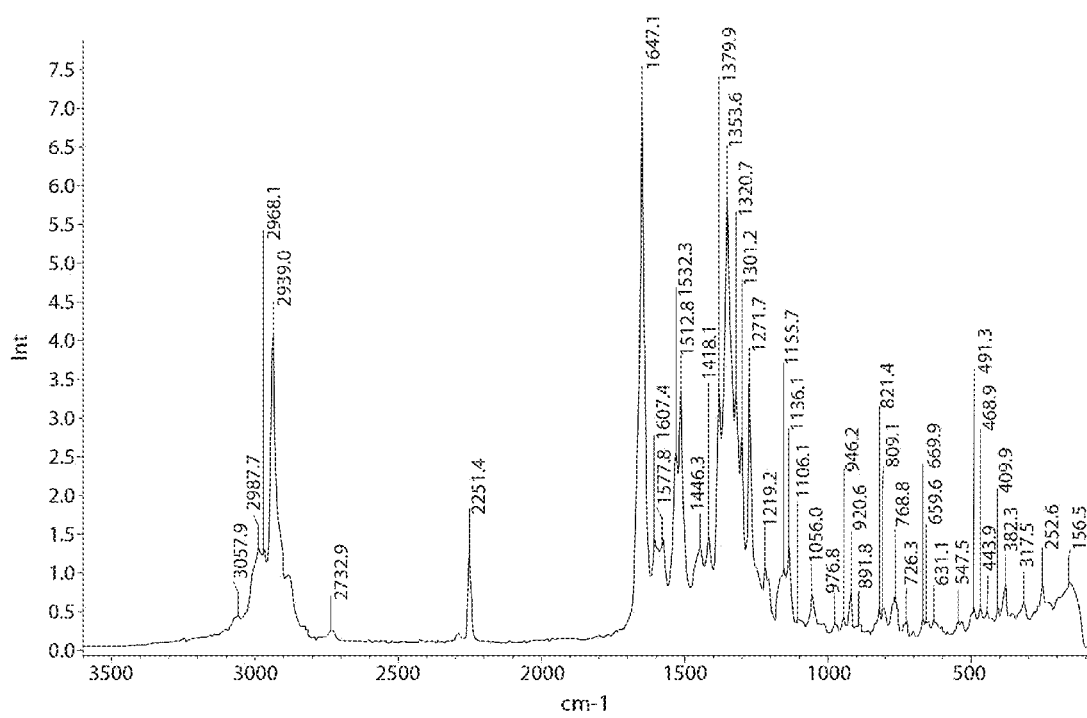
FIG. 46 is an exemplary Raman spectrum of Rifaximin: piperazine cocrystal 2.

An IR spectrum of cocrystal 2, with labeled peaks, is presented in FIG. 44. Observed and characteristic peaks are listed in FIG. 45. While the majority of IR peaks were similar to those of Rifaximin, two characteristic peaks, unique to cocrystal 2, were observed. Similarly, a Raman spectrum, also with labeled peaks, is given in FIG. 46, and observed and characteristic peak lists are shown in FIG. 47. Several peaks unique to cocrystal 2 (e.g., characteristic peaks) were observed in the Raman spectrum. Overlays of the IR and Raman spectra with those of the starting materials and cocrystal 1 are presented in FIG. 21 and FIG. 22.

Indexing of Rifaximin:Piperazine Cocrystal 1

Indexing and structure refinement are computational studies. The indexed XRPD pattern of Rifaximin:piperazine cocrystal 1 is illustrated in FIG. 24. Agreement between the allowed peak positions, marked with bars in FIG. 24, and the observed peaks indicates a consistent unit cell determination. Successful indexing of the pattern indicates that the sample is composed primarily of a single crystalline phase. Space groups consistent with the assigned extinction symbol, unit cell parameters, and derived quantities are tabulated in Table 18.

TABLE 18

Indexing Solution and Derived Quantities for Rifaximin:Piperazine Cocrystal 1

| Form/Pattern | Rifaximin-Piperazine cocrystal |
| --- | --- |
| Family and Space Group | Orthorhombic $P2_12_12_1$ (#19) |
| Z'/Z | 1/4 |
| a (Å) | 14.116 |
| b (Å) | 16.477 |
| c (Å) | 42.795 |
| α (deg) | 90 |
| β (deg) | 90 |
| γ (deg) | 90 |
| Volume (Å³/cell) | 9953.7 |
| V/Z (Å³/formula unit) | 2488.4 |
| Assumed Composition[a] | $2(C_{43}H_{51}N_3O_{11}) \cdot C_4H_{10}N_2$ |
| Density (g/cm³)[a] | 1.11 |
| Weight Fraction Solvent (%)[a] | N/A |

[a]Density and weight fraction solvent are based on the assumed composition.

Indexing of Rifaximin:Piperazine Cocrystal 2

Indexing and structure refinement are computational studies. The indexed XRPD pattern of the Rifaximin:piperazine cocrystal 2 (ACN solvate) is illustrated in FIG. 38. Agreement between the allowed peak positions, marked with the bars in FIG. 38, and the observed peaks indicates a consistent unit cell determination. Successful indexing of the pattern indicates that the sample is composed primarily of a single crystalline phase. Space groups consistent with the assigned extinction symbol, unit cell parameters, and derived quantities are tabulated in Table 19. The indexed unit cell volume allows up to six moles of ACN per formula unit, assuming a 2:1 Rifaximin:piperazine stoichiometry.

TABLE 19

Indexing Solution and Derived Quantities for Rifaximin:Piperazine Cocrystal 2

| Form/Pattern | Rifaximin-Piperazine ACN Solvate |
| --- | --- |
| Family and Space Group | Orthorhombic $P2_12_12_1$ (#19) |
| Z'/Z | 1/4 |
| a (Å) | 14.234 |
| b (Å) | 16.713 |
| c (Å) | 48.465 |
| α (deg) | 90 |
| β (deg) | 90 |
| γ (deg) | 90 |
| Volume (Å³/cell) | 11,529.5 |
| V/Z (Å³/formula unit) | 2882.4 |
| Assumed Composition[a] | $2(C_{43}H_{51}N_3O_{11}) \cdot C_4H_{10}N_2 \cdot x(CH_3CN)$ 0 ≤ x ≤ 6 |
| Density (g/cm³)[a] | 0.96 ≤ y ≤ 1.10 |
| Weight Fraction Solvent (%)[a] | 0 ≤ z ≤ 12.9 |

[a]Density and weight fraction solvent are based on the assumed composition.

Relative Humidity Stressing of Cocrystal 1

Figure 48:
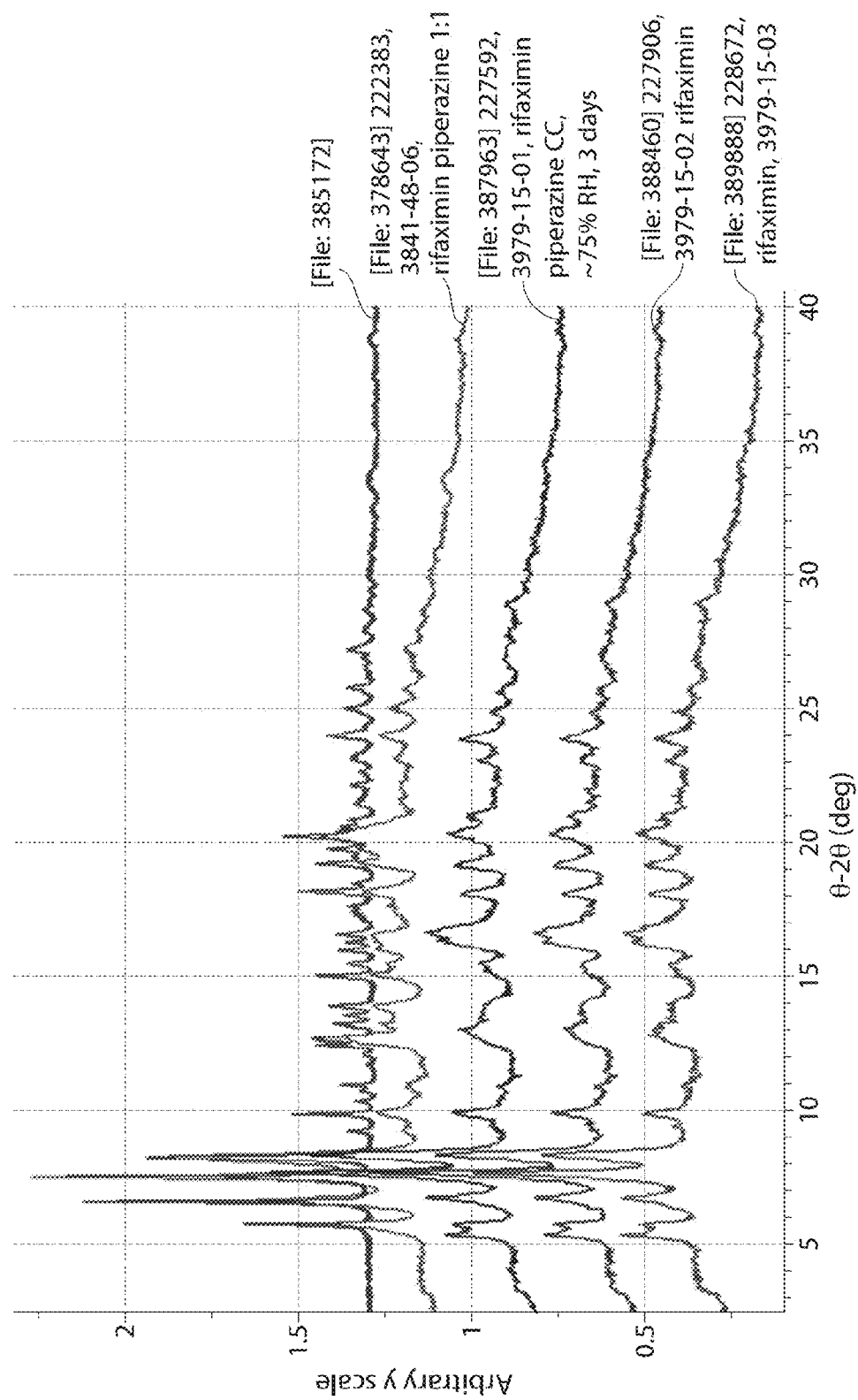
FIG. 48 is an exemplary XRPD overlay of Rifaximin: piperazine cocrystal, post-RH stressing. From top to bottom: cocrystal 1, unstressed (Panalytical XRPD); cocrystal 1 (Inel XRPD); broad peaks, similar to cocrystal 1+peak at ~5° 2θ, 3 days at ~75% RH; broad peaks, similar to cocrystal 1+peak at ~5° 2θ, 1 week at ~75% RH; broad peaks, similar to cocrystal 1+peak at ~5°2θ, 2 weeks at ~75% RH.
Figure 49:
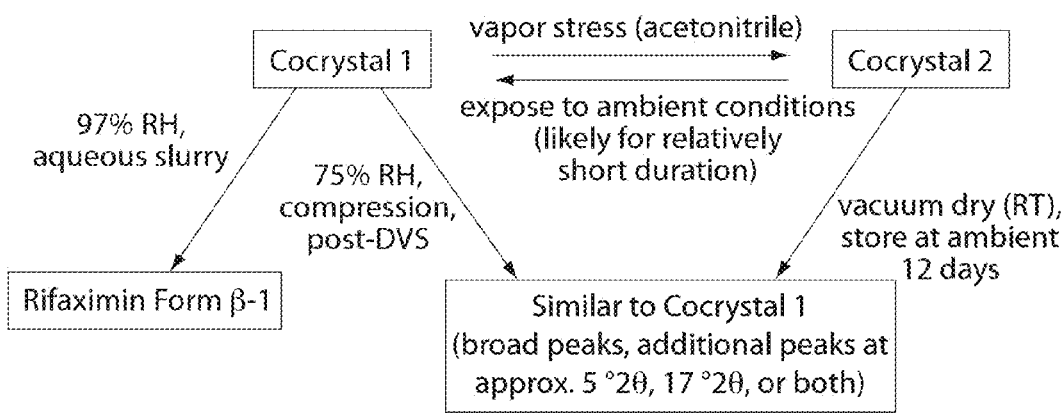
FIG. 49 is an a schematic showing conversion and interconversion schemes of Rifaximin:piperazine cocrystals 1 and 2.
Figure 50:
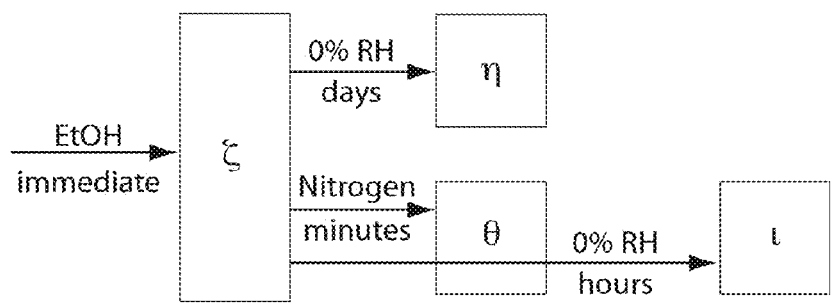
FIG. 50 shows a flow chart depicting the ethanolate/hydrate system and the conversion of rifaximin form ξ to forms η, θ, and ι.
Figure 54:
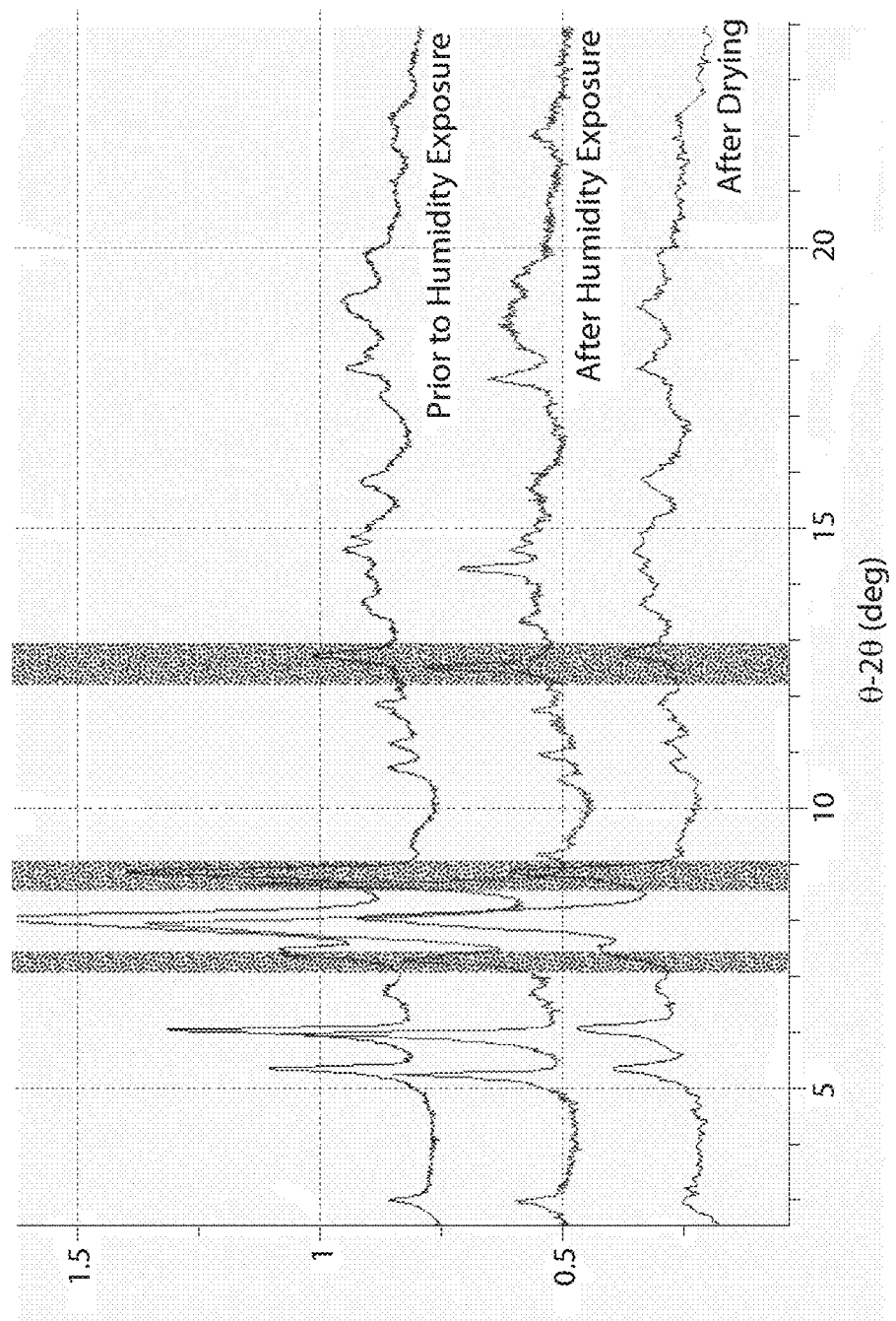
FIG. 54 is an exemplary XRPD pattern of rifaximin Form η prior to humidity exposure, after humidity exposure and after drying.
Figure 55:
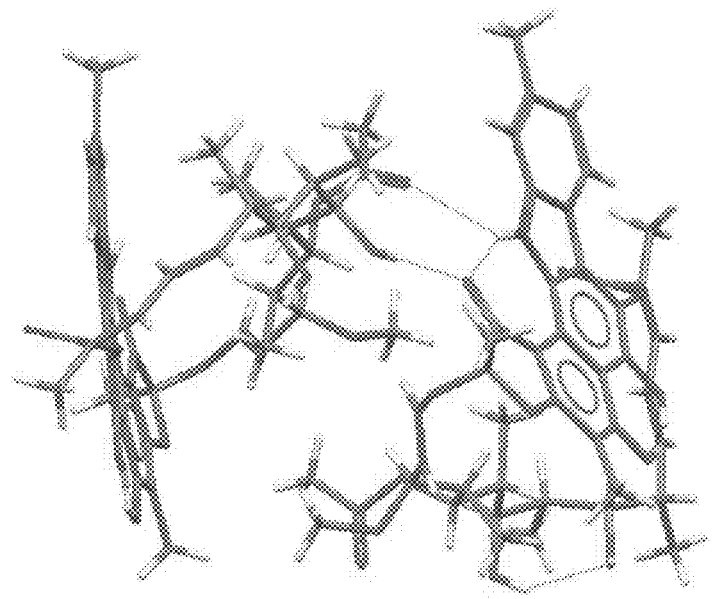
FIG. 55 shows rifaximin dimers created from hydrogen bonding.
Figure 56:
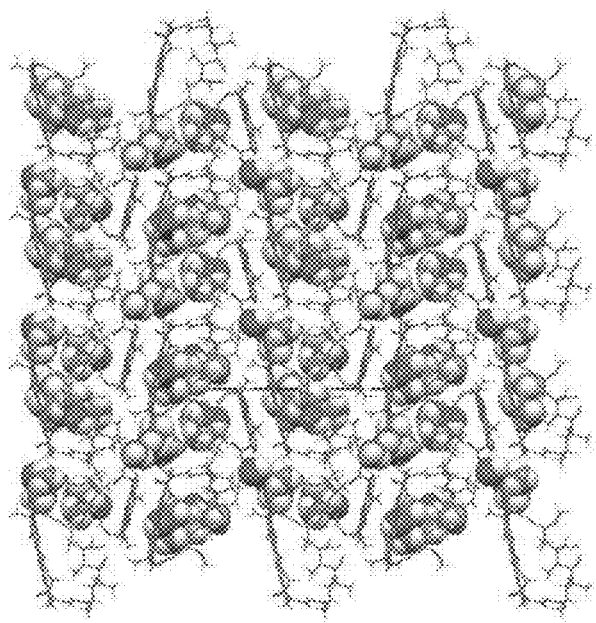
FIG. 56 shows solvent molecules viewed down the a axis.
Figure 57:
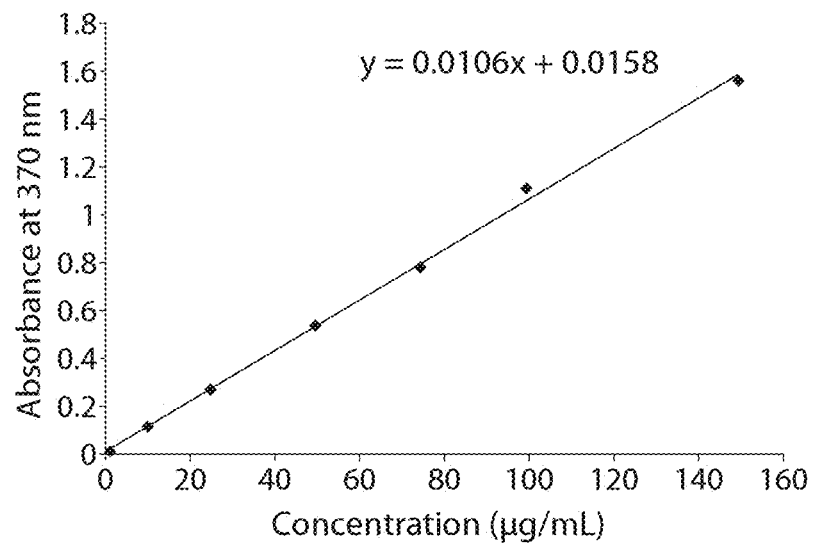
FIG. 57 is a linearity plot of rifaximin standards in sodium acetate buffer medium, with acetonitrile.
Figure 58:
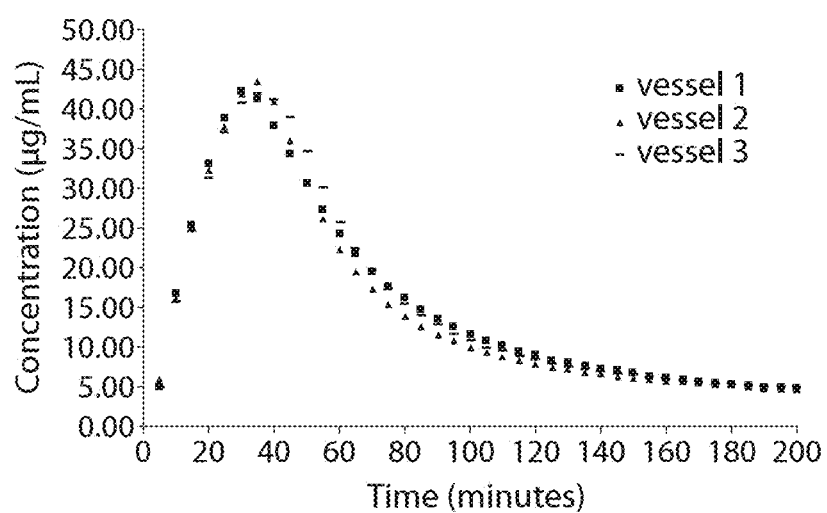
FIG. 58 is a linearity plot of rifaximin standards in sodium acetate buffer medium, with acetonitrile.
Figure 59:
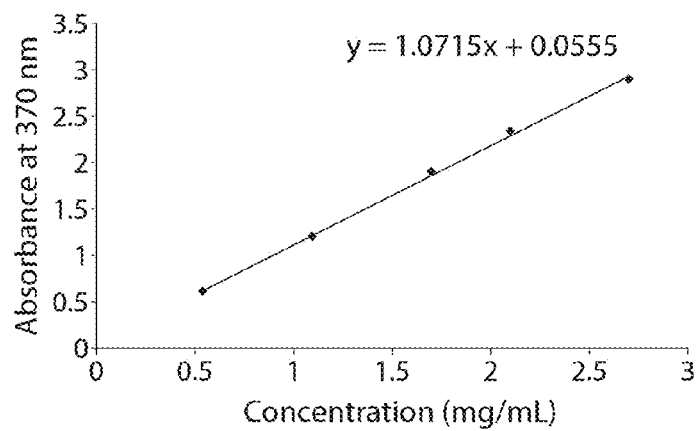
FIG. 59 is a linearity plot of rifaximin standards in sodium phosphate buffer with 0.45% sodium dodecyl sulfate medium, with acetonitrile.

Cocrystal 1 was stressed at approximately 75% and 97% relative humidity (RH) at ambient temperature, and pulls were made after 3 days, 1 week, and 2 weeks (Table 17). Dry orange solids were observed at each condition. Conversion to Rifaximin Form β-1 by XRPD was observed at 97% RH for the 3-day and 1-week pulls; solids isolated after 2 weeks were not analyzed and were assumed to have converted as well. The 3-day, 1-week, and 2-week pulls at 75% RH all showed the same XRPD pattern: broad peaks, similar to cocrystal 1 with an additional peak at approximately 5° 2θ (FIG. 48). These experiments show that the cocrystal is not stable at elevated RH conditions.

Determining the Suitability of Cocrystal 1 for Solubility Studies

In order to be able to measure the aqueous solubility (equilibrium or kinetic) of a cocrystal, it should remain intact upon exposure to aqueous conditions for some duration. If it dissociates or changes forms quickly upon contact with water, intrinsic dissolution may be introduced as an alternative to solubility, in which dissolution of a pellet of the cocrystal is measured; however, the cocrystal must not change form upon compression.

In the case of the Rifaximin:piperazine cocrystal 1, conversion to Rifaximin Form β-1 was observed after 5 minutes (as well as 3 hours and 7 hours) of slurrying in water; thus, aqueous solubility of the cocrystal could not be measured (Table 20).

TABLE 20

Aqueous Slurries of Rifaximin:Piperazine Cocrystal 1

| Conditions | Habit/Description | XRPD Result |
| --- | --- | --- |
| recover filtrate, vacuum filter (nylon filter), dry under reduced pressure ~5 min. | small amount solid collected; bright orange, aggregates and very fine particles, not birefringent | API, Form β-1 |
| vacuum filter (nylon filter), dry under reduced pressure ~4 min. (N₂ blown over filter for ~1 min.) | bright orange, aggregates and tiny particles, not birefringent | API, Form β-1 |
| vacuum filter (nylon filter), dry under reduced pressure and N₂ gas ~3 min. | bright orange, aggregates and tiny particles, not birefringent | API, Form β-1 |

When cocrystal 1 was pressed into a pellet, additional peaks at approximately 5 and 17° 2θ were observed by XRPD, and the material was low crystalline (Table 21). Since the cocrystal form changed upon compression, the intrinsic dissolution rate could not be measured either.

TABLE 21

Compression Experiment for Rifaximin:Piperazine Cocrystal 1

| Conditions | Habit/Description | XRPD Result |
| --- | --- | --- |
| 1000 psi, 1 min. | dark orange and brown solids | cocrystal 1 + peaks at ~5 and 17 °2θ, l.c. |

Attempted Growth of Single Crystals

Numerous attempts were made to grow single crystals of the Rifaximin:piperazine cocrystals utilizing vapor diffusion, sonication, solvent/antisolvent, slurry, and cooling techniques, but all experiments were unsuccessful due to the formation of too small and/or fractured crystals (Table 14 and Table 22).

TABLE 22

Single Crystal Growth Attempts for Rifaximin Piperazine Cocrystal

| Molar Ratio[a] | Solvent System | Conditions | Habit/Description[b] | Singles |
| --- | --- | --- | --- | --- |
| 2:1 | DCM | sonicated to solution, ACN added, refrigerated | blades, plates, birefringent | Yes; fractured |
| 2:1 | DCM | sonicated to solution, multiple vial VD w/ ACN | blades, birefringent | Yes; fractured, dissolved |
| 2:1 | DCM | sonicated to solution, VD w/ ACN | blades, unknown morphology, birefringent | Yes; fractured |
| 2:1 | DCM | sonicated to solution, VD w/ ACN | blades, plates, birefringent | Yes; fractured |
| 2:1 | DCM | sonicated to solution, vial coated with mineral oil, VD w/ ACN | blades, birefringent | Yes; fractured |

[a]Ratio given is API: coformer.
[b]Samples observed in-situ and aliquots transferred to glass slides with needles, picks and pipets, mounting in Paratone-N and mineral oils. Observations of "not birefringent" indicate also that no extinction was observed.

Both forms of the Rifaximin:piperazine cocrystal resulted only from acetonitrile-containing solvent systems, and both occur in a 2:1 Rifaximin:piperazine stoichiometric ratio by proton NMR. Thermal data indicates that both cocrystals fall apart upon heating.

Cocrystal 1 is non-solvated/hydrated, and is quite hygroscopic by DVS. XRPD of the post-DVS material showed conversion to a material similar to cocrystal 1 plus two additional peaks. Stressing of the cocrystal at approximately 97% RH induced conversion to Rifaximin Form β-1 after 3 days. Upon stressing at approximately 75% RH, solids converted to material similar to that of the post-DVS material, but with only one additional peak by XRPD.

Cocrystal 2 contains approximately 1 mole of acetonitrile by proton NMR. The material rapidly desolvates (likely to cocrystal 1 or material similar to cocrystal 1) upon exposure to ambient conditions. Conversely, cocrystal 1 converts to cocrystal 2 upon vapor stressing in acetonitrile.

XRPD patterns of both cocrystals were successfully indexed, indicating that each consists primarily of a single crystalline phase.

IR and Raman spectra for both cocrystals and the starting materials, as well as solid-state NMR spectra for cocrystal 1 and both starting materials, were collected. The XRPD patterns and IR and Raman spectra for both cocrystals were peak picked.

Procedures

Rifaximin:Piperazine Cocrystal 1

Rifaximin (2.0234 g) was dissolved in acetonitrile (8 mL) with sonication. The solution was then added to a vial containing piperazine (0.0467 g) with stirring, resulting immediately in a clear red solution (5:1 molar ratio Rifaximin:piperazine). After stirring for approximately 1 minute, a large amount of precipitate was observed, resulting in a thick opaque solution. Additional acetonitrile (8 mL) was added for easier stirring, and the mixture was allowed to stir at ambient conditions for 3 days. Solids were collected by vacuum filtration, air dried under reduced pressure approximately 8 minutes, and analyzed. This procedure reproducibly gave cocrystal 1 from smaller-scale experiments, as well.

Rifaximin:Piperazine Cocrystal 2

A portion of the Rifaximin:piperazine cocrystal 1 was transferred to a 1-dram vial, which was uncapped and placed inside a 20-mL vial containing acetonitrile (2 mL). The 20-mL vial was capped and left at ambient conditions for vapor stress. After 7 days, a portion of the solids was removed and quickly analyzed by XRPD, resulting in cocrystal 2. This procedure reproducibly gave cocrystal 2, presumably after longer periods of stressing, as well. It is to be noted, though, that cocrystal 2 was found to quickly convert to cocrystal 1 or material similar to cocrystal 1 upon exposure to ambient conditions.

Example 3

Form θ Preparation and Characterization

Form θ was generated from drying Form ζ under nitrogen for approximately ten minutes, Table 23. The nitrogen flow rate was sufficient to "tumble" the solids in the container. The XRPD pattern is presented in FIG. 67 and was of sufficient quality to be indexed, see Table 23.

TABLE 23

Generation Attempts of Selected Rifaximin Forms for Drying and Stability Evaluation

| Method | Observations | Results |
|---|---|---|
| crystallization from MeOH | dark red, blades (acicular like), birefringent | θ + ζ disordered |
| sub sample of 3985-42-01 dried under nitrogen | orange opaque fines, no birefringence | ζ + θ |
| nitrogen dried, flow rate kept solids suspended in vial | orange red opaque fines, no birefringence | θ θ + ι |

Figure 60:
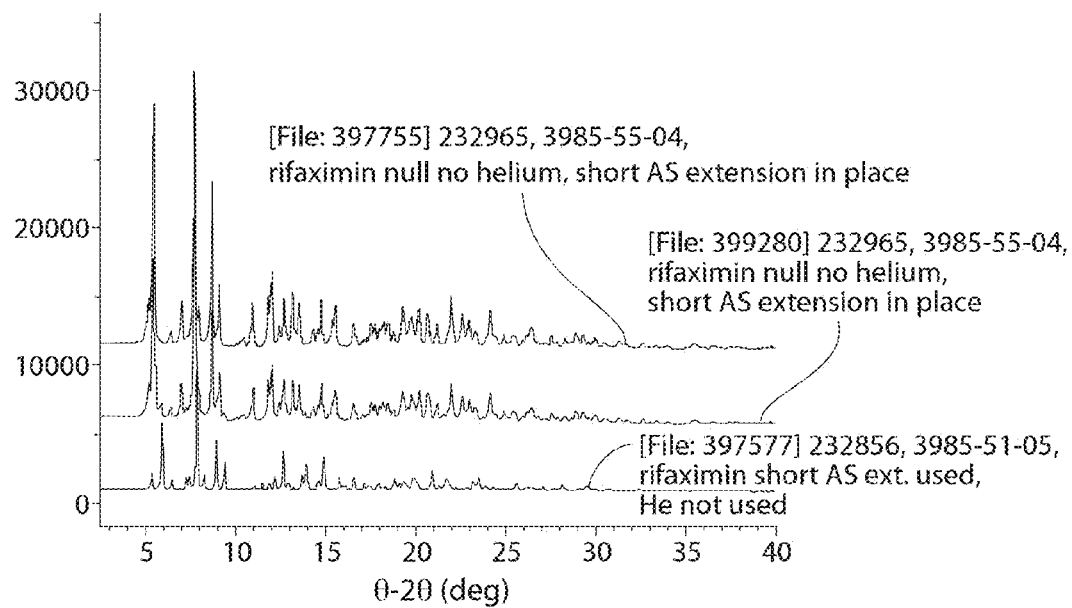
FIG. 60 are exemplary XRPD patterns showing conversion of Form θ. From top to bottom: Form θ, Form θ+ι, Form ι.

Form θ drying and physical stability evaluation was not formally included in the protocol. Based on limited analysis, some insight into the stability is observed. The initial sample was generated from nitrogen drying of Form ζ. The initial XRPD pattern was acquired utilizing parameters not consistent with the other data acquisition. The analyst reanalyzed the sample within hours and conversion to Form ι is observed, FIG. 60.

Indexing and structure refinement are computational studies which are not performed under cGMP guidelines. The XRPD pattern of Rifaximin Form θ was indexed using proprietary SSCI software. The indexed solution was verified and illustrated using CheckCell version Nov. 1, 2004.

The indexed XRPD pattern of Rifaximin Form θ is illustrated in FIG. 61. Agreement between the allowed peak positions, marked with the bars in FIG. 61, and the observed peaks indicates a consistent unit cell determination. Successful indexing of the pattern indicates that the sample is composed primarily of a single crystalline phase. Space groups consistent with the assigned extinction symbol, unit cell parameters, and derived quantities are tabulated in FIG. 61. To confirm the tentative indexing solution, the molecular packing motifs within the crystallographic unit cells must be determined. No attempts at molecular packing were performed.

Figure 62:
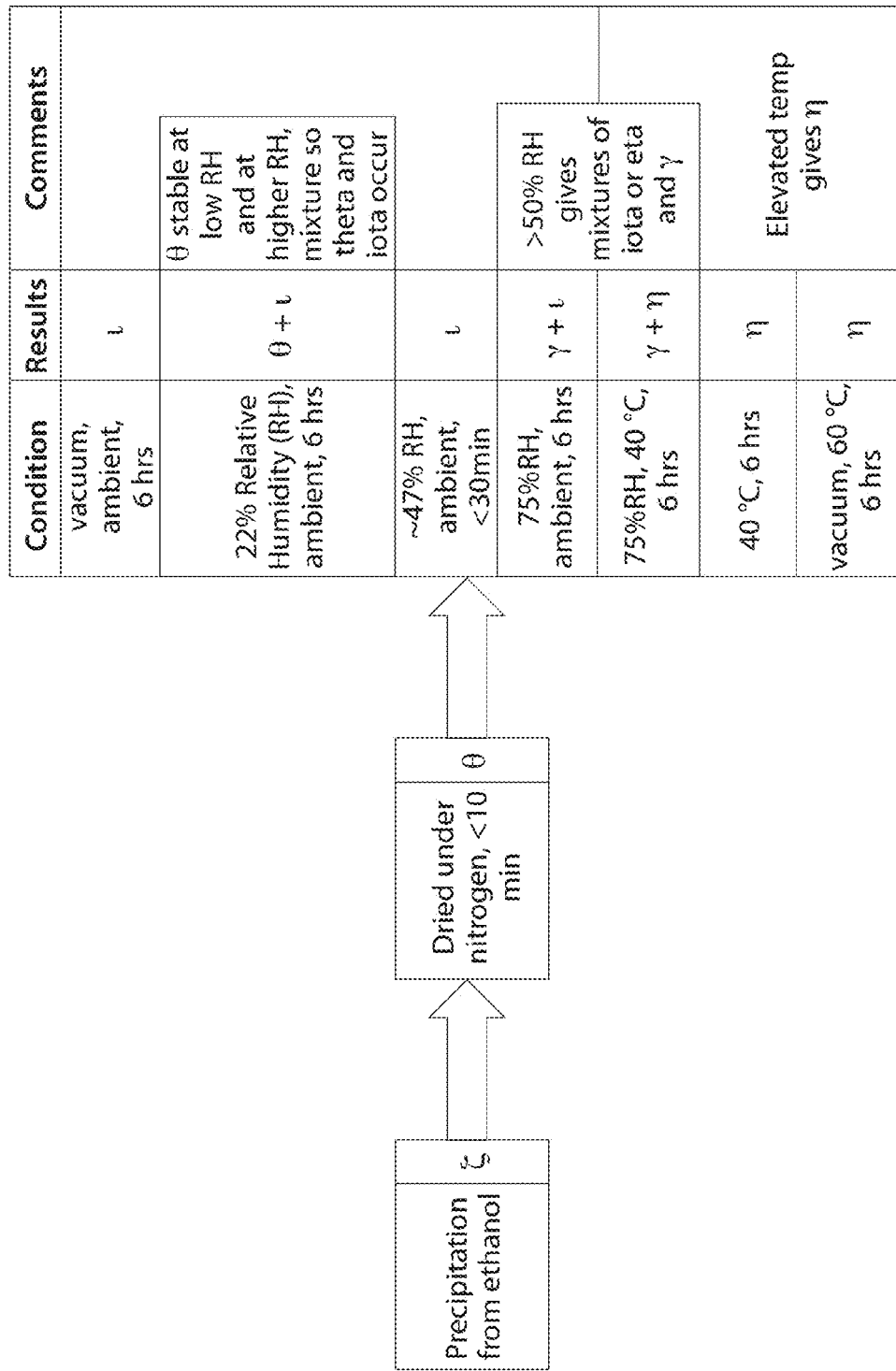
FIG. 62 shows a process flow diagram for theta, eta and iota.

FIG. 62 shows a process flow diagram for the production of Form Eta and Form Iota as well as mixtures of other forms with Eta and Iota. In one aspect, a method for making rifaximin Form eta, comprises precipitating rifaximin from ethanol; drying the precipitated rifaximin under nitrogen; maintaining the precipitated rifaximin at an elevated temperature for 30 minutes or longer. In certain embodiments, the maintaining is at about 40° C. for about 2 hours or longer. In other embodiments, the maintaining is under vacuum at about 60° C. for 2 hours or longer. In other embodiments, the drying is for about 10 minutes or less.

A method for making rifaximin Form iota, comprises precipitating rifaximin from ethanol; drying the precipitated rifaximin under nitrogen; and maintaining the rifaximin at ambient temperature. In certain embodiments, the maintaining further comprises the rifaximin under vacuum for 6 or more hours. In certain embodiments, the maintaining further comprises the rifaximin at between about 22% and 50% humidity. In other embodiments, the drying is for about 10 minutes or less.

A method for making rifaximin Form iota and Form theta mixtures, comprises precipitating rifaximin from ethanol; drying the precipitated rifaximin under nitrogen; and maintaining the rifaximin at from between about 10% RH to about 46% relative humidity (RH) at ambient temperatures from at least one hour to about 6 hours or longer. In other embodiments, the drying is for about 10 minutes or less.

Figure 63:
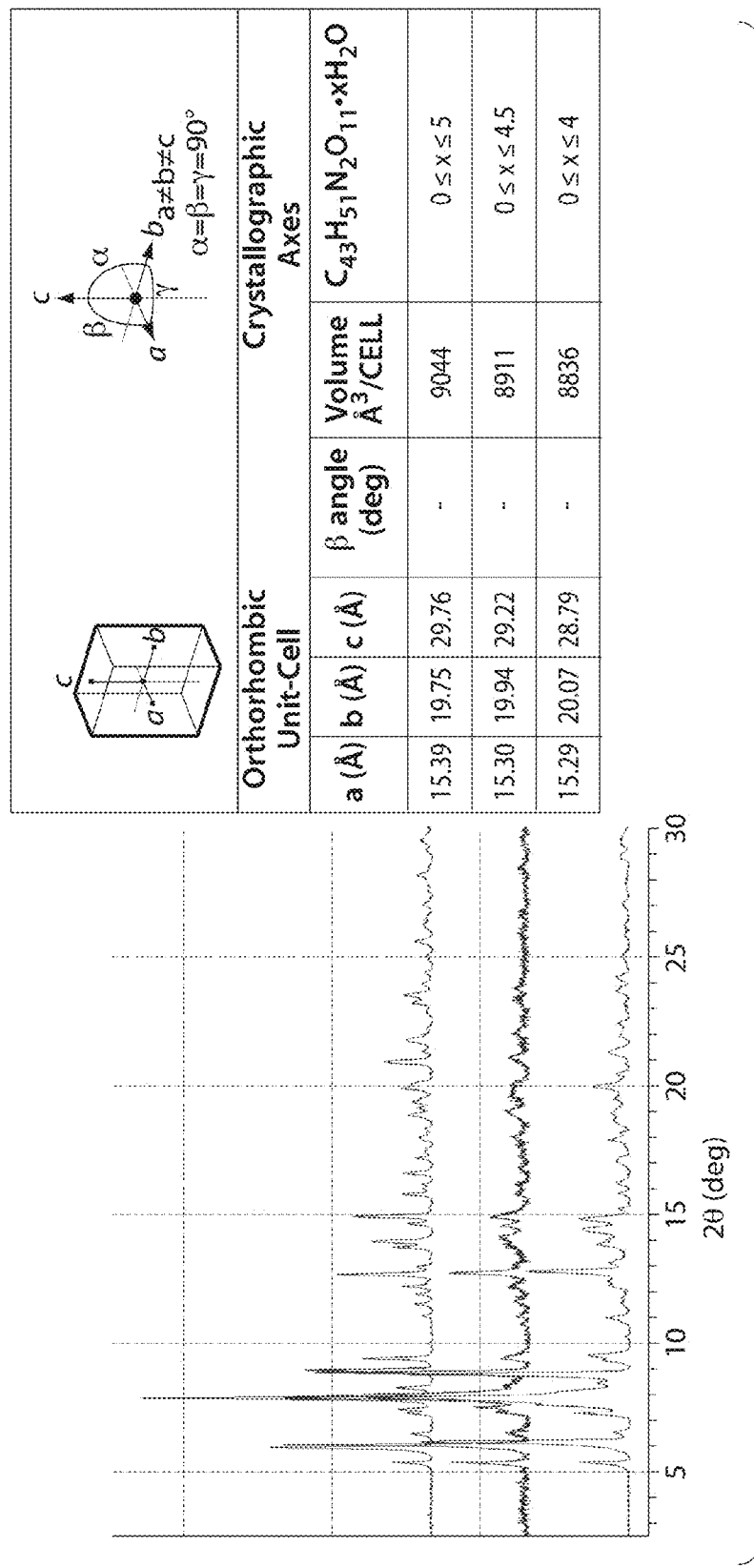
FIG. 63 shows Iota unit cell analysis and XRPD patterns of Iota.
Figure 64:
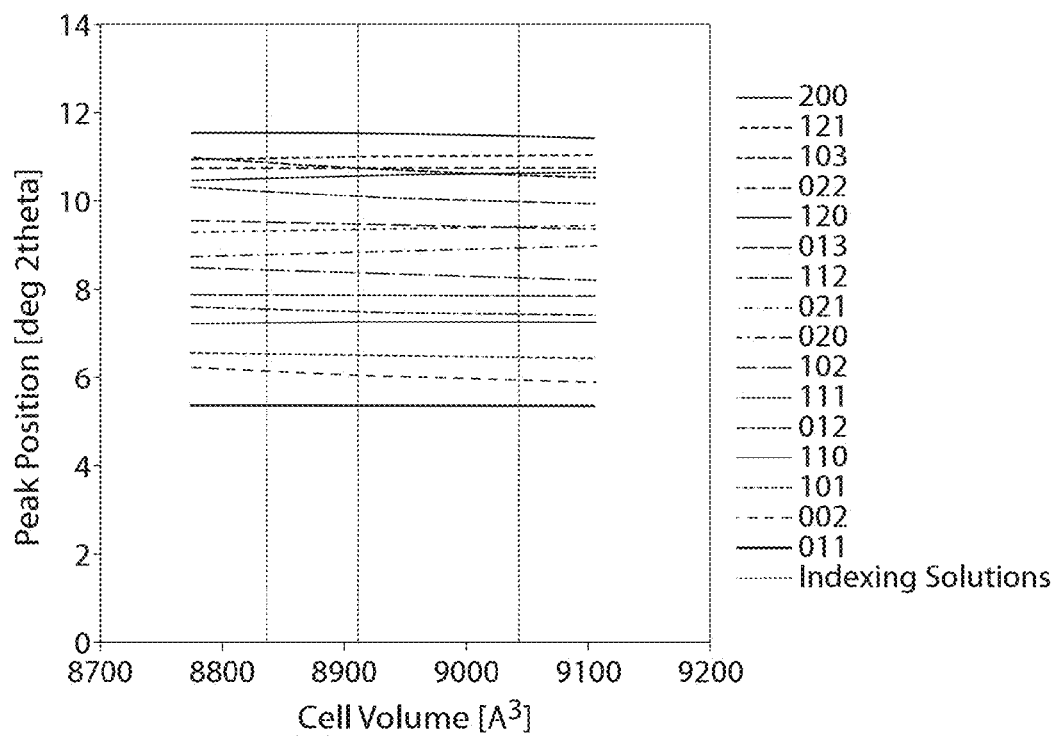
FIG. 64 shows Iota indexing.

FIG. 63 shows an exemplary XRPD of Form Iota and Form Iota unit cell measurements. In one aspect, provided herein is a rifaximin Form Iota having substantially similar measurements to those shown for Form Iota in FIG. 63. FIG. 64 shows Iota indexing in graphical format, wherein peak positions are plotted against cell volume. Indexing is described in more detail infra.

Figure 65:
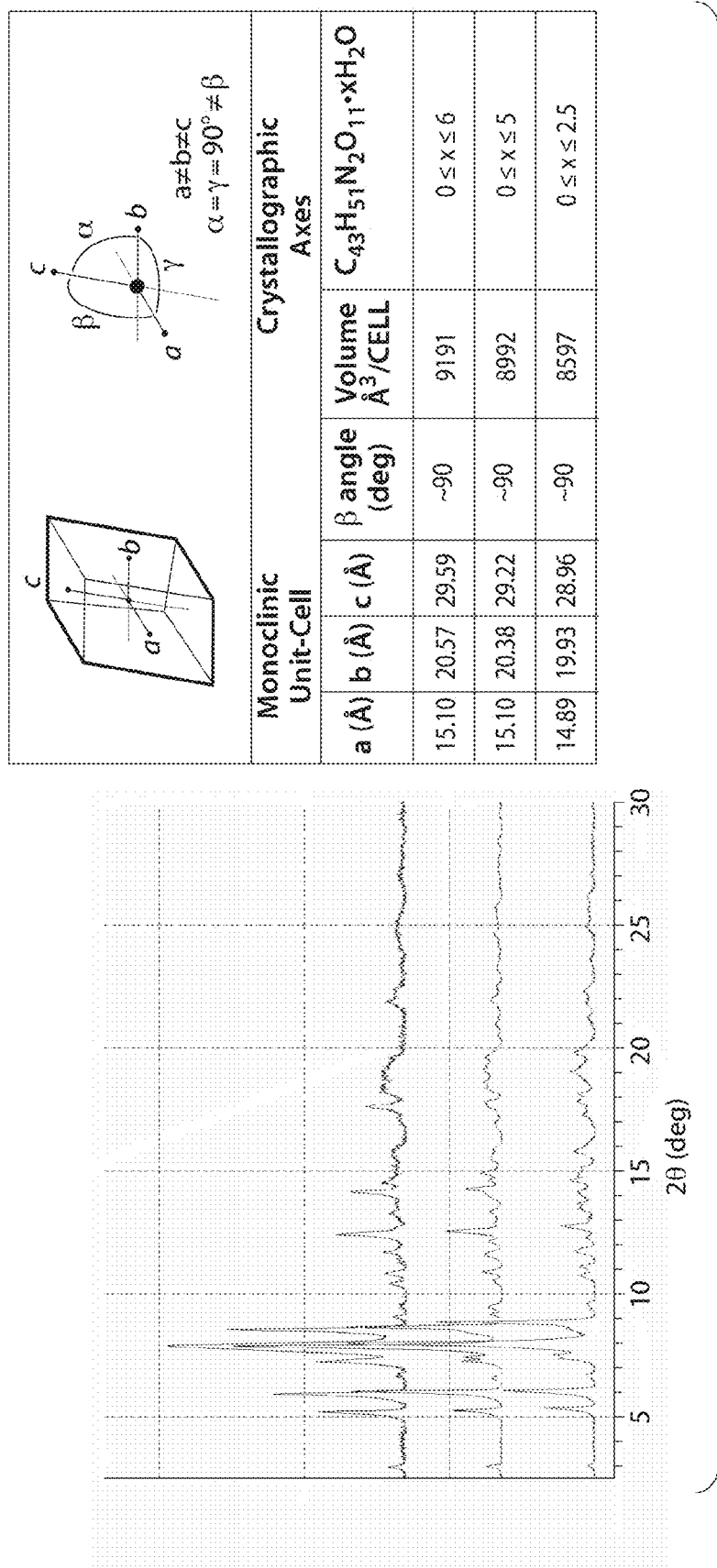
FIG. 65 shows Eta unit cell analysis and XRPD patterns of Eta.
Figure 66:
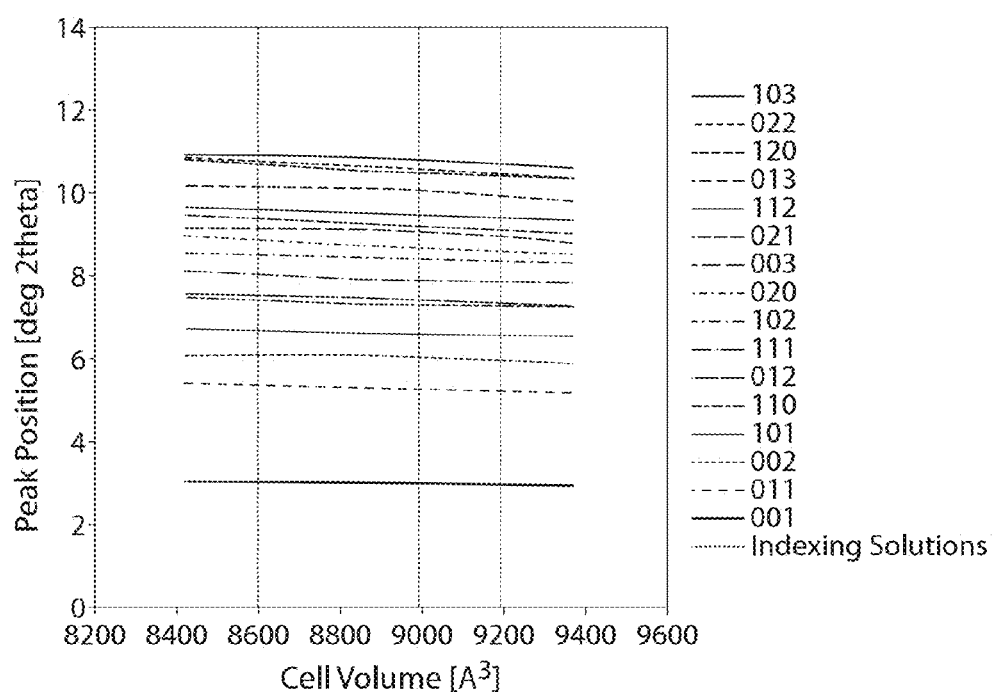
FIG. 66 shows Eta indexing.

FIG. 65 shows an exemplary XRPD of Form Eta and Form Eta unit cell measurements. In one aspect, provided herein is a rifaximin Form Eta having substantially similar measurements to those shown for Form Eta in FIG. 65. FIG. 66 shows Eta indexing in graphical format, wherein peak positions are plotted against cell volume. Indexing is described in more detail infra.

Example 4

Form θ

Preparation

Large Scale Experiment

In one example, Form θ was obtained by drying Form ζ under vacuum at ambient temperature for approximately 6 hours. Form θ may be an ethanolate based on 1H-NMR results. One sample contains two moles of ethanol per mole of rifaximin by 1H-NMR, but the volume estimated from the tentative XRPD indexing solution indicates the unit cell is able to accommodate up to 4 moles of ethanol per mole of rifaximin. XRPD patterns of Form θ were indexed successfully. Successful indexing of the powder diffraction pattern exhibited by this form provides support that Form θ is a single crystalline phase.

Rifaximin Form θ was obtained at large scale by vacuum drying of Form ζ. In this Example, 58.96 g of rifaximin was added to 300 mL of ethanol with stirring at ambient condition. The rifaximin almost completely dissolved initially and yielded a very dark red solution. With continuous stirring, the solution became lighter in color and turbidity increased until an orange/red paste was formed. At that point, the another 100 mL of ethanol was added. The total volume of ethanol was 400 mL. The slurry sample was then vacuum filtered through a filter paper under nitrogen environment (21% RH, 22° C.) and a red-orange paste was obtained. Once filtrate stopped dripping from the end of funnel, the filter cake was broken loose on the filter paper with a spatula while vacuum and nitrogen still remained on. The total drying time of the sample on filter paper was approximately 30 minutes.

The resulting solid was identified as Form ζ by XRPD. This solid sample was later dried under vacuum for approximately 6 hours at ambient temperature. The post XRPD pattern confirms that the solid converted to Form θ after vacuum drying.

Small Scale Experiment

In this Example, 1 mL ethanol was added to 251.5 mg rifaximin. When sonicated, the rifaximin almost all dissolved initially. But red/orange precipitate was formed upon further sonication. Another 1 mL ethanol was added (total ethanol=2 mL) and sonicated. A thick paste was obtained. The solid was isolated by filtering through a filter paper and rinsed with 2 mL of ethanol. The material was subsequently transferred into a 20 ml vial sealed with filter paper and tumbled within the vial under a high velocity stream of nitrogen for approximately 10 minutes. Free-flowing, orange/red opaque fines were observed under microscope and identified as Form θ by XRPD analysis.

Characterization

Figure 67:
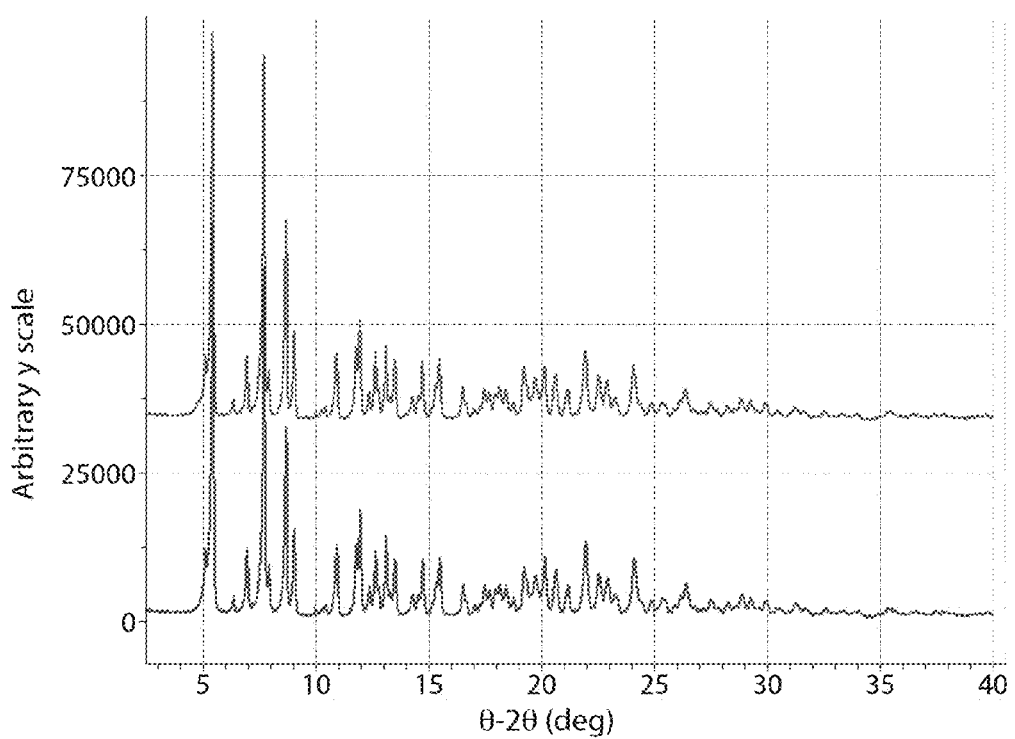
FIG. 67 shows XRPD patterns of rifaximin Form θ. From top to bottom: as prepared Form θ; Form θ after 8 days of ambient storage.

The XRPD patterns of Form θ from the large-scale experiment are shown in FIG. 67. The sample was re-analyzed by XRPD after 8 days of ambient storage and remained Form θ.

Figure 68:
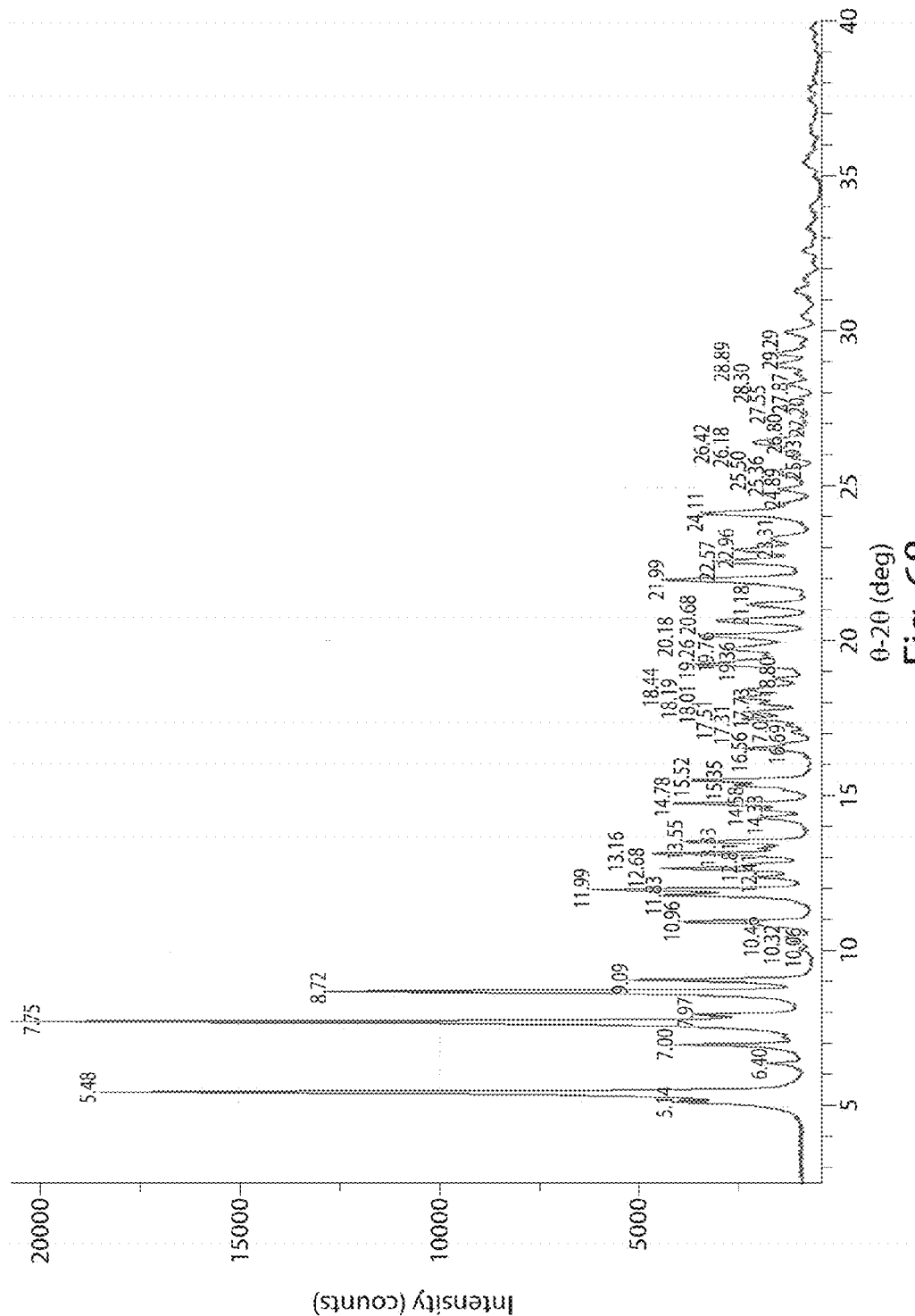
FIG. 68 is a list of observed peaks for rifaximin Form θ. Note that the peak labels in this image are meant as a visual aid. Consult Table 24 for accurate 2θ positions.

A list of peak positions for one XRPD pattern of rifaximin Form θ obtained from the small scale experiment described above) is presented in FIG. 68. Observed and prominent peak lists are included in Table 24 and Table 25, while representative and characteristic peak lists are not included.

TABLE 24

Observed Peaks for Rifaximin Form θ

| °2θ | d space (Å) | Intensity (%) |
|---|---|---|
| 5.14 ± 0.10 | 17.186 ± 0.341 | 20 |
| 5.48 ± 0.10 | 16.138 ± 0.300 | 89 |
| 6.40 ± 0.10 | 13.821 ± 0.219 | 9 |
| 7.00 ± 0.10 | 12.634 ± 0.183 | 20 |
| 7.75 ± 0.10 | 11.409 ± 0.149 | 100 |
| 7.97 ± 0.10 | 11.099 ± 0.141 | 18 |
| 8.72 ± 0.10 | 10.143 ± 0.117 | 62 |
| 9.09 ± 0.10 | 9.733 ± 0.108 | 25 |
| 10.06 ± 0.10 | 8.797 ± 0.088 | 5 |
| 10.32 ± 0.10 | 8.570 ± 0.084 | 6 |
| 10.46 ± 0.10 | 8.461 ± 0.081 | 6 |
| 10.96 ± 0.10 | 8.075 ± 0.074 | 19 |
| 11.83 ± 0.10 | 7.483 ± 0.064 | 21 |
| 11.99 ± 0.10 | 7.379 ± 0.062 | 30 |
| 12.41 ± 0.10 | 7.132 ± 0.058 | 10 |
| 12.68 ± 0.10 | 6.982 ± 0.055 | 21 |
| 12.81 ± 0.10 | 6.909 ± 0.054 | 11 |
| 13.16 ± 0.10 | 6.726 ± 0.051 | 22 |
| 13.33 ± 0.10 | 6.642 ± 0.050 | 10 |
| 13.55 ± 0.10 | 6.536 ± 0.048 | 19 |
| 14.33 ± 0.10 | 6.180 ± 0.043 | 10 |
| 14.58 ± 0.10 | 6.074 ± 0.042 | 9 |
| 14.78 ± 0.10 | 5.992 ± 0.041 | 20 |
| 15.35 ± 0.10 | 5.772 ± 0.038 | 12 |
| 15.52 ± 0.10 | 5.710 ± 0.037 | 18 |
| 16.56 ± 0.10 | 5.355 ± 0.032 | 12 |
| 16.69 ± 0.10 | 5.312 ± 0.032 | 7 |
| 17.07 ± 0.10 | 5.193 ± 0.030 | 6 |
| 17.31 ± 0.10 | 5.124 ± 0.030 | 6 |
| 17.51 ± 0.10 | 5.065 ± 0.029 | 12 |
| 17.73 ± 0.10 | 5.004 ± 0.028 | 11 |
| 18.01 ± 0.10 | 4.926 ± 0.027 | 9 |
| 18.19 ± 0.10 | 4.876 ± 0.027 | 12 |
| 18.44 ± 0.10 | 4.810 ± 0.026 | 12 |
| 18.80 ± 0.10 | 4.721 ± 0.025 | 8 |
| 19.26 ± 0.10 | 4.608 ± 0.024 | 17 |
| 19.36 ± 0.10 | 4.584 ± 0.024 | 13 |
| 19.76 ± 0.10 | 4.492 ± 0.023 | 14 |
| 20.18 ± 0.10 | 4.400 ± 0.022 | 17 |
| 20.68 ± 0.10 | 4.294 ± 0.021 | 15 |
| 21.18 ± 0.10 | 4.194 ± 0.020 | 11 |
| 21.99 ± 0.10 | 4.043 ± 0.018 | 21 |
| 22.57 ± 0.10 | 3.939 ± 0.017 | 15 |
| 22.96 ± 0.10 | 3.874 ± 0.017 | 13 |
| 23.31 ± 0.10 | 3.817 ± 0.016 | 8 |
| 24.11 ± 0.10 | 3.691 ± 0.015 | 16 |
| 24.89 ± 0.10 | 3.577 ± 0.014 | 7 |
| 25.36 ± 0.10 | 3.512 ± 0.014 | 7 |
| 25.50 ± 0.10 | 3.494 ± 0.014 | 7 |
| 25.93 ± 0.10 | 3.436 ± 0.013 | 5 |
| 26.18 ± 0.10 | 3.404 ± 0.013 | 8 |
| 26.42 ± 0.10 | 3.374 ± 0.013 | 10 |
| 26.80 ± 0.10 | 3.327 ± 0.012 | 5 |
| 27.20 ± 0.10 | 3.278 ± 0.012 | 5 |
| 27.55 ± 0.10 | 3.238 ± 0.012 | 7 |
| 27.87 ± 0.10 | 3.201 ± 0.011 | 5 |
| 28.30 ± 0.10 | 3.153 ± 0.011 | 6 |
| 28.89 ± 0.10 | 3.091 ± 0.011 | 8 |
| 29.29 ± 0.10 | 3.049 ± 0.010 | 7 |

TABLE 25

Prominent Peaks for Rifaximin Form θ

| °2θ | d space (Å) | Intensity (%) |
|---|---|---|
| 5.48 ± 0.10 | 16.138 ± 0.300 | 89 |
| 7.00 ± 0.10 | 12.634 ± 0.183 | 20 |
| 7.75 ± 0.10 | 11.409 ± 0.149 | 100 |
| 8.72 ± 0.10 | 10.143 ± 0.117 | 62 |
| 9.09 ± 0.10 | 9.733 ± 0.108 | 25 |
| 10.96 ± 0.10 | 8.075 ± 0.074 | 19 |

An indexing solution from the XRPD pattern was also obtained. Indexing is the process of determining the size and shape of the unit cell given the peak positions in a diffraction pattern. The term gets its name from the assignment of Miller index labels to individual peaks.

Figure 69:
FIG. 69 is an indexing solution for Rifaximin Form θ. The bars indicate allowed reflections based on the unit cell dimensions and the assigned space group (P2$_1$2$_1$2$_1$, #19).

The XRPD pattern of rifaximin Form θ was indexed using proprietary SSCI software and is illustrated in FIG. 69. The indexed solution was verified and illustrated using CheckCell version Nov. 1, 2004.

Agreement between the allowed peak positions, marked with the bars in FIG. 67, and the observed peaks indicates a consistent unit cell determination. Successful indexing of the pattern indicates that the sample is composed primarily of a single crystalline phase. Space groups consistent with the assigned extinction symbol, unit cell parameters, and derived quantities are tabulated in Table 26.

TABLE 26

Indexing Solution and Derived Quantities

| Form/Pattern | Rifaximin Form θ |
|---|---|
| Family and Space Group | Orthorhombic P2$_1$2$_1$2$_1$ (#19) |
| Z'/Z | 2/8 |
| a (Å) | 15.274 |
| b (Å) | 20.277 |
| c (Å) | 32.231 |
| α (deg) | 90 |
| β (deg) | 90 |
| γ (deg) | 90 |
| Volume (Å$^3$/cell) | 9982.3 |
| V/Z (Å$^3$/asym. unit) | 1247.8 |
| Assumed Composition$^a$ | C$_{43}$H$_{51}$N$_3$O$_{11}$•xC$_2$H$_6$O 0 ≤ x ≤ 4 |
| Density (g/cm$^3$)$^a$ | 1.05 ≤ y ≤ 1.29 |
| Weight Fraction Solvent (%)$^a$ | 0 ≤ z ≤ 19.0 |

Assuming two independent rifaximin molecules in the asymmetric unit, there is sufficient volume remaining for up to four molecules of ethanol per molecule of rifaximin. Density and solvent values calculated in Table 26 are listed with a range of zero to four molecules of ethanol per molecule of rifaximin. 1H-NMR result indicated that the Form θ sample analyzed contained approximately 2 moles of ethanol per mole of rifaximin (Table 27).

TABLE 27

Characterizations of Rifaximin Form θ

| Analytical Technique | Results |
|---|---|
| XRPD | θ |
| | θ (after 8 days of ambient storage) |
| DSC | Endo: 63, 106, and 220° C. |
| TGA | 10.9% wt loss up to 120° C. |
| Karl-Fischer | 0.27% of water by weight |

TABLE 27-continued

Characterizations of Rifaximin Form θ

| Analytical Technique | Results |
|---|---|
| $^1$H-NMR | Chemical structure intact, 2 moles of ethanol per mole of rifaximin |
| Solid-state $^{13}$C NMR | Spectrum acquired |
| ATR-IR | Spectrum acquired |
| Raman | Spectrum acquired |
| Moisture Balance | −7.314% wt change upon equilibration at 5% RH 5.733% wt gain from 5%-95% RH 5.826% wt lost from 95%-5% RH |
| Post-MB XRPD | ι |

Figure 70A:
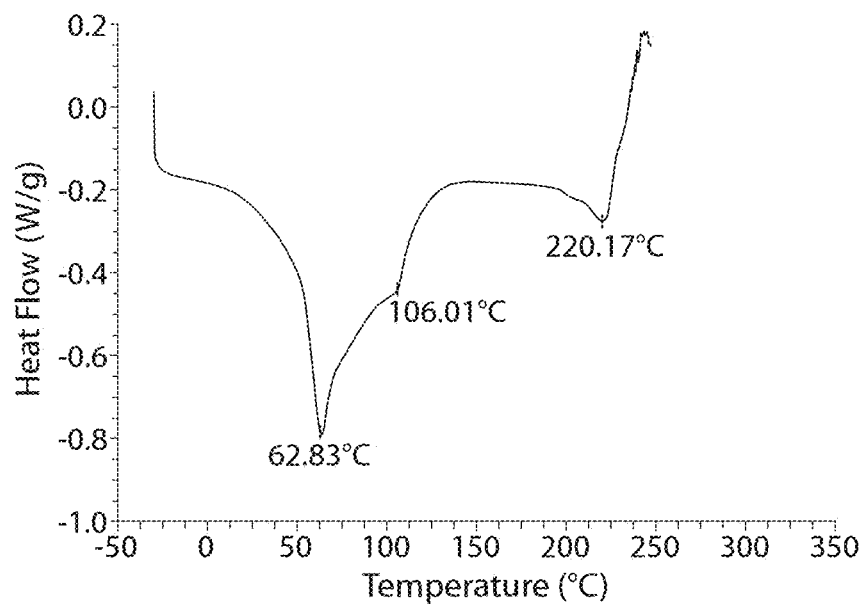
FIGS. 70 A and B are exemplary DSC and TGA thermograms of rifaximin Form θ, respectively.
Figure 70B:
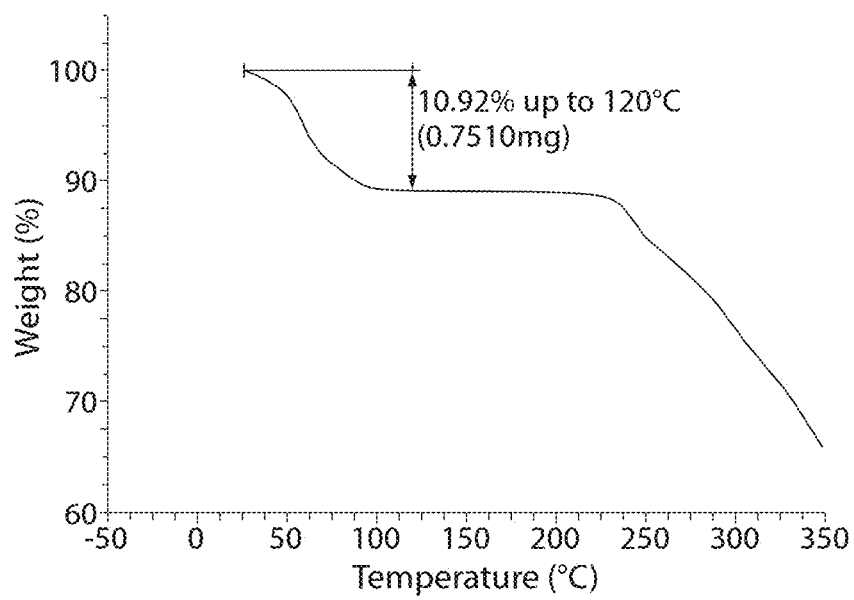
Figure 71:
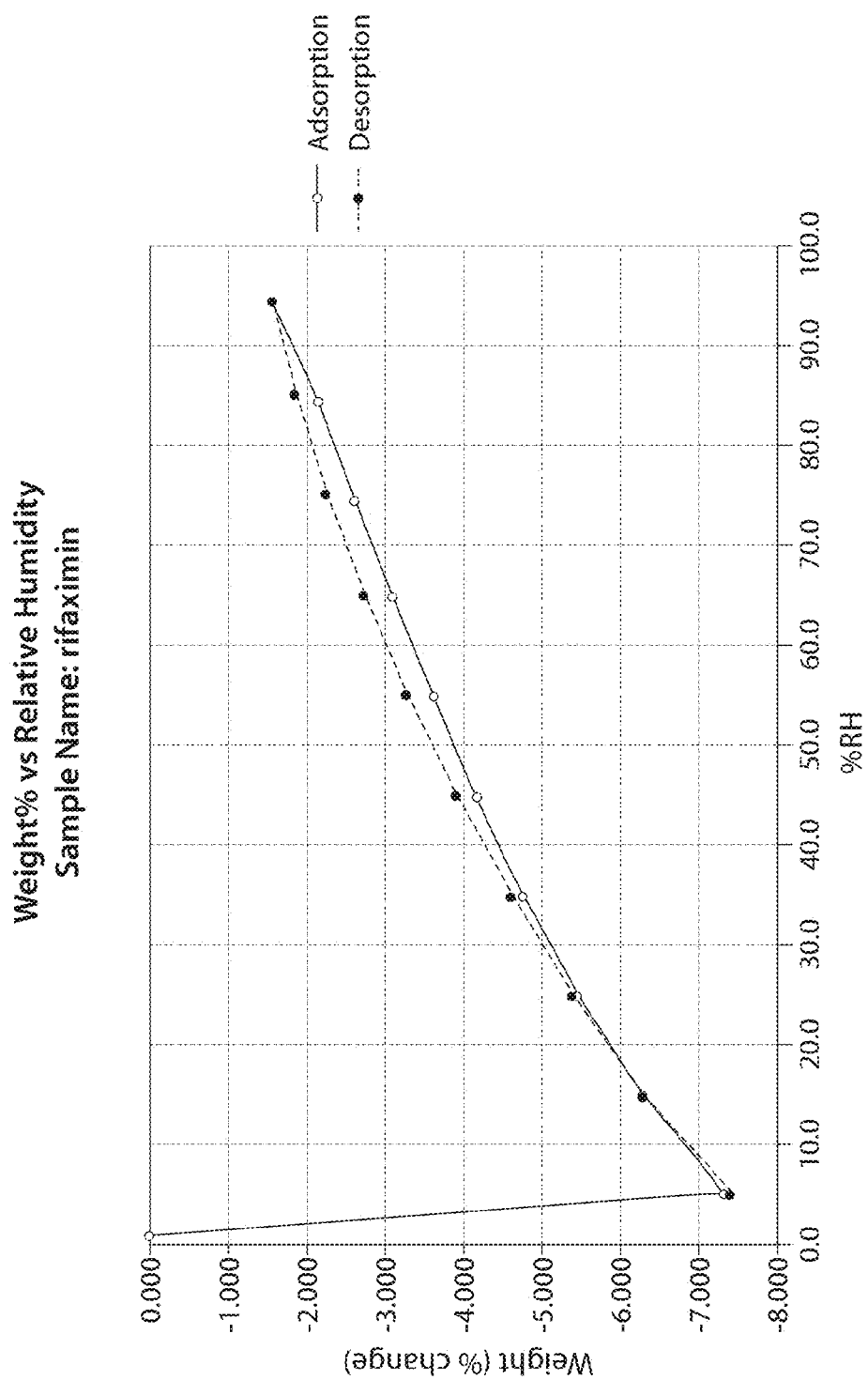
FIG. 71 is an exemplary moisture sorption of rifaximin Form θ.
Figure 72:
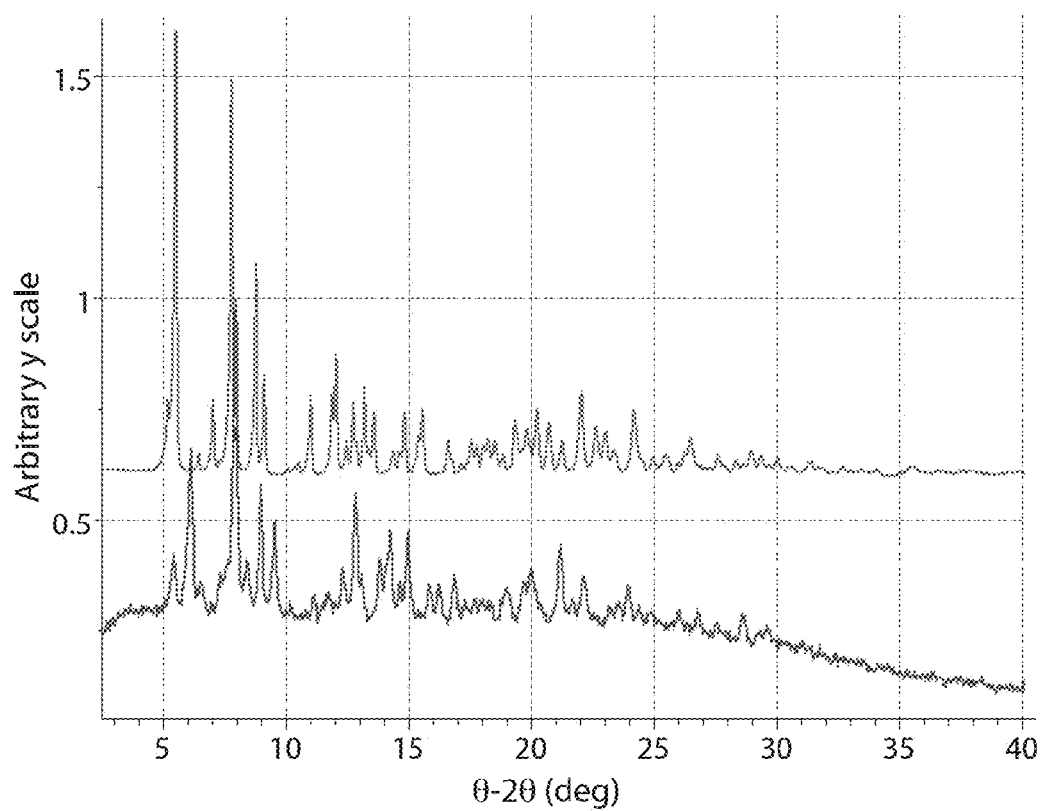
FIG. 72 is an exemplary post-moisture sorption XRPD of rifaximin Form θ. From top to bottom: before moisture sorption (Form θ); after moisture sorption (Form ι).

Additional characterization data for rifaximin Form θ are presented in FIG. 70 through FIG. 72, and are summarized in Table 27.

Moisture sorption data for rifaximin Form θ are shown in FIG. 71. An initial weight loss of 7.3% was observed upon equilibration at 5% RH. The material exhibited a 5.7% weight gain from 5 to 95% RH and a 5.8% weight loss from 95 to 5% RH. The overall weight loss is approximately 7.4%. The XRPD pattern of the specimen post-moisture sorption (FIG. 72) has been assigned as Form ι.

Example 5

Particle Sizes

Rifaximin Forms have different particle sizes. Below is a Table listing particle sizes for each of the kappa and eta Forms of rifaximin.

TABLE 28

Particle size distributions for Rifaximin forms

| Form | d10 (μm)$^a$ | d50 (μm)$^b$ | d90 (μm)$^c$ |
|---|---|---|---|
| As received | 0.399 | 8.629 | 33.891 |
| κ | 15.551 | 90.684 | 225.815 |
| η | 3.857 | 79.844 | 290.353 |

$^a$10% of the total volume of particles being less than the indicated particle size in μm.
$^b$50% of the total volume of particles being less than the indicated particle size in μm.
$^c$90% of the total volume of particles being less than the indicated particle size in μm.

Example 6

Experimental Methods

Compression

A weighed amount of a given Rifaximin:piperazine cocrystal was transferred to a Woods die and compressed using a Carver press at given parameters. The resulting pellet was broken apart and analyzed.

Computational Methods

Indexing of Rifaximin:Piperazine Cocrystal 1

The XRPD pattern of the Rifaximin:piperazine cocrystal 1 was indexed using X'Pert High Score Plus (X'Pert High Score Plus 2.2a (2.2.1).)

The indexed solution was verified and illustrated using CheckCell version Nov. 1, 2004 (CheckCell Nov. 1, 2004; found on the world wide web at www.ccp14.ac.uk/tutorial/lmgp)

Indexing of Rifaximin:Piperazine Cocrystal 2

The XRPD pattern of Rifaximin:piperazine cocrystal 2 (ACN solvate) was indexed using proprietary SSCI software.

The indexed solution was verified and illustrated using CheckCell version Nov. 1, 2004.

Peak Picking of IR and Raman Spectra

Peak picking was performed using Omnic version 7.2. Infrared and Raman spectra are presented for each of the starting materials and cocrystals with all Observed Peaks labeled. Observed Peaks include all IR and Raman peaks for a given form, with the exclusion of very weak intensity peaks and broad peaks with poorly defined maxima.

Characteristic Peaks are a subset of Observed Peaks and are used to differentiate one crystalline form from another crystalline form. Characteristic peaks are determined by evaluating which observed peaks, if any, are present in one crystalline form of a compound against all other known crystalline forms of that compound to within ±4 cm-1. Not all crystalline polymorphs of a compound necessarily have at least one characteristic peak. Characteristic Peaks are identified for the Rifaximin:piperazine cocrystal 2.

Peak position variabilities are given to within ±2 cm-1, based on the observed sharpness of the peaks picked and acquisition of data using a 2 cm-1 data point spacing (4 cm-1 resolution). Third party measurements on independently prepared samples on different instruments may lead to variability which is greater than ±2 cm-1.

X-Ray Powder Diffraction Peak Identification Process

The peak picking data presented in this report contain x-ray diffraction patterns with labeled peaks and with peak lists. Under most circumstances, peaks within the range of up to about 30° 2θ were selected. Although peaks are labeled on diffraction patterns and listed in tables, for technical reasons, different rounding algorithms were used to round each peak to the nearest 0.1° or 0.01° 2θ, depending upon the instrument used to collect the data and/or the inherent peak resolution. The location of the peaks along the x-axis (° 2θ) in both the figures and the lists were automatically determined using proprietary software (PatternMatch™ 3.0.1) and rounded to one or two significant figures after the decimal point based upon the above criteria. Peak position variabilities are given to within ±0.1° 2θ based upon recommendations outlined in the USP discussion of variability in x-ray powder diffraction (United States Pharmacopeia, USP 32, NF 27, Vol. 1, pg. 392, 2009). Third party measurements on independently prepared samples on different instruments may lead to variability which is greater than ±0.1° 2θ. For d-space listings, the wavelength used to calculate d-spacings was 1.541874 Å, a weighted average of the Cu—Kα1 and Cu—Kα2 wavelengths (Phys. Rev. A56(6) 4554-4568 (1997). Variability associated with d-spacing estimates was calculated from the USP recommendation, at each d-spacing, and provided in the respective data tables.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks". In general, the more data collected to determine Representative Peaks, the more confident one can be of the classification of those peaks.

"Characteristic peaks", to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.1° 2θ. Not all crystalline polymorphs of a compound necessarily have at least one characteristic peak.

Instrumental Techniques

Differential Scanning calorimetry (DSC)

DSC was performed using a TA Instruments 2920 or Q2000 differential scanning calorimeter. Temperature calibration was performed using NIST traceable indium metal. The sample was placed into an aluminum DSC pan, covered with a lid, and the weight was accurately recorded. A weighed aluminum pan configured as the sample pan was placed on the reference side of the cell. The data acquisition parameters and pan configuration for each thermogram are displayed in the image in the Data section of this report. The method code on the thermogram is an abbreviation for the start and end temperature as well as the heating rate; e.g., 25-250-10 means "from 25° C. to 250° C., at 10° C./min". The following table summarizes the abbreviations used in each image for pan configurations:

| Abbreviation (in comments) | Meaning |
|---|---|
| LP | Lid perforated with a laser pinhole |
| HS | Lid hermetically sealed |
| HSLP | Lid hermetically sealed and perforated with a laser pinhole |
| C | Lid crimped |
| NC | Lid not crimped |

Dynamic Vapor Sorption (DVS)

Automated dynamic vapor sorption (DVS) data were collected on a VTI SGA-100 Vapor Sorption Analyzer. NaCl and PVP were used as calibration standards. Samples were not dried prior to analysis. Sorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours.

Infrared Spectroscopy (IR)

IR spectra were acquired on Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. Wavelength verification was performed using NIST SRM 1921b (polystyrene). An attenuated total reflectance (ATR) accessory (Thunderdome™, Thermo Spectra-Tech), with a germanium (Ge) crystal was used for data acquisition. Each spectrum represents 256 co-added scans collected at a spectral resolution of 4 cm-1 A background data set was acquired with a clean Ge crystal. A Log 1/R (R=reflectance) spectrum was obtained by taking a ratio of these two data sets against each other.

Optical Microscopy

Samples were observed under a Wolfe optical microscope with crossed polarizers at either 2× or 4× objectives or under a stereomicroscope with a first order red compensator with crossed polarizers at 0.8× to 10× objectives.

Proton NMR Spectroscopy/Solution 1D $^1$H NMR Spectroscopy

The solution NMR spectra were acquired with a Varian UNITYINOVA-400 spectrometer. The samples were prepared by dissolving approximately 5 to 10 mg of sample in DMSO-d$_6$ or CDCl$_3$ containing TMS. The data acquisition parameters are displayed in the first plot of the spectrum in the Data section of this report.

Solution 1D $^1$H NMR Spectroscopy (SDS, Inc.)

Two solution $^1$H NMR spectra were acquired by Spectral Data Services of Champaign, Ill. at 25° C. with a Varian UNITYINOVA-400 spectrometer at a $^1$H Larmor frequency of 399.798 MHz. The samples were dissolved in DMSO-d$_6$ or CDCl$_3$, respectively. The spectra were acquired with a 1H pulse width of 6.0 μs, a 5 second delay between scans, a spectral width of 7000 Hz with 35K data points, and 40 co-added scans. The free induction decay (FID) was processed with 64K points and an exponential line broadening factor of 0.2 Hz to improve the signal-to-noise ratio. The residual peak from incompletely deuterated DMSO is at approximately 2.50 ppm; incompletely deuterated chloroform appears as a singlet at 7.26 ppm. The relatively broad peak at approximately 3.3 ppm is due to water (in the spectrum collected in DMSO only).

Raman Spectroscopy

Raman spectra were acquired on a FT-Raman module interfaced to a Magna-IR 860® Fourier transform infrared (FT-IR) spectrophotometer (Thermo Nicolet) equipped with an indium gallium arsenide (InGaAs) detector. Wavelength verification was performed using sulfur and cyclohexane. Each sample was prepared for analysis by placing the sample into a glass tube and positioning the tube in a gold-coated tube holder. Approximately 0.300 W of Nd:YVO4 laser power (1064 nm excitation wavelength) was used to irradiate the sample. Each spectrum represents 256 co-added scans collected at a spectral resolution of 4 cm$^{-1}$.

Solid-State NMR Spectroscopy (SSNMR)

The solid-state $^{13}$C cross polarization magic angle spinning (CP/MAS) NMR spectra were acquired at ambient temperature on a Varian UNITYINOVA-400 spectrometer (Larmor frequencies: $^{13}$C=100.542 MHz, $^1$H=399.789 MHz). The sample was packed into a 4 mm PENCIL type zirconia rotor and rotated at 12 kHz at the magic angle.

The first three data points of the FID were back predicted using the VNMR linear prediction algorithm to produce a flat baseline. The chemical shifts of the spectral peaks were externally referenced to the carbonyl carbon resonance of glycine at 176.5 ppm.

Thermogravimetry (TGA)

TGA analyses were performed using a TA Instruments 2950 or Q5000 IR thermogravimetric analyzer. Temperature calibration was performed using nickel and Alumel. Each sample was placed in an aluminum pan. The sample was hermetically sealed and the lid was pierced (for Q5000 only), then inserted into the TG furnace. The furnace was heated under nitrogen. The data acquisition parameters for each pattern are displayed in the image in the Data section of this report. The method code on the thermogram is an abbreviation for the start and end temperature as well as the heating rate; e.g., 25-350-10 means "from 25° C. to 350° C., at 10° C./min."

X-Ray Powder Diffraction (XRPD)

Inel XRG-3000 Diffractometer

XRPD patterns were collected with an Inel XRG-3000 diffractometer. An incident beam of Cu Kα radiation was produced using a fine-focus tube and a parabolically graded multilayer mirror. Prior to the analysis, a silicon standard (NIST SRM 640c) was analyzed to verify the Si 111 peak position. A specimen of the sample was packed into a thin-walled glass capillary, and a beam-stop was used to minimize the background from air. Diffraction patterns were collected in transmission geometry using Windif v. 6.6 software and a curved position-sensitive Equinox detector with a 2θ range of 120°. The data-acquisition parameters for each pattern are displayed above the image in the Data section of this report.

PANalytical EXPERT Pro MPD Diffractometer

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640c) was analyzed to verify the Si 111 peak position. A specimen of the sample was sandwiched between 3 μm-thick films and analyzed in transmission geometry. A beam-stop was used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data-acquisition parameters for each pattern are displayed above the image in the Data section of this report including the divergence slit (DS) before the mirror and the incident-beam antiscatter slit (SS).

Hot-Stage Microscopy

Hot stage microscopy was performed using a Linkam hot stage (FTIR 600) with a TMS93 controller mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20×0.4 N.A. long working distance objective with crossed polarizers and a first order red compensator. Images were captured using SPOT software (v. 4.5.9).

Karl-Fischer Titration

Coulometric Karl Fischer (KF) analysis for water determination was performed using a Mettler Toledo DL39 KF titrator. A blank titration was carried out prior to analysis. The sample was prepared under a dry nitrogen atmosphere, where approximately 1 gram of the sample were dissolved in approximately 1 mL dry Hydranal-Coulomat AD in a pre-dried vial. The entire solution was added to the KF coulometer through a septum and mixed for 10 seconds. The sample was then titrated by means of a generator electrode, which produces iodine by electrochemical oxidation: $2\ I^- \rightarrow I2+2e^-$. Two replicates were obtained to ensure reproducibility.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A rifaximin polymorph Form kappa, wherein the polymorph Form kappa exhibits an X-ray powder diffraction pattern having characteristic peaks expressed in degrees 2θ at
5.41-5.65, 6.45-6.67, 6.83-6.94, 7.03-7.06, and 7.52-7.56;
6.45-6.67, 6.83-6.94, 7.03-7.06, 7.68-7.78, and 18.46-18.61;

5.41-5.65, 6.45-6.67, 6.83-6.94, 7.03-7.06, 7.52-7.56, and 18.46-18.61; or 6.45-6.67, 6.45-6.67, 6.83-6.94, 7.03-7.06, 7.68-7.78, and 18.46-18.61.

2. The rifaximin polymorph Form kappa according to claim 1, containing less than 5% by weight total impurities.

3. The rifaximin polymorph Form kappa according to claim 1, wherein the compound is at least 50% pure, or at least 75% pure, or at least 80% pure, or at least 90% pure, or at least 95% pure, or at least 98% pure.

4. A pharmaceutical composition comprising the rifaximin polymorph Form kappa according to claim 1; and a pharmaceutically acceptable carrier.

5. The composition according to claim 4, wherein the rifaximin Form kappa is formulated as coated or uncoated tablets, hard or soft gelatin capsules, sugar-coated pills, lozenges, wafer sheets, pellets or powders in sealed packets.

6. A rifaximin:piperazine cocrystal 1, wherein the rifaximin:piperazine cocrystal 1 exhibits an X-ray powder diffraction pattern having characteristic peaks expressed in degrees 2θ at 6.58, 7.49, 18.15, and 20.21; or 5.74, 6.58, 7.49, 18.15, and 20.21.

7. The rifaximin:piperazine cocrystal 1 according to claim 6, containing less than 5% by weight total impurities.

8. The rifaximin:piperazine cocrystal 1 according to claim 6, wherein the compound is at least 50% pure, or at least 75% pure, or at least 80% pure, or at least 90% pure, or at least 95% pure, or at least 98% pure.

9. A pharmaceutical composition comprising the rifaximin:piperazine cocrystal 1 according to claim 6; and a pharmaceutically acceptable carrier.

10. The composition according to claim 9, wherein the rifaximin:piperazine cocrystal 1 is formulated as coated or uncoated tablets, hard or soft gelatin capsules, sugar-coated pills, lozenges, wafer sheets, pellets or powders in sealed packets.

11. A rifaximin:piperazine cocrystal 2, wherein the rifaximin:piperazine cocrystal 1 exhibits an X-ray powder diffraction pattern having characteristic peaks expressed in degrees 2θ at 5.58, 6.45, 7.19, and 7.29; or 5.58, 6.45, 7.19, 7.29, and 8.27.

12. The rifaximin:piperazine cocrystal 2 according to claim 11, containing less than 5% by weight total impurities.

13. The rifaximin:piperazine cocrystal 2 according to claim 11, wherein the compound is at least 50% pure, or at least 75% pure, or at least 80% pure, or at least 90% pure, or at least 95% pure, or at least 98% pure.

14. A pharmaceutical composition comprising the rifaximin:piperazine cocrystal 2 according to claim 11; and a pharmaceutically acceptable carrier.

15. The composition according to claim 14, wherein the rifaximin:piperazine cocrystal 2 is formulated as coated or uncoated tablets, hard or soft gelatin capsules, sugar-coated pills, lozenges, wafer sheets, pellets or powders in sealed packets.

16. A rifaximin polymorph Form kappa, wherein the polymorph Form kappa exhibits an X-ray powder diffraction pattern having characteristic peaks expressed in degrees 2θ at 6.83-6.94 (+/−0.20), 7.52-7.56 (+/−0.20), 7.68-7.78 (+/−0.20) and 8.30-8.34 (+/−0.20).

17. The rifaximin polymorph Form kappa according to claim 16, containing less than 5% by weight total impurities.

18. The rifaximin polymorph Form kappa according to claim 16, wherein the compound is at least 50% pure, or at least 75% pure, or at least 80% pure, or at least 90% pure, or at least 95% pure, or at least 98% pure.

19. A pharmaceutical composition comprising the rifaximin polymorph Form kappa according to claim 16; and a pharmaceutically acceptable carrier.

20. The composition according to claim 19, wherein the rifaximin Form kappa is formulated as coated or uncoated tablets, hard or soft gelatin capsules, sugar-coated pills, lozenges, wafer sheets, pellets or powders in sealed packets.

* * * * *